US008143210B2

(12) United States Patent
Shan et al.

(10) Patent No.: US 8,143,210 B2
(45) Date of Patent: *Mar. 27, 2012

(54) ENZYME TREATMENT OF FOODSTUFFS FOR CELIAC SPRUE

(75) Inventors: Lu Shan, Houston, TX (US); Chaitan Khosla, Palo Alto, CA (US)

(73) Assignees: The Board of Trustees of the Leland Stanford Junior University, Palo Alto, CA (US); Alvine Pharmaceuticals, Inc., San Carlos, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 11/775,824

(22) Filed: Jul. 10, 2007

(65) Prior Publication Data
US 2008/0095710 A1 Apr. 24, 2008

Related U.S. Application Data

(63) Continuation-in-part of application No. 10/969,314, filed on Oct. 19, 2004, now Pat. No. 7,320,788, which is a continuation-in-part of application No. 10/367,405, filed on Feb. 14, 2003, now Pat. No. 7,303,871.

(60) Provisional application No. 60/565,668, filed on Apr. 26, 2004, provisional application No. 60/357,238, filed on Feb. 14, 2002, provisional application No. 60/380,761, filed on May 14, 2002, provisional application No. 60/392,782, filed on Jun. 28, 2002, provisional application No. 60/422,933, filed on Oct. 31, 2002, provisional application No. 60/428,033, filed on Nov. 20, 2002, provisional application No. 60/435,881, filed on Dec. 20, 2002.

(51) Int. Cl.
*A61K 38/00* (2006.01)
*A61K 51/00* (2006.01)
(52) U.S. Cl. .................. 514/1.1; 530/300; 424/1.69
(58) Field of Classification Search .................. None
See application file for complete search history.

(56) References Cited

U.S. PATENT DOCUMENTS

| 4,203,967 A | 5/1980 | Gallo-Torres |
| 4,656,253 A | 4/1987 | Lewicki |
| 4,912,120 A | 3/1990 | Castelhano et al. |
| 4,929,630 A | 5/1990 | Castelhano et al. |
| 5,208,021 A | 5/1993 | Johnson et al. |
| 5,372,933 A | 12/1994 | Zamarron et al. |
| 5,716,794 A | 2/1998 | Tjota |
| 5,789,180 A | 8/1998 | Bernardin |
| 5,817,523 A | 10/1998 | Picarelli |
| 5,834,428 A | 11/1998 | Drucker |
| 6,197,356 B1 | 3/2001 | Girsh |
| 6,294,320 B1 | 9/2001 | Hruska et al. |
| 6,319,726 B1 | 11/2001 | Schuppan |
| 6,395,889 B1 | 5/2002 | Robison |
| 6,410,550 B1 | 6/2002 | Coe |
| 6,667,160 B2 | 12/2003 | Fine |
| 6,833,447 B1* | 12/2004 | Goldman et al. ............ 536/23.1 |
| 6,903,246 B2 | 6/2005 | Gallie |
| 6,962,989 B1* | 11/2005 | Pompejus et al. ........... 536/23.7 |
| 7,144,569 B1 | 12/2006 | Anderson et al. |
| 7,202,216 B2 | 4/2007 | Sollid et al. |
| 7,265,093 B2 | 9/2007 | Khosla et al. |
| 7,303,871 B2 | 12/2007 | Hausch et al. |
| 7,309,595 B2* | 12/2007 | Dekker et al. ................ 435/212 |
| 7,320,788 B2 | 1/2008 | Stan et al. |
| 7,462,688 B2 | 12/2008 | Khosla et al. |
| 7,534,426 B2 | 5/2009 | Piper et al. |
| 7,579,313 B2 | 8/2009 | Khosla et al. |
| 7,605,150 B2 | 10/2009 | Khosla et al. |
| 7,628,985 B2* | 12/2009 | Shan et al. ................. 424/94.63 |
| 7,910,541 B2* | 3/2011 | Hausch et al. ................. 514/1.1 |
| 7,943,312 B2* | 5/2011 | Hausch et al. ............. 424/94.64 |
| 2001/0007690 A1 | 7/2001 | Firsh |
| 2001/0036639 A1 | 11/2001 | Fine |
| 2002/0039599 A1 | 4/2002 | Lin et al. |
| 2002/0076834 A1 | 6/2002 | Detlef et al. |
| 2003/0215438 A1 | 11/2003 | Hausch |
| 2003/0224476 A1 | 12/2003 | Chou |
| 2004/0167069 A1 | 8/2004 | Khosla et al. |
| 2004/0241664 A1 | 12/2004 | Dekker et al. |
| 2005/0031603 A1 | 2/2005 | Hubertus de Jong et al. |
| 2005/0090653 A1 | 4/2005 | Klaveness et al. |
| 2005/0244823 A1 | 11/2005 | Drijfhout et al. |
| 2006/0052308 A1 | 3/2006 | Khosla et al. |
| 2006/0178299 A1 | 8/2006 | Anderson et al. |
| 2006/0240475 A1 | 10/2006 | Khosla et al. |
| 2008/0299108 A1 | 12/2008 | Khosla et al. |
| 2009/0156490 A1 | 6/2009 | Khosla et al. |
| 2009/0220554 A1 | 9/2009 | Griffin et al. |
| 2009/0304754 A1* | 12/2009 | Robic ........................... 424/400 |

FOREIGN PATENT DOCUMENTS

EP   0237082   9/1987
(Continued)

OTHER PUBLICATIONS

Qiao; et al., "Antigen presentation to celiac lesion-derived T cells of a 33-mer gliadin peptide naturally formed by gastrointestinal digestion", Journal of Immunology (2004), 173(3):1757-1762. Xia; et al., Equilibrium and kinetic analysis of the unusual binding behavior of a highly immunogenic gluten peptide to HLA-DQ2, Biochemistry (2005), 44(11):4442-4449.
Smith; et al., "Abnormal expression of dipeptidylpeptidase IV activity in enterocyte brush-border membranes of children suffering from coeliac disease", Experimental Physiology, Jul. 1990, 75(4):613-616.
Wruble, Milton, "Enteric Coating. I. A Laboratory Method for the Study and Control of Enteric Coatings", Journal of the American Pharmaceutical Association, Jul. 1935, XXIV(7):570-574.
Arentz-Hansen et al. "Celiac Lesion T Cells Recognizes Epitopes that Cluster in Regions of Gliadins Rich in Proline Residues" Gastroenterology, 2002, pp. 803-809, vol. 123, No. 3.

(Continued)

*Primary Examiner* — Maury Audet
(74) *Attorney, Agent, or Firm* — Bozicevic, Field & Francis LLP; Pamela J. Sherwood

(57) ABSTRACT

Administering an effective dose of glutenase to a Celiac or dermatitis herpetiformis patient reduces levels of toxic gluten oligopeptides, thereby attenuating or eliminating the damaging effects of gluten.

6 Claims, 22 Drawing Sheets

FOREIGN PATENT DOCUMENTS

| | | | |
|---|---|---|---|
| EP | 0905518 | A1 | 3/1999 |
| JP | 06070782 | A * | 3/1994 |
| WO | 94/26774 | | 11/1994 |
| WO | 96/10034 | | 4/1996 |
| WO | 00/42213 | | 7/2000 |
| WO | 01/25793 | A2 | 4/2001 |
| WO | 01/25793 | | 12/2001 |
| WO | 03/068170 | | 8/2003 |
| WO | 03/096984 | | 11/2003 |
| WO | 03104273 | | 12/2003 |
| WO | 2004/045392 | | 6/2004 |
| WO | 2005/049064 | | 6/2005 |

OTHER PUBLICATIONS

Bethune, et al. "Heterologous expression, purification, refolding, and structural-functional characterization of EP-B2, a self-activating barley cysteine endoprotease," Chemistry & Biology, 2006, pp. 637-647, vol. 13.

Castelhano et al., "Synthesis, Chemistry, and Absolute Configuratin of Novel Transglutaminiase Inhibitors Containing a 3-Halo-4,5-dihydroisoxazole" Bioorg. Chem., 1988, pp. 335-340, vol. 16.

Choi et al. "Chemistry and Biology of Dihydroisoxazole Derivatives: Selectives Inhibitors of Human Transglutaminase 2" Chem. & Biol., 2005, pp. 469-475, vol. 12.

de Ritis G. et al. "In Vitro (organ culture) Studies of the Toxicity of Specific A-Gliadin Peptides in celiac Disease" Gastroenbterology, 1988, pp. 41-49, vol. 94.

Freund, K. et al. "Transglutaminase inhibition by 2-[(2-Oxopropyl)thio]imidazolium derivatives: mechanism of factor XIIIa inactivation" Biochemistry, 1994, pp. 10109-10119, vol. 33.

Greenberg, C. et al. "Transglutaminases: multifunctional cross-linking enzymes that stabilize tissues" FASEB J., 1991, pp. 3071-3077, vol. 5.

Hartmann, G. et al. "Rapid degradation of gliadin peptides toxic for coeliac disease patients by proteases from germinating cereals" Journal of Cereal Science, Nov. 2006, pp. 368-371, vol. 44.

Hausch et al. "Design, synthesis, and evaluation of gluten peptide analogs as selective inhibitors of human tissue transglutaminase" Chem Biol., Mar. 2003, pp. 225-231, vol. 10, Issue 3.

Hitomi, K. et al. "GTP, an inhibitor of transglutaminases, is hydrolyzed by tissue-type transglutaminase (TGase 2) but not by epidermal-type transglutaminase (TGase 3)," Biosci. Biotechnol. Biochem., 2000, pp. 657-659, vol. 64, Issue 3.

Karpuj et al. "Prolonged survival and decreased abnormal movements in transgenic model of Huntington disease, with administration of the transglutaminase inhibitor cystamine" Nature Med., Feb. 2002, pp. 143-149, vol. 8, Issue 2.

Keillor, J. "Tissue Transglutaminase Inhibition" Chem. & Biol., 2005, pp. 410-412, vol. 12.

Kim et al. "Transglutaminases in disease" Neurochem. Int., 2002, pp. 85-103, vol. 40.

Lahteenoja et al. "Local challenge on oral mucosa with an alpha-gliadin related synthetic peptide in patients with celiac disease" Am. J. Gastroenterol., 2000, pp. 2880, vol. 95.

Lorand et al. "Novel inhibitors against the transglutaminase-catalysed crosslinking of lens proteins" Exp Eye Res., May 1998, pp. 531-536, vol. 66.

Martinet et al. "In vivo transglutaminase type 1 expression in normal lung, preinvasive bronchial lesions, and lung cancer" Am J Respir Cell Mol Biol., Apr. 2003, pp. 428-435, vol. 28, Issue 4.

Piper et al., "High selectivity of human tissue transglutaminase for immunoactive gliadin peptides: implications for celiac spure", Biochemistry, Jan. 8, 2002, pp. 386-393, vol. 41, Issue 1.

Piper, J., et al., "Effect of prolyl endopeptidase on digestive-resistant gliadin peptides in vivo," The Journal of Pharmacology and Experimental Therapeutics, 2004, pp. 213-219, vol. 311, Issue 1.

Sárdy, M. et al. "Epidermal transglutaminase (TGase 3) is the autoantigen of dermatitis herpetiformis" J. Exp. Med., 2002, pp. 747-757, vol. 195, Issue 6.

Shan, L. et al. "Structural Basis for Gluten Intolerance in Celiac Sprue" Science 2002, pp. 2275-2279, vol. 297.

Shan, L. et al. "Comparative biochemical analysis of three bacterial prolyl endopeptidases: implications of coeliac sprue," Biochem J, 2004, pp. 311-318, vol. 383.

Sjostrom et al. "Identification of a Gliadin T-Cell Epitope in Coeliac Disease: General Importance of Gliadin Deamidation for Intestinal T-Cell Recognition" Scandinavian Journal of Immunology, Aug. 1998, pp. 111-115(5), vol. 48, No. 2.

Stepniak, D. et al. "Highly efficient gluten degradation with a newly identified prolyl endoprotease: implications for celiac disease," Am J Physiol Gastrointest Liver Physiol, 2006, pp. G621-G629, vol. 291.

Vader et al. "The Gluten Response in Children with Celiac Sprue Disease is Directed Toward Multiple Gliadin and Glutenin Peptides" Gastroenterology, 2002, pp. 1729-1737, vol. 122.

Vader et al. "The HLA-DQ2 Gene Dose Effect in Celiac Disease is Doirectly Related to the Magnitude and Breadth of Gluten-Specific T Cell Responses" PNAS, Oct. 14, 2003, pp. 12390-12395, vol. 123, No. 3.

Zhang et al. "Identification of differentially expressed proteins in human glioblastoma cell lines and tumors" Glia., Apr. 15, 2003, pp. 194-208, vol. 42, Issue 2.

Frazer et al., "Gluten—Induced Enteropathy the Effect of Partially Digested Gluten", The Lancet, 1959, pp. 252-255.

Messer et al., "Oral Papain in Gluten Intolerance", The Lancet, 1976, pp. 1022.

Messer at al., "Studies on the Mechanism of Destruction of the Toxic Action of Wheat Gluten in Celiac Disease by Crude Papain", Gut, 1964, 5: 295-303.

Ahnen et al., Intestinal Aminooligopeptidase. In Vivo Synthesis on Intracellular Membranes of Rat Jejunum, 1982, J. Biol. Chem., 257, 12129-35.

Arentz-Hansen et al., The Intestinal T Cell Response to alpha—Gliadin in Adult Celiac Disease is Focused on a Single Deamidated Glutamine Targeted by Tissue Transglutaminase, 2000, J. Exp. Med., 191, 603-12.

Bordusa et al., The Specificity of Prolyl Endopeptidase From Flavobacterium Meningoseptum: Mapping the S' Subsites by Positional Scanning Via Acyl Transfer, 1998, Bioorg. Med. Chem., 6, 1775-80.

Colot et al., The Genes Encoding Wheat Storage Proteins: Towards a Molecular Understanding of Bread-Making Quality and Its Genetic Manipulation, 1990, Genet Eng., 12:225-41.

Database Derwent, Acc-No. 1996-329479, HLA-Binding Oligopeptide and an Immuno: Regulator Contgit—Used in the Treatment of Auto: Immune Disease, 1999.

Schuppan, Current Concepts of Celiac Disease Pathogenesis, 2000, Gastroenterology, 119, 234-42.

Wieser, The Precipitating Factor in Coeliac Disease, 1995, Baillieres Clin Gastroenterol, 9(2):191-207.

Wieser, 1996, Relation Between Structure an Dcoeliac Toxicity, Acta Paediatr Suppl., 412:3-9.

Yoshimoto et al., Prolyl Endopeptidase From Flavobacterium Meningosepticum: Cloning and Sequencing of the Enzyme Gene, 1991, J. Biochem., 110, 873-8.

Online-Medical Dictionary. "Amino acid". http://cancerweb.ncl.ac.uk/cgi-bin/omd?query=amino+acid. Nov. 13, 1997.

Lion. Flavobacterium meningosepticum. Genbank Accession #/EMBL #: D10980, Aug. 1, 1992. http://www.infobiogen.fr/srs71bin/cgi-bin/wgetz?-id+4jqa61Mc9PO+[uniprot-ID:PPCE_FLAME]+-e.

Auger; et al., "Solid-State 13C NMR Study of a Transglutaminase-Inhibitor Adduct", Biochemistry (1993), 32:3930-3934.

Cornell; et al., "In vitro mucosal digestion of synthetic gliadin-derived peptides in celiac disease", Journal of Protein Chemistry (1995), 14(5):335-339.

Goldsmith; et al., "Inhibition of Human Epidermal Transglutaminases In-Vitro and In-Vivo by Tyrosineamidomethyldihydrohaloisoxazoles", Journal of Investigative Dermatology (1991), 97(1):156-158.

Killackey; et al., "A New Class of Mechanism-Based Inhibitors of Translutaminase Enzymes Inhibits the Formation of Cross-Linked Envelopes by Human Malignant Keratinocytes", Molecular Pharmacology (1989), 35(5):701-706.

Piper; et al., "Effect of Prolyl Endopeptidase on Digestive-Resistant Gliadin Peptides in Vivo", Journal of Pharmacology and Experimental Therapeutics (2004), 311(1):213-219.

Shan; et al., "Comparative biochemical analysis of three bacterial prolyl endopeptidases: Implications for coeliac sprue", Biochemical Journal (2004), 382(2):311-318.

Watts; et al., "Structure-activity relationship analysis of the selective inhibition of transglutaminase 2 by dihydroisoxazoles", Journal of Medicinal Chemistry (2006), 49(25):7493-7501.

Arentz-Hansen, et al., "Production of a Panel of Recombinant Gliadins for the Characterisation of T Cell Reactivity in Coeliac Disease" Gut. (2000), 46(1):46-51.

Campbell, "Monoclonal Antibody Technology", Elsvier Science Publishers (1984), Section 1.3.4, pp. 1-32.

Garcia-Maroto, et al., "Nucleotide Sequence of a cDNA Encoding an Alpha/Beta-Type Gliadin from Hexaploid Wheat (*Triticum aestivum*)" Plant Molecular Biol. (1990), 14(5):867-868.

Hausch et al., "Intestinal digestive resistance of immunodominant gliadin peptides", Am J Physl Gastrointest Liver Physiol (2002); 283:G996-G1003.

Nägele, et al. "Analysis of Food and Feed by way of Partial Sequences of Characteristic Protein Components (Leader Peptides)", Z Lebensm Unters Forsch (1991), 192:415-421.

Parrot; et al., "Circular dichroism and nuclear magnetic resonance spectroscopic analysis of immunogenic gluten peptides and their analogs", Journal of Biological Chemistry (2002), 277(47):45572-45578.

Schuppan; et al., "A Molecular Warhead and its Target Tissue Transglutaminase and Celiac Sprue", Chemistry & Biology (2003), 10(3):199-201.

Siegel; et al., "Transglutaminase 2 inhibitors and their therapeutic role in disease states", Pharmacology & Therapeutics (2007), 115:232-245.

Sturgess et al., "Wheat peptide challenge in coeliac disease", The Lancet (1994), 343:758-761.

\* cited by examiner

FIGURE 11c

| | |
|---|---|
| LQLQPFPQPQLPYPQPQLPYPQPQLPYPQPQPF | MW (FM) |
| QPQPF | 616.3 |
| QPQLP   QPQLP   QPQLP | 582.2 |
| YPQPQLPYP | 1102.5 |
| YPQPQLPYP | |
| QPQLPYP | 842.4 |
| QPQLPYPQPQPF | 1439.7 |
| LQLQPFP | 842.3 |
| LQLQPFPQPQLP | 1405.6 |
| LQLQPFPQPQLPYP | 1665.7 |
| LQLQPFPQPQLPYPQPQLP | 2231.0 |

| | |
|---|---|
| LQLQPFPQPQLPYPQPQLPYPQPQLPYPQPQPF | MW (MX) |
| YPQPQPF | 876.4 |
| QPQPF | 616.3 |
| QPQLP   QPQLP   QPQLP | 582.2 |
| LQLQP | 598.2 |
| FPQP | 488.2 |
| YPQP   YPQP   YPQP | 504.2 |

FIGURE 15A
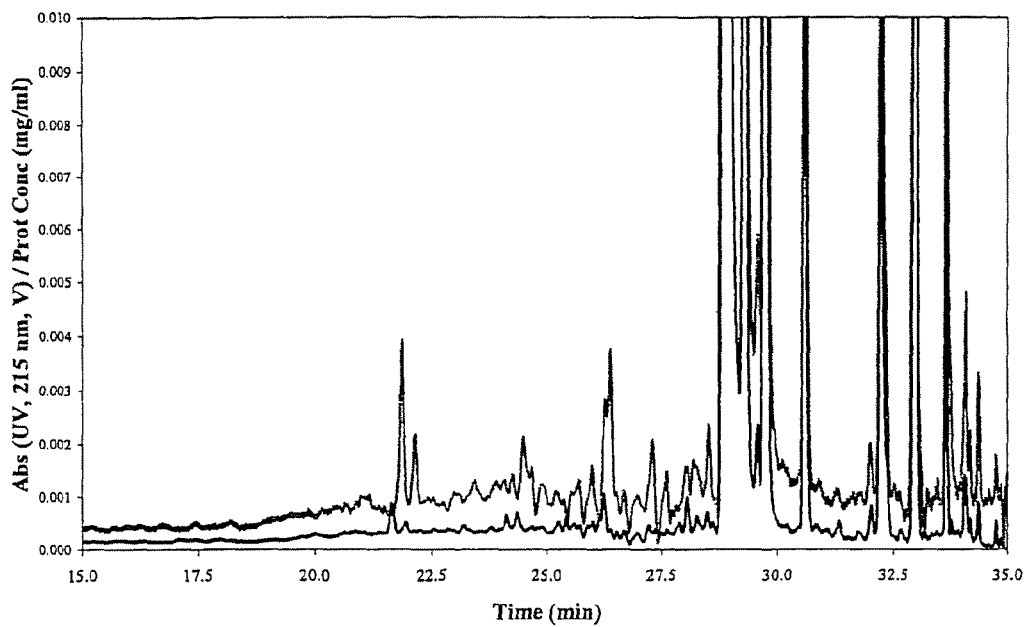
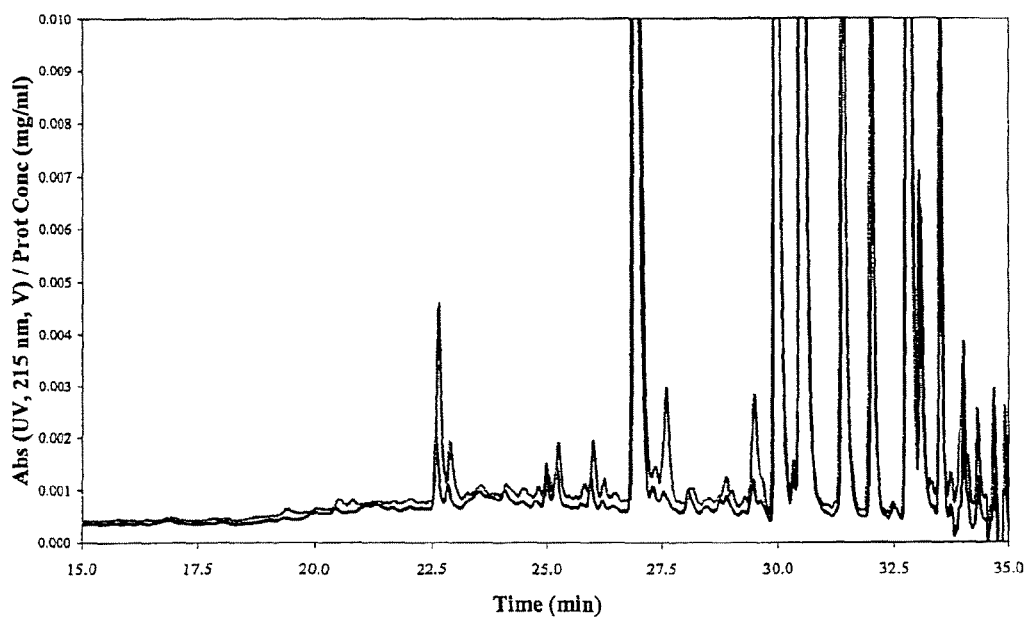
FIGURE 15B

ENZYME TREATMENT OF FOODSTUFFS FOR CELIAC SPRUE

This invention was made with Government support under contract DK063158 awarded by the National Institutes of Health. The Government has certain rights in this invention.

BACKGROUND OF THE INVENTION

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients supports a theory of an immunological nature of the disease. Antibodies to tissue transglutaminase (tTG) and gliadin appear in almost 100% of the patients with active Celiac Sprue, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villus atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue, improved methods of treating or ameliorating the effects of the disease are needed. The present invention addresses such needs.

SUMMARY OF THE INVENTION

The present invention provides methods for treating the symptoms of Celiac Sprue and/or dermatitis herpetiformis by decreasing the levels of toxic gluten oligopeptides in foodstuffs, either prior to or after ingestion by a patient. The present invention relates to the discovery that certain gluten oligopeptides resistant to cleavage by gastric and pancreatic enzymes, that the presence of such peptides results in toxic effects, and that enzymatic treatment can remove such peptides and their toxic effects. By digestion with glutenases, these toxic oligopeptides are cleaved into fragments, thereby preventing or relieving their toxic effects in Celiac Sprue or dermatitis herpetiformis patients.

In one aspect of the invention, a foodstuff is treated with a glutenase prior to consumption by the patient. In another aspect of the invention, a glutenase is administered to a patient and acts internally to destroy the toxic oligopeptides. In another aspect of the invention, a recombinant organism that produces a glutenase is administered to a patient. In another aspect of the invention, gene therapy is used to provide the patient with a gene that expresses a glutenase that destroys the toxic oligopeptides.

In one aspect of the invention, methods are provided for initial assessment of patients, and for monitoring patients during treatment. It has surprisingly been found that a high percentage of patients believed to be in remission were suffering from intestinal malabsorption and malfunction. In some embodiments of the invention, the subject therapy comprises the steps of monitoring and/or diagnosis with assays for intestinal malabsorption and malfunction. Such monitoring also finds use in the evaluation of the therapeutic efficacy of clinical protocols and/or formulations.

In one aspect, the invention provides methods for the administration of enteric formulations of one or more glutenases, each of which may be present as a single agent or a combination of active agents. In another aspect of the invention, stabilized forms of glutenases are administered to the patient, which stabilized forms are resistant to digestion in the stomach, e.g. to acidic conditions. Alternative methods of administration include genetic modification of patient cells, e.g. enterocytes, to express increased levels of peptidases capable of cleaving immunogenic oligopeptides of gliadin; pretreatment of foods with glutenases; the introduction of micro-organisms expressing such peptidases so as to transiently or permanently colonize the patient intestinal tract; and the like.

In another aspect, the invention provides pharmaceutical formulations containing one or more glutenases and a pharmaceutically acceptable carrier. Such formulations include formulations in which the glutenase is contained within an enteric coating that allows delivery of the active agent to the intestine and formulations in which the active agents are stabilized to resist digestion in acidic stomach conditions. The formulation may comprise one or more glutenases or a mixture or "cocktail" of agents having different activities.

In another aspect, the invention provides foodstuffs derived from gluten-containing foods that have been treated to remove or to reduce to non-toxic levels the gluten-derived oligopeptides that are toxic to Celiac Sprue patients, and methods for treating foods to hydrolyze toxic gluten oligopeptides. In other aspects, the invention provides recombinant microorganisms useful in hydrolyzing the gluten-derived oligopeptides that are toxic to Celiac Sprue patients from foodstuffs; methods for producing glutenases that digest the gluten-derived oligopeptides that are toxic to Celiac Sprue patents; purified preparations of the glutenases that digest the gluten-derived oligopeptides that are toxic to Celiac Sprue patents; and recombinant vectors that code for the expression of glutenases that digest the gluten-derived oligopeptides that are toxic to Celiac Sprue patents.

These and other aspects and embodiments of the invention are described in more detail below.

BRIEF DESCRIPTION OF THE DRAWINGS

FIG. 1A: LC-MS traces of peptides as shown, after digestion with 27 ng/µl rat brush border membrane (BBM) protein for the indicated time. Reaction products were separated by reversed phase HPLC and detected by mass spectroscopy (ion counts m/z=300-2000 g/mol). The indicated peptide fragments were confirmed by characteristic tandem MS fragmentation patterns. The SEQ ID NO:2 pyroQLQPFPQPQLPY peak corresponds to an N-terminally pyroglutaminated species, which is generated during HPLC purification of the synthetic starting material. FIG. 1B: Abundance of individual digestion products as a function of time. The peptide fragments in FIG. 1A were quantified by integrating the corresponding MS peak area (m/z=300-2000 g/mol). The resulting MS intensities are plotted as a function of digestion time (with BBM only). The digestion experiment was repeated in the presence of exogenous DPP IV from Aspergillus fumigatus (Chemicon International, CA, 0.28 µU DPP IV/ng BBM protein) and analyzed as above (open bars). The relative abundance of different intermediates could be estimated from the $UV_{280}$ traces and control experiments using authentic standards. The inserted scheme shows an interpretative diagram of the digestion pathways of SEQ ID NO:1) QLQPFPQPQLPY and its intermediates, the BBM peptidases involved in each step, and the amino acid residues that are released. The preferred breakdown pathway is indicated in bold. APN=aminopeptidase N, CPP=carboxypeptidase P, DPP IV=dipeptidyl dipeptidase IV.

FIG. 2A: (SEQ ID NO:3) PQPQLPYPQPQLPY was digested by 27 ng/µl brush border membrane (BBM) protein preparations for the indicated time and analyzed as in FIG. 1A. The identity of the starting material and the product (SEQ ID NO:4) PQPQLPYPQPQLP was corroborated by MSMS fragmentation. The intrinsic mass intensities of the two peptides were identical, and the $UV_{280}$ extinction coefficient of (SEQ ID NO:4) PQPQLPYPQPQLP was half of the starting material in accordance with the loss of one tyrosine. All other intermediates were ≦1%. The scheme below shows the proposed BBM digestion pathway of (SEQ ID NO:3) PQPQLPYPQPQLPY with no observed N-terminal processing (crossed arrow) and the removal of the C-terminal tyrosine by carboxypeptidase P (CPP) in bold. Further C-terminal processing by dipeptidyl carboxypeptidase (DCP) was too slow to permit analysis of the subsequent digestion steps (dotted arrows). FIG. 2B: Influence of dipeptidyl carboxypeptidase on C-terminal digestion. (SEQ ID NO:3) PQPQLPYPQPQLPY in phosphate buffered saline:Tris buffered saline=9:1 was digested by BBM alone or with addition of exogenous rabbit lung DCP (Cortex Biochemicals, CA) or captopril. After overnight incubation, the fraction of accumulated SEQ ID NO:4) PQPQLPYPQPQLP (compared to initial amounts of (SEQ ID NO:3) PQPQLPYPQPQLPY at t=0 min) was analyzed as in FIG. 2A, but with an acetonitrile gradient of 20-65% in 6-35 minutes.

FIGS. 15A and 15B. Analysis of rat intestinal content for gluten derived peptides in the absence or presence of enteric coated PEP capsules.

DETAILED DESCRIPTION OF THE EMBODIMENTS

Figure 1A:
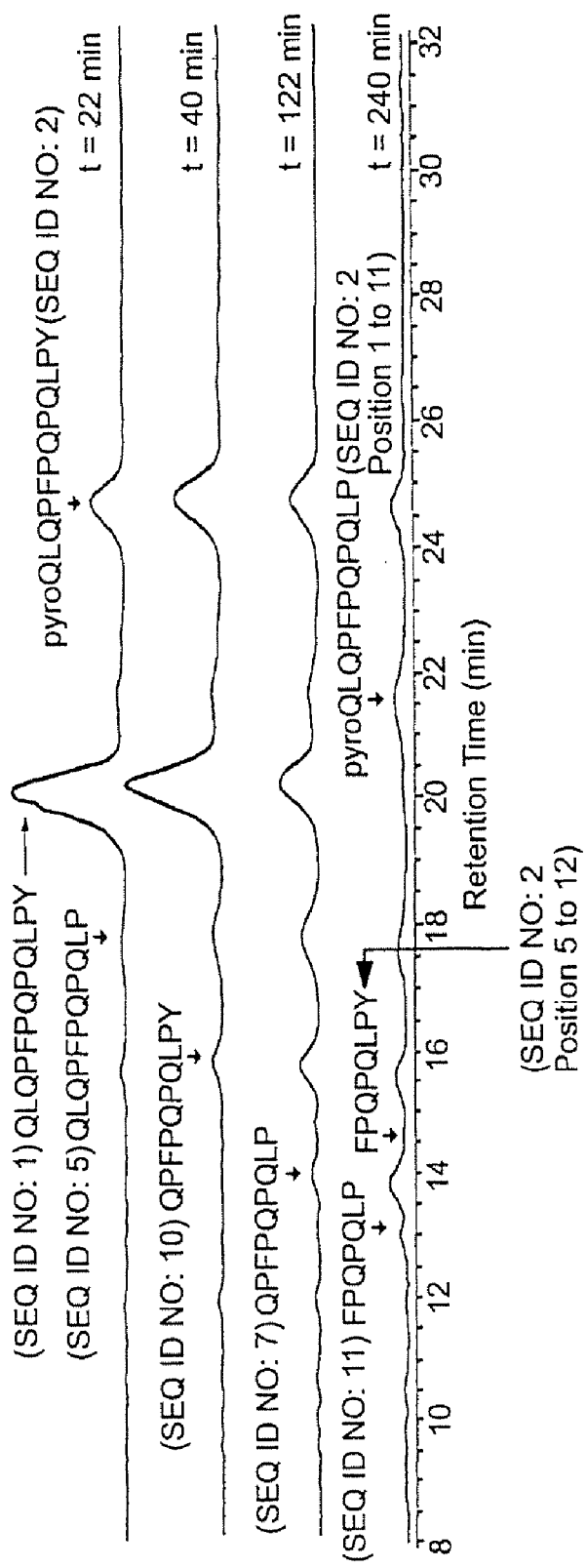
FIGS. 1A-1B. Brush border membrane catalyzed digestion of the immunodominant gliadin peptide.

Celiac Sprue and/or dermatitis herpetiformis are treated by digestion of gluten oligopeptides contained in foodstuffs consumed by individuals suffering from one or both conditions. Gluten oligopeptides are highly resistant to cleavage by gastric and pancreatic peptidases such as pepsin, trypsin, chymotrypsin, and the like. By providing for digestion of gluten oligopeptides with glutenase, oligopeptides are cleaved into fragments, thereby preventing the disease-causing toxicity.

Methods and compositions are provided for the administration of one or more glutenases inhibitors to a patient suffering from Celiac Sprue and/or dermatitis herpetiformis. In some patients, these methods and compositions will allow the patient to ingest glutens without serious health consequences, much the same as individuals that do not suffer from either of these conditions. In some embodiments, the formulations of the invention comprise a glutenase contained in an enteric coating that allows delivery of the active agent(s) to the intestine; in other embodiments, the active agent(s) is stabilized to resist digestion in acidic stomach conditions. In some cases the active agent(s) have hydrolytic activity under acidic pH conditions, and can therefore initiate the proteolytic process on toxic gluten sequences in the stomach itself. Alternative methods of administration provided by the invention include genetic modification of patient cells, e.g. enterocytes, to express increased levels of glutenases; and the introduction of micro-organisms expressing such glutenases so as to transiently or permanently colonize the patient's intestinal tract. Such modified patient cells (which include cells that are not derived from the patient but that are not immunologically rejected when administered to the patient) and microorganisms of the invention are, in some embodiments, formulated in a pharmaceutically acceptable excipient, or introduced in foods. In another embodiment, the invention provides foods pretreated or combined with a glutenase and methods for treating foods to remove the toxic oligopeptides of gluten.

The methods of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that may be treated by the methods of the invention include those diagnosed with celiac sprue through one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet. Amelioration of the above symptoms upon introduction of a strict gluten-free diet is a key hallmark of the disease. However, analysis of celiac patients has shown that a high level of patients believed to be in remission are, in fact, suffering malabsorption, as evidenced by indicia including, without limitation, xylose absorption tests, fecal fat analysis, lactulose/mannitol permeability tests, and the like. In some embodiments of the invention, patients are evaluated by examination of intestinal malabsorption for initial diagnosis, assessment, and/or monitoring during and after treatment.

These diagnostic approaches may be used in identifying patients who are responsive to protease therapy, and for clinical evaluation of candidate therapies. In particular, patient status may be assessed via a short-term (2-4 week), low-dose (2-10 g/day) gluten challenge, where intestinal malabsorption and malfunction (as judged by reduced xylose absorption, increased fecal fat excretion, and/or increased lactulose/mannitol permeability) is expected to worsen in response to such a gluten challenge. Therapeutic efficacy of a clinical protocol and/or formulation can be assessed in a crossover mode, where the patient is challenged alternately with gluten-only or with gluten+enzyme, separated by a washout period of 4-8 weeks, in combination with assessment of intestinal malabsorption. Alternatively, therapeutic efficacy can also be assessed by endoscopic evaluation during which biopsy samples are collected from the duodenum and upper jejunum, and subjected to histological analysis.

Given the safety of oral proteases, they also find a prophylactic use in high-risk populations, such as Type I diabetics, family members of diagnosed celiac patients, HLA-DQ2 positive individuals, and/or patients with gluten-associated symptoms that have not yet undergone formal diagnosis. Such patients may be treated with regular-dose or low-dose (10-50% of the regular dose) enzyme. Similarly, temporary high-dose use of such an agent is also anticipated for patients recovering from gluten-mediated enteropathy in whom gut function has not yet returned to normal, for example as judged by fecal fat excretion assays.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

Although the present invention is not to be bound by any theory of action, it is believed that the primary event in Celiac Sprue requires certain gluten oligopeptides to access antigen binding sites within the lamina propria region interior to the relatively impermeable surface intestinal epithelial layer. Ordinarily, oligopeptide end products of pancreatic protease processing are rapidly and efficiently hydrolyzed into amino acids and/or di- or tri-peptides by intestinal peptidases before they are transported across the epithelial layer. The enzymes of the GI tract proteolyze gluten slowly due to the proline- and glutamine-rich character of this important dietary protein source. Furthermore, the Celiac Sprue toxicity of gluten resides in the proline- and glutamine-rich segments of gluten. Therefore proteases with specificity toward proline and glutamine residues are expected to be useful for treating Celiac Sprue.

The normal assimilation of dietary proteins by the human gut can be divided into three major phases: (i) initiation of proteolysis in the stomach by pepsin and highly efficient endo- and C-terminal cleavage in the upper small intestine cavity (duodenum) by secreted pancreatic proteases and carboxypeptidases; (ii) further processing of the resulting oligopeptide fragments by exo- and endopeptidases anchored in the brush border surface membrane of the upper small intestinal epithelium (jejunum); and (iii) facilitated transport of the resulting amino acids, di- and tripeptides across the epithelial cells into the lamina propria, from where these nutrients enter capillaries for distribution throughout the body.

Because most proteases and peptidases normally present in the human stomach and small intestine are unable to hydrolyze the amide bonds of proline residues, it is shown herein that the abundance of proline and glutamine residues in gliadins and related proteins from wheat, rye and barley can constitute a major digestive obstacle for the enzymes involved in phases (i) and (ii) above. This leads to an increased concentration of relatively stable gluten derived oligopeptides in the gut. Furthermore, because aminopeptidase and especially carboxypeptidase activity towards oligopeptides with proline residues at the N- and C-termini, respectively, is low in the small intestine, detoxification of gluten oligopeptides in phase (iii) above is also slow. By administering peptidases capable of cleaving such gluten oligopeptides in accordance with the methods of the invention, the amount of toxic peptides is diminished, thereby slowing or blocking disease progression.

Tissue transglutaminase (tTGase), an enzyme found on the extracellular surface in many organs including the intestine, catalyzes the formation of isopeptide bonds between glutamine and lysine residues of different polypeptides, leading to protein-protein crosslinks in the extracellular matrix. The enzyme tTGase is the primary focus of the autoantibody response in Celiac Sprue. Gliadins, secalins and hordeins contain several sequences rich in Pro-Gln residues that are high-affinity substrates for tTGase; tTGase catalyzed deamidation of at least some of these sequences dramatically increases their affinity for HLA-DQ2, the class II MHC allele present in >90% Celiac Sprue patients. Presentation of these deamidated epitopes by DQ2 positive antigen presenting cells effectively stimulates proliferation of gliadin-specific T cells from intestinal biopsies of most Celiac Sprue patients. The toxic effects of gluten include immunogenicity of the gluten oligopeptides, leading to inflammation; the lectin theory predicts that gliadin peptides may also directly bind to surface receptors.

The present invention relates generally to methods and reagents useful in treating foodstuffs containing gluten with enzymes that digest the oligopeptides toxic to Celiac Sprue patients. Although specific enzymes are exemplified herein, any of a number of alternative enzymes and methods apparent to those of skill in the art upon contemplation of this disclosure are equally applicable and suitable for use in practicing the invention. The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

As used herein, the term "glutenase" refers to an enzyme useful in the methods of the present invention that is capable, alone or in combination with endogenous or exogenously added enzymes, of cleaving toxic oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively. For further discussion of gluten proteins, see the review by Wieser (1996) Acta Paediatr Suppl. 412:3-9, incorporated herein by reference.

In one embodiment, the term "glutenase" as used herein refers to a protease or a peptidase enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "protease" or "peptidase" can refer to a glutenase and as used herein describe a protein or fragment thereof with the capability of cleaving peptide bonds, where the scissile peptide bond may either be terminal or internal in oligopeptides or larger proteins. Prolyl-specific peptidases are glutenases useful in the practice of the present invention.

Glutenases of the invention include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. capsulata* (Genbank accession number AB010298), DCP I from rabbit (Genbank accession number X62551), DPP IV from *Aspergillus fumigatus* (Genbank accession number U87950) or cysteine proteinase B from *Hordeum vulgare* (Genbank accession number JQ1110).

Each of the above proteases described herein can be engineered to improve desired properties such as enhanced specificity toward toxic gliadin sequences, improved tolerance for longer substrates, acid stability, pepsin resistance, resistance to proteolysis by the pancreatic enzymes and improved shelf-life. The desired property can be engineered via standard protein engineering methods.

In one embodiment of the present invention, the glutenase is a PEP. Homology-based identification (for example, by a PILEUP sequence analysis) of prolyl endopeptidases can be routinely performed by those of skill in the art upon contemplation of this disclosure to identify PEPs suitable for use in the methods of the present invention. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningoscepticum, Aeromonas hydrophila, Aeromonas punctata, Novosphingobium capsulatum, Pyrococcus furiosus* and from mammalian sources are *Nostoc* and *Arabidopsis* enzymes are likely to be PEPs but have not been fully characterized to date. Homologs of the enzymes of interest may be found in publicly available sequence databases, and the methods of the invention include such homologs. Candidate enzymes are expressed using standard heterologous expression technologies, and their properties are evaluated using the assays described herein.

In one embodiment of the invention, the glutenase is *Flavobacterium meningosepticum* PEP (Genbank ID # D10980). Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme. A variety of assays have verified the therapeutic utility of this PEP. In vitro, this enzyme has been shown to rapidly cleave several toxic gluten peptides, including the highly inflammatory 33-mer, (SEQ ID NO:12) LQLQPF-PQPQLPYPQPQLPYPQPQLPYPQPQPF. In vivo it acts synergistically with the peptidases of the intestinal brush border membrane so as to rapidly detoxify these peptides, as well as gluten that has been pre-treated with gastric and pancreatic proteases. It has broad chain length specificity, making it especially well suited for the breakdown of long proline-rich peptides released into the duodenum from the stomach. The enzyme has a pH optimum around pH 7, and has high specific activity under conditions that mimic the weakly acidic environment of the upper small intestine. *Flavobacterium* PEP can cleave all T cell epitopes in gluten that have been tested to date. It has particular preference for the immunodominant epitopes found in alpha-gliadin. When grocery-store gluten is treated with this PEP, a rapid decrease in its antigenicity can be observed, as judged by LC-MS analysis and testing against polyclonal T cell lines derived from small intestinal biopsies from Celiac Sprue patients. The denatured protein is non-allergenic in rodents, rabbits and humans. It is relatively stable toward destruction by pancreatic proteases, an important feature since under physiological conditions it will be expected to act in concert with those enzymes.

Another enzyme of interest is *Myxococcus xanthus* PEP (Genbank ID# AF127082) SEQ ID NO:47. This enzyme possesses many of the advantages of the *Flavobacterium* PEP. It can cleave the 33-mer into small non-toxic peptides. Whereas the *Flavobacterium* enzyme appears to have a relatively strict preference for PQ bonds in gliadin peptides, the *Myxococcus* enzyme can cleave at PQ, PY and PF bonds, a feature that allows it to proteolyze a broader range of gluten epitopes. Compared to the *Flavobacterium* enzyme, it has equivalent stability toward the pancreatic proteases and superior stability toward acidic environments. The *Myxococcus* enzyme is well expressed in *E. coli*, making it feasible to produce this enzyme cheaply.

Another enzyme of interest is *Sphingomonas capsulata* PEP (Genbank ID# AB010298). This enzyme is comparable to the *Flavobacterium* and *Myxococcus* enzyme. It has broader sequence specificity than either the *Flavobacterium* or the *Myxococcus* PEP, and may therefore be able to destroy the widest range of antigenic epitopes. Like the *Myxococcus* enzyme, it is also well expressed in *E. coli*.

Another enzyme of interest is *Lactobacillus helveticus* PEP (Genbank ID# 321529). Unlike the above PEPs, this PEP is a zinc enzyme. It can efficiently proteolyze long peptide substrates such as the casein peptides (SEQ ID NO:28) YQEPVLGPVRGPFPIIV and (SEQ ID NO:29) RPKH-PIKHQ. Proteolysis occurs at all PV and PI subsites, suggesting the PEP prefers hydrophobic residues at the S1' position, as are frequently found in gluten. Since the producer strain of *L. helveticus* CNRZ32 is commonly used in cheesemaking, this enzyme has desirable properties as a food-grade enzyme.

Another enzyme of interest is *Penicillium citrinum* PEP (Genbank ID# D25535). This enzyme has been shown to possess PEP activity based on its ability to effectively cleave a number of Pro-Xaa bonds in peptides such as dynorphin A and substance P. The putative metalloprotease has the advantages of small size and a pH profile that renders it suitable to working in concert with the pancreatic enzymes in the duodenum. As such, it is a good candidate for the treatment of Celiac Sprue.

Other than proline, glutamine residues are also highly prevalent in gluten proteins. The toxicity of gluten in Celiac Sprue has been directly correlated to the presence of specific Gln residues. Therefore, glutamine-specific proteases are also beneficial for the treatment of Celiac Sprue. Since oats contain proteins that are rich in glutamine but not especially rich in proline residues, an additional benefit of a glutamine-specific protease is the improvement of oat tolerance in those celiac patients who show mild oat-intolerance. An example of such a protease is the above-mentioned cysteine endoproteinase that cleaves gluten proteins rapidly with a distinct preference for post-Gln cleavage. This enzyme is *Hordeum vulgare* endoprotease (Genbank accession U19384), which has been shown to efficiently digest .alpha.2-gliadin. The enzyme is active under acidic conditions, and is useful as an orally administered dietary supplement. A gluten-containing diet may be supplemented with orally administered proEPB2, resulting in effective degradation of immunogenic gluten peptides in the acidic stomach, before these peptides enter the intestine and are presented to the immune system. Proteins with high sequence similarity to this enzyme are also of interest. An advantage of these enzymes is that they are considered as safe for human oral consumption, due to their presence in dietary gluten from barley.

Intestinal dipeptidyl peptidase IV and dipeptidyl carboxypeptidase I are the rate-limiting enzymes in the breakdown of toxic gliadin peptides from gluten. These enzymes are bottlenecks in gluten digestion in the mammalian small intestine because (i) their specific activity is relatively low compared to other amino- and carboxy-peptidases in the intestinal brush border; and (ii) due to their strong sensitivity to substrate chain length, they cleave long immunotoxic peptides such as the 33-mer extremely slowly. Both these problems can be ameliorated through the administration of proline-specific amino- and carboxy-peptidases from other sources. For example the X-Pro dipeptidase from *Aspergillus oryzae* (GenBank ID# BD191984) and the carboxypeptidase from *Aspergillus saitoi* (GenBank ID# D25288) can improve gluten digestion in the Celiac intestine.

A glutenase of the invention includes a peptidase or protease that has a specific activity of at least 2.5 U/mg, preferably 25 U/mg and more preferably 250 U/mg for cleavage of a peptide comprising one of more of the following motifs: Gly-Pro-pNA, Z-Gly-Pro-pNA (where Z is a benzyloxycarbonyl group), and Hip-His-Leu, where "Hip" is hippuric acid, pNA is para-nitroanilide, and 1 U is the amount of enzyme required to catalyze the turnover of 1 μmole of substrate per minute. Chromogenic substrates may be utilized in screening, e.g. substrates such as Cbz-Gly-Pro-pNA or Suc-Ala-Pro-pNA enables identification of proline-specific proteases. Similar substrates can also be used to identify glutamine-specific proteases. These assays can be monitored by UV-Vis spectrophotometric methods.

A glutenase of the invention includes an enzyme belonging to any of the following enzyme classifications: EC 3.4.21.26, EC 3.4.14.5, or EC 3.4.15.1.

A glutenase of the invention includes an enzyme having a kcat/Km of at least about 2.5 $s^{-1}$ $M^{-1}$, usually at least about 250 $s^{-1}$ $M^{-1}$ and preferably at least about 25000 $s^{-1}$ $M^{-1}$ for cleavage of any of the following peptides, including known T cell epitopes in gluten, under optimal conditions: (SEQ ID NO:1) QLQPFPQPQLPY or PFPQPQLPY, (SEQ ID NO:3) PQPQLPYPQPQLPY or PQPQLPYPQ, (SEQ ID NO:13) QPQQSFPQQQ or PQQSFPQQQ, (SEQ ID NO:14) QLQPFPQPELPY, (SEQ ID NO:15) PQPELPYPQPELPY, (SEQ ID NO:16) QPQQSFPEQQ; (SEQ ID NO: 30) IQPQQ-PAQL; (SEQ ID NO:31) QQPQQPYPQ; (SEQ ID NO:32) SQPQQQFPQ; (SEQ ID NO:33) QQPFPQQPQ; or (SEQ ID NO:34) PFSQQQQPV. Cleavage of longer, physiologically generated peptides containing one or more of the above epitopes may also be assessed, for example cleavage of the 33-mer from alpha-gliadin, (SEQ ID NO:12) LQLQPF (PQPQLPY)₃PQPQPF, and the 26-mer from gamma-gliadin, (SEQ ID NO:35) FLQPQQPFPQQPQQPYPQQPQQPFPQ.

A glutenase of the invention includes peptidase or protease having a specificity kcat/Km>2 $mM^{-1}s^{-1}$ for the quenched fluorogenic substrate (SEQ ID NO:36) Abz-QPQQP-Tyr (NO₂)-D. These assays can be monitored by HPLC or fluorescence spectroscopy. For the latter assays, suitable fluorophores can be attached to the amino- and carboxy-termini of the peptides.

A glutenase useful in the practice of the present invention can be identified by its ability to cleave a pretreated substrate to remove toxic gluten oligopeptides, where a "pretreated substrate" is a gliadin, hordein, secalin or avenin protein that has been treated with physiological quantities of gastric and pancreatic proteases, including pepsin (1:100 mass ratio), trypsin (1:100), chymotrypsin (1:100), elastase (1:500), and carboxypeptidases A and B (1:100). Pepsin digestion may be performed at pH 2 for 20 min., to mimic gastric digestion, followed by further treatment of the reaction mixture with trypsin, chymotrypsin, elastase and carboxypeptidase at pH 7 for 1 hour, to mimic duodenal digestion by secreted pancreatic enzymes. The pretreated substrate comprises oligopeptides resistant to digestion, e.g. under physiological conditions. A glutenase may catalyze cleavage of pepsin-trypsin-chymotrypsin-elastase-carboxypeptidase (PTCEC) treated gluten such that less than 10% of the products are longer than (SEQ ID NO:3, aa 1-9) PQPQLPYPQ (as judged by longer retention times on a C18 reverse phase HPLC column monitored at $A_{215}$).

The ability of a peptidase or protease to cleave a pretreated substrate can be determined by measuring the ability of an enzyme to increase the concentration of free NH₂-termini in a reaction mixture containing 1 mg/ml pretreated substrate and 10 μg/ml of the peptidase or protease, incubated at 37° C. for 1 hour. A glutenase useful in the practice of the present invention will increase the concentration of the free amino termini under such conditions, usually by at least about 25%, more usually by at least about 50%, and preferably by at least about 100%. A glutenase includes an enzyme capable of reducing the residual molar concentration of oligopeptides greater than about 1000 Da in a 1 mg/ml "pretreated substrate" after a 1 hour incubation with 10 μg/ml of the enzyme by at least about 2-fold, usually by at least about 5-fold, and preferably by at least about 10-fold. The concentration of such oligopeptides can be estimated by methods known in the art, for example size exclusion chromatography and the like.

A glutenase of the invention includes an enzyme capable of detoxification of whole gluten, as monitored by polyclonal T cell lines derived from intestinal biopsies of celiac patients; detoxification of whole gluten as monitored by LC-MS-MS; and/or detoxification of whole gluten as monitored by ELISA assays using monoclonal antibodies capable of recognizing sequences specific to gliadin.

For example, a glutenase may reduce the potency by which a "pretreated substrate" can antagonize binding of (SEQ ID NO:17) PQPELPYPQPQLP to HLA-DQ2. The ability of a substrate to bind to HLA-DQ is indicative of its toxicity; fragments smaller than about 8 amino acids are generally not stably bound to Class II MHC. Treatment with a glutenase that digests toxic oligopeptides, by reducing the concentration of the toxic oligopeptides, prevents a mixture containing them from competing with a test peptide for MHC binding. To test whether a candidate glutenase can be used for purposes of the present invention, a 1 mg/ml solution of "pretreated substrate" may be first incubated with 10 μg/ml of the candidate glutenase, and the ability of the resulting solution to displace radioactive (SEQ ID NO:18) PQPELPYPQPQPLP pre-bound to HLA-DQ2 molecules can then be quantified, with a reduction of displacement, relative to a non-treated control, indicative of utility in the methods of the present invention.

A glutenase of the invention includes an enzyme that reduces the anti-tTG antibody response to a "gluten challenge diet" in a Celiac Sprue patient by at least about 2-fold, more usually by at least about 5-fold, and preferably by at least about 10-fold. A "gluten challenge diet" is defined as the intake of 100 g bread per day for 3 days by an adult Celiac Sprue patient previously on a gluten-free diet. The anti-tTG antibody response can be measured in peripheral blood using standard clinical diagnostic procedures, as known in the art.

Excluded from the term "glutenase" are the following peptidases: human pepsin, human trypsin, human chymotrypsin, human elastase, papaya papain, and pineapple bromelain, and usually excluded are enzymes having greater than 98% sequence identity at the amino acid level to such peptidases, more usually excluded are enzymes having greater than 90% sequence identity at the amino acid level to such peptidases, and preferably excluded are enzymes having greater than 70% sequence identity at the amino acid level to such peptidases.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Eng* (N Y) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. In one aspect of the present invention, genetically modified plants are provided that differ from their naturally occurring counterparts by having gliadin proteins that contain a reduced content of glutamine and proline residues.

Examples of gliadin sequences include but are not limited to wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal human digestion of gliadins and related storage proteins as described above, from dietary cereals, e.g. wheat, rye, barley, and the like. Such oligopeptides are believed to act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO:8). Determination of whether an oligopeptide is immunogenic for a particular patient is readily determined by standard T cell activation and other assays known to those of skill in the art.

As demonstrated herein, during digestion, peptidase resistant oligopeptides remain after exposure of glutens, e.g. gliadin, to normal digestive enzymes. Examples of peptidase resistant oligopeptides are provided, for example, as set forth in SEQ ID NO:5, 6, 7 and 10. Other examples of immunogenic gliadin oligopeptides are described in Wieser (1995) Baillieres Clin Gastroenterol 9(2):191-207, incorporated herein by reference.

Determination of whether a candidate enzyme will digest a toxic gluten oligopeptide, as discussed above, can be empirically determined. For example, a candidate may be combined with an oligopeptide comprising one or more Gly-Pro-pNA, Z-Gly-Pro-pNA, Hip-His-Leu, Abz-QLP-Tyr(NO$_2$)-PQ, Abz-PYPQPQ-Tyr(NO$_2$), PQP-Lys(Abz)-LP-Tyr(NO$_2$)-PQPQLP, PQPQLP-Tyr(NO$_2$)-PQP-Lys(Abz)-LP motifs; with one or more of the oligopeptides (SEQ ID NO:1) QLQPFPQPQLPY, (SEQ ID NO:3) PQPQLPYPQPQLPY, (SEQ ID NO:13) QPQQSFPQQQ, (SEQ ID NO:14) QLQPFPQPELPY, (SEQ ID NO:15) PQPELPYPQPELPY, (SEQ ID NO:16) QPQQSFPEQQ or (SEQ ID NO:12) LQLQPFPQPQLPYPQPQLPYPQPQLPYPQPQPF; or with a pretreated substrate comprising one or more of gliadin, hordein, secalin or avenin proteins that have been treated with physiological quantities of gastric and pancreatic proteases. In each instance, the candidate is determined to be a glutenase of the invention if it is capable of cleaving the oligopeptide. Glutenases that have a low toxicity for human cells and are active in the physiologic conditions present in the intestinal brush border are preferred for use in some applications of the invention, and therefore it may be useful to screen for such properties in candidate glutenases.

Measurements of gastrointestinal tract (GIT) permeability and malabsorption are useful in the analysis patients for therapy, of monitoring therapy, and for assessment of candidate agents, formulations and dosing protocols. Detoxification of whole gluten may be judged by a double-blinded crossover trial in celiac patients administered with 5-20 g gluten/day for 2 weeks. Gluten induced intestinal malfunction can be measured by standard absorption tests before and after each two week period. Intestinal malabsorption and malfunction is expected to worsen in response to such a gluten challenge, unless the gluten is detoxified by the glutenase or combination of glutenases.

Various such tests are known in the art. Tests of interest include intestinal permeability measured by a human alphalactalbumin, beta-lactoglobulin, mannitol, and/or lactulose test, or gastric permeability with a sucrose test (see Vogelsang et al. (1996) Gastroenterology 111:1, 73-7; Kuitunen and Savilahti (1996) J Pediatr Gastroenterol Nutr. 22:2, 197-204). The absorption of lactulose and mannitol may also be measured in serum after oral ingestion of test sugars, e.g. by HPLC determination of lactulose and mannitol (see Fleming et al. (1996) Clin Chem. 42:3, 445-8).

D-xylose is a pentose sugar which when ingested, is absorbed from the jejunum and excreted, largely unchanged, in the urine. Absorption of xylose is a measure of the intestine's ability to absorb monosaccharides. No standard protocol is defined. A 25 g bolus is widely used being taken with 500 ml of water after an overnight fast. Absorption is assessed from urine specimens collected over a 5 hour period or alternatively, from blood xylose measured 1-2 hours after ingestion. Normal results are serum xylose concentration at 1 hr in excess of 1.3 mM, urinary xylose excretion in excess of 4 g/5 hr. Hydrogen breath tests (H2-BT) are also used to diagnose carbohydrate malabsorption. Alveolar breath samples may be obtained before administering orally 25 g of D-xylose and thereafter at 30 min intervals for 5 hr. Samples are analyzed for H2 by chromatography (see Casellas et al. (1996) Dig Dis Sci. 41:10, 2106-11).

Other tests monitor fat malabsorption. For example, in a 72-hour fecal fat challenge, 100 g fat is ingested for three days, and the fat in stool measured for three days. In a normal patient the fecal fat will be less than about 7 g/day, while abnormal readings may be from about 10-60 g/day. Quantitative tests may also find use, for example an oil red 0 stain of fecal matter.

Schilling's test measures B12 absorption. Excess intake of radioactive (cobalt-57) B12 gets excreted in urine. The patient is loaded ahead of the test with 1M B12, and then administered oral radioactive B12; where urinary excretion is measured.

The oligopeptide or protein substrates for such assays may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Recombinant DNA technology can also be used to produce the peptide.

Candidate glutenases for use in the practice of the present invention can be obtained from a wide variety of sources, including libraries of natural and synthetic proteins. For example, numerous means are available for random and directed mutation of proteins. Alternatively, libraries of natural proteins in the form of bacterial, fungal, plant and animal extracts are available or readily produced. Extracts of germinating wheat and other grasses is of interest as a source of candidate enzymes. Natural or synthetically produced libraries and compounds are readily modified through conventional chemical, physical and biochemical means, and such means can be used to produce combinatorial libraries. Known pharmacological agents may be subjected to directed or random chemical modifications, such as acylation, alkylation, esterification, and amidification, to produce structural analogs of proteins.

Generally, a variety of assay mixtures are run in parallel with different peptidase concentrations to obtain a differential response to the various concentrations. Typically, one of these concentrations serves as a negative control, i.e. at zero concentration or below the level of detection. A variety of other reagents may be included in a screening assay. These include reagents like salts, detergents, and the like that are used to facilitate optimal activity and/or reduce non-specific or background interactions. Reagents that improve the efficiency of the assay may be used. The mixture of components is added in any order that provides for the requisite activity. Incubations are performed at any suitable temperature, typically between 4 and 40° C. Incubation periods are selected for optimum activity but can also be optimized to facilitate rapid high-throughput screening or other purposes. Typically, between 0.1 and 1 hours will be sufficient.

The level of digestion of the toxic oligopeptide can be compared to a baseline value. The disappearance of the starting material and/or the presence of digestion products can be monitored by conventional methods. For example, a detectable marker can be conjugated to a peptide, and the change in molecular weight associated with the marker is then determined, e.g. acid precipitation, molecular weight exclusion, and the like. The baseline value can be a value for a control sample or a statistical value that is representative a control population. Various controls can be conducted to ensure that an observed activity is authentic, including running parallel reactions, positive and negative controls, dose response, and the like.

Active glutenases identified by the screening methods described herein can serve as lead compounds for the synthesis of analog compounds to identify glutenases with improved properties. Identification of analog compounds can be performed through use of techniques such as self-consistent field (SCF) analysis, configuration interaction (CI) analysis, and normal mode dynamics analysis.

In one embodiment of the invention, the glutenase is a prolyl endopeptidase (PEP, EC 3.4.21.26). Prolyl endopeptidases are widely distributed in microorganisms, plants and animals, and have been cloned from *Flavobacterium meningosepticum*, (Yoshimoto et al. (1991) J. Biochem. 110, 873-8); *Aeromonas hydrophyla* (Kanatani et al (1993) J. Biochem. 113, 790-6); *Sphingomonas capsulata* (Kabashima et al. (1998) Arch. Biochem. Biophys. 358, 141-148), *Pyrococcus furious* (Robinson et al. (1995) Gene 152, 103-6); pig (Rennex et al. (1991) Biochemistry 30, 2195-2030); and the like. The suitability of a particular enzyme is readily determined by the assays described above, by clinical testing, determination of stability in formulations, and the like. Other sources of PEP include *Lactobacilli* (Habibi-Najafi et al. (1994) J. Dairy Sci. 77, 385-392), from where the gene of interest can be readily cloned based on sequence homology to the above PEP's or via standard reverse genetic procedures involving purification, amino-acid sequencing, reverse translation, and cloning of the gene encoding the target extracellular enzyme.

In another embodiment of the invention, glutenases are peptidases present in the brush border, which are supplemented. Formulations of interest may comprise such enzymes in combination with other peptidases. Peptidases present in brush border include dipeptidyl peptidase IV (DPP IV, EC 3.4.14.5), and dipeptidyl carboxypeptidase (DCP, EC 3.4.15.1). The human form of these proteins may be used, or modified forms may be isolated from other suitable sources. Example of DPP IV enzymes include *Aspergillus* spp. (e.g. Byun et al. (2001) J. Agric. Food Chem. 49, 2061-2063), ruminant bacteria such as *Prevotella albensis* M384 (NCBI protein database Locus # CAC42932), dental bacteria such as *Porphyromonas gingivalis* W83 (Kumugai et al. (2000) Infect. Immun. 68, 716-724), *lactobacilli* such as *Lactobacillus helveticus* (e.g. Vesanto, et al, (1995) Microbiol. 141, 3067-3075), and *Lactococcus lactis* (Mayo et al., (1991) Appl. Environ. Microbiol. 57, 38-44). Other DPP IV candidates can readily be recognized based on homology to the above enzymes, preferably >30% sequence identity. Similarly, secreted dipeptidyl carboxypeptidases that cleave C-terminal X-Pro sequences are found in many microbial sources including *Pseudomonas* spp (e.g. Ogasawara et al, (1997) Biosci. Biotechnol. Biochem. 61, 858-863), *Streptomyces* spp. (e.g. Miyoshi et al., (1992) J. Biochem. 112, 253-257) and *Aspergilli* spp. (e.g. Ichishima et al., (1977) J. Biochem. 81, 1733-1737). Of particular interest is the enzyme from *Aspergillus saitoi* (Ichishima), due to its high activity at acidic pH values. Although the genes encoding many of these enzymes have not yet been cloned, they can be readily cloned by standard reverse genetic procedures. The DCP I enzymes can be purified from the extracellular medium based on their ability to hydrolyze (SEQ ID NO:19) Z-Gly-Pro-Leu-Gly-Pro, Z-Gly-Pro, or Hip-Gly-Pro. Alternatively, putative DCP I genes can be identified based on homology to the *E. coli* enzyme (NCBI protein database Locus CAA41014.)

In another embodiment of the invention, glutenases are endoproteases found in developing grains of toxic cereals such as wheat, barley and rye. For example, Dominguez and Cejudo (Plant Physiol. 112, 1211-1217, 1996) have shown that the endosperm of wheat (i.e. the part of the grain that contains gliadin and glutenin) contains a variety of neutral and acid proteases. Although these proteases have not been individually characterized, they are expected to be an especially rich source of glutenases. Moreover, although the genes encoding these proteases have not yet been cloned, Dominguez and Cejudo have established a convenient SDS-PAGE assay for identification and separation of these proteases. After excision of the corresponding protein bands from the gel, limited sequence information can be obtained. The cDNA encoding these proteases can therefore be readily cloned from this information using established reverse genetic procedures, and expressed in heterologous bacterial or fungal hosts. Of particular interest are proteases that hydrolyze α2-gliadin within the 33-mer amino acid sequence identified in Example 2 below. Of further interest are the subset of these proteases that retain activity at acidic pH values (pH2-5) encountered in the stomach.

The amino acid sequence of a glutenase, e.g. a naturally occurring glutenase, can be altered in various ways known in the art to generate targeted changes in sequence and additional glutenase enzymes useful in the formulations and compositions of the invention. Such variants will typically be functionally-preserved variants, which differ, usually in sequence, from the corresponding native or parent protein but still retain the desired biological activity. Variants also include fragments of a glutenase that retain enzymatic activity. Various methods known in the art can be used to generate targeted changes, e.g. phage display in combination with random and targeted mutations, introduction of scanning mutations, and the like.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

Glutenase fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac Sprue.

Modifications of interest that do not alter primary sequence include chemical derivatization of proteins, e.g., acetylation or carboxylation. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al. (2000) *J. Biol. Chem.* 275:23783-23789). Analogs of such proteins include those containing residues other than naturally occurring L-amino acids, e.g. D-amino acids or non-naturally occurring synthetic amino acids.

The glutenase proteins of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. Using synthesizers, one can readily substitute for the naturally occurring amino acids one or more unnatural amino acids. The particular sequence and the manner of preparation will be determined by convenience, economics, purity required, and the like. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

The glutenase proteins useful in the practice of the present invention may also be isolated and purified in accordance with conventional methods from recombinant production systems and from natural sources. Protease production can be achieved using established host-vector systems in organisms such as *E. coli, S. cerevisiae, P. pastoris, Lactobacilli, Bacilli* and *Aspergilli*. Integrative or self-replicative vectors may be used for this purpose. In some of these hosts, the protease is expressed as an intracellular protein and subsequently purified, whereas in other hosts the enzyme is secreted into the extracellular medium. Purification of the protein can be performed by a combination of ion exchange chromatography, Ni-affinity chromatography (or some alternative chromatographic procedure), hydrophobic interaction chromatography, and/or other purification techniques. Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one aspect, the present invention provides a purified preparation of a glutenase. Prior to the present invention, there was no perceived need for a glutenase that could be ingested by a human or mixed with a foodstuff. Thus, prior to the present invention most glutenases did not exist in a form free of contaminants that could be deleterious to a human if ingested. The present invention creates a need for such glutenase preparations and provides them and methods for preparing them. In a related embodiment, the present invention provides novel foodstuffs that are derived from gluten-containing foodstuffs but have been treated to reduce the concentration and amount of the oligopeptides and oligopeptide sequences discovered to be toxic to Celiac Sprue patients. While gluten-free or reduced-gluten content foods have been made, the foodstuffs of the present invention differ from such foodstuffs not only by the manner in which they are prepared, by treatment of the foodstuff with a glutenase, but also by their content, as the methods of the prior art result in alteration of non-toxic (to Celiac Sprue patients) components of the foodstuff, resulting in a different taste and composition. Prior art foodstuffs include, for example, Codex Alimentarius wheat starch, which is available in Europe and has <100 ppm gluten. The starch is usually prepared by processes that take advantage of the fact that gluten is insoluble in water whereas starch is soluble.

In one embodiment of the present invention, a Celiac Sprue patient is, in addition to being provided a glutenase or food treated in accordance with the present methods, provided an inhibitor of tissue transglutaminase, an anti-inflammatory agent, an anti-ulcer agent, a mast cell-stabilizing agents, and/ or and an-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the glutenases and treated foodstuffs of the invention can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

The glutenase proteins of the invention and/or the compounds administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the glutenase and/or other compounds can be achieved in various ways, usually by oral administration. The glutenase and/or other compounds may be systemic after administration or may be localized by virtue of the formulation, or by the use of an implant that acts to retain the active dose at the site of implantation.

In pharmaceutical dosage forms, the glutenase and/or other compounds may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. A number of methods are available in the art for the efficient delivery of enterically coated proteins into the small intestinal lumen. Most methods rely upon protein release as a result of the sudden rise of pH when food is released from the stomach into the duodenum, or upon the action of pancreatic proteases that are secreted into the duodenum when food enters the small intestine. For intestinal delivery of a PEP and/or a glutamine specific protease, the enzyme is usually lyophilized in the presence of appropriate buffers (e.g. phosphate, histidine, imidazole) and excipients (e.g. cryoprotectants such as sucrose, lactose, trehalose). Lyophilized enzyme cakes are blended with excipients, then filled into capsules, which are enterically coated with a polymeric coating that protects the protein from the acidic environment of the stomach, as well as from the action of pepsin in the stomach. Alternatively, protein microparticles can also be coated with a protective layer. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

Gluten detoxification for a gluten sensitive individual can commence as soon as food enters the stomach, since the acidic environment (~pH 2) of the stomach favors gluten solubilization. Introduction of an acid-stable PEP or glutamine-specific protease into the stomach will synergize with the action of pepsin, leading to accelerated destruction of toxic peptides upon entry of gluten in the small intestines of celiac patients. In contrast to a PEP that acts in the small intestine, gastric enzymes need not be formulated with enteric coatings. Indeed, since several proteases (including the above-mentioned cysteine proteinase from barley) self-activate by cleaving the corresponding pro-proteins under acidic conditions. In one embodiment of the invention, the formulation comprises a pro-enzyme that is activated in the stomach.

In another embodiment, a microorganism, for example bacterial or yeast culture, capable of producing glutenase is administered to a patient. Such a culture may be formulated as an enteric capsule; for example, see U.S. Pat. No. 6,008,027, incorporated herein by reference. Alternatively, microorganisms stable to stomach acidity can be administered in a capsule, or admixed with food preparations.

In another embodiment, the glutenase is admixed with food, or used to pre-treat foodstuffs containing glutens. Glutenase present in foods can be enzymatically active prior to or during ingestion, and may be encapsulated or otherwise treated to control the timing of activity. Alternatively, the glutenase may be encapsulated to achieve a timed release after ingestion, e.g. in the intestinal tract.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, the glutenase may be administered in dosages of 0.01 mg to 500 mg/kg body weight per day, e.g. about 20 mg/day for an average person. Efficient proteolysis of gluten in vivo for an adult may require at least about 500 units of a therapeutically efficacious enzyme, usually at least about 1000 units, more usually at least about 2000 units, and not more than about 50,000 units, usually not more than about 20,000 units, where one unit is defined as the amount of enzyme required to hydrolyze 1 µmol Cbz-Gly-Pro-pNA (for PEP) or Cbz-Gly-Gln-pNA (for a glutamine-specific protease) per min under specified conditions. Most PEPs have specific activities in the range of 5-50 units/mg protein. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1 mg, or 0.5 mg. In combination therapy involving, for example, a PEP+DPP IV or PEP+DCP I, a comparable dose of the two enzymes may be given; however, the ratio will be influenced by the relative stability of the two enzymes toward gastric and duodenal inactivation.

Enzyme treatment of Celiac Sprue is expected to be most efficacious when administered before or with meals. However, since food can reside in the stomach for 0.5-2 h, and the primary site of action is expected to be in the small intestine, the enzyme could also be administered within 1 hour after a meal.

Optimal gluten detoxification in vivo can also be achieved by combining an appropriate gastric protease with a PEP that acts upon gluten peptides in the duodenum, in concert with pancreatic enzymes. This can be achieved by co-administration of two enzyme doses, e.g. two capsules/tablets; via co-formulation of the two enzymes in appropriate quantities; etc. Lyophilized duodenal PEP particles or granules can be protected by a suitable polymeric enteric coating that promotes enzyme release only in the duodenum. In contrast, release of the gastric protease will be initiated immediately upon consumption of the dosage form. Combination treatment involving a PEP and a complementary therapeutic agent, such as an inhibitor of the enzyme tissue transglutaminase, is also provided.

In some embodiments of the invention, formulations comprise a cocktail of selected proteases. Such combinations may achieve a greater therapeutic efficacy. In one combination formulation, *Flavobacterium* PEP and *Myxococcus* PEP are co-formulated or co-adminstered, to allow for the destruction of a broader range of gluten antigenic peptides. Similarly, combination therapy with one or two PEPs from the above list with an acid-stable PEP or glutamine endoprotease can lead to more efficient gluten proteolysis in the stomach, thereby simplifying the task of gluten assimilation in the upper small intestine.

In another embodiment, the formulation or administration protocol combines a protease product and an inhibitor of transglutaminase 2 (TG2). Such formulations may have additional protection from gluten mediated enteropathy, as TG2 has been shown to have a significant pro-inflammatory effect on gluten peptides in the celiac gut. In particular, TG2 inhibitors containing halo-dihydroisoxazole, diazomethylketone or dioxoindole moieties are useful for this purpose.

In another embodiment, the protease or protease cocktail is administered and/or formulated with an anti-inflammatory agent, e.g. a statin; p38 MAP kinase inhibitor; anti-TNFα agent; etc.

Those of skill will readily appreciate that dose levels can vary as a function of the specific enzyme, the severity of the symptoms and the susceptibility of the subject to side effects. Some of the glutenases are more potent than others. Preferred dosages for a given enzyme are readily determinable by those of skill in the art by a variety of means. A preferred means is to measure the physiological potency of a given compound.

Other formulations of interest include formulations of DNA encoding glutenases of interest, so as to target intestinal cells for genetic modification. For example, see U.S. Pat. No. 6,258,789, herein incorporated by reference, which discloses the genetic alteration of intestinal epithelial cells.

The methods of the invention are used to treat foods to be consumed or that are consumed by individuals suffering from Celiac Sprue and/or dermatitis herpetiformis by delivering an effective dose of glutenase. If the glutenase is administered directly to a human, then the active agent(s) are contained in a pharmaceutical formulation. Alternatively, the desired effects can be obtained by incorporating glutenase into food products or by administering live organisms that express glutenase, and the like. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ(a1*0301, b1*0302)] are indicative of a susceptibility to the disease.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

This application is related to U.S. Provisional 60/565,668, filed April 26, 2004; to U.S. Provisional application 60/357,238 filed Feb. 14, 2002; to U.S. Provisional Application 60/380,761 filed May 14, 2002; to U.S. Provisional Application 60/392,782 filed Jun. 28, 2002; and to U.S. Provisional application No. 60/422,933, filed Oct. 31, 2002, to U.S. Provisional Application 60/428,033, filed Nov. 20, 2002, to U.S. Provisional Application 60/435,881, filed Dec. 20, 2002, and to U.S. Ser. No. 10/367,405, filed Feb. 14, 2004, each of which are herein specifically incorporated by reference.

EXAMPLES

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Detection of Immunodominant Peptides from Gliadin and Enzymes that Degrade Them

The following examples describe the discovery and characterization of a small number of immunodominant peptides from gliadin, which account for most of the stimulatory activity of dietary gluten on intestinal and peripheral T lymphocytes found in Celiac Sprue patients. The proteolytic kinetics of these immunodominant peptides were analyzed at the small intestinal surface. Brush border membrane vesicles from adult rat intestines were used to show that these proline-glutamine-rich peptides are exceptionally resistant to enzymatic processing, and that dipeptidyl peptidase IV and dipeptidyl carboxypeptidase are the rate-limiting enzymes in their digestion. Supplementation of the brush border membrane with trace quantities of a bacterial prolyl endopeptidase leads to rapid destruction of these gliadin peptides. These results provide the basis for enzyme-mediated therapies for treating food for provision to Celiac Sprue patients, and for treating such patients directly that offer distinct advantages over the only current therapeutic option, which is strict exclusion of gluten containing food.

To investigate the digestion of gluten, liquid chromatography coupled mass spectroscopy analysis (LC-MS-MS) was utilized to investigate the pathways and associated kinetics of hydrolysis of immunodominant gliadin peptides treated with rat BBM preparations. Because the rodent is an excellent small animal model for human intestinal structure and function, rat BBM was chosen as a suitable model system for these studies.

BBM fractions were prepared from rat small intestinal mucosa as described in Ahnen et al. (1982) *J. Biol. Chem.* 257, 12129-35. The specific activities of the known BB peptidases were determined to be 127 µU/g for Aminopeptidase N (APN, EC 3.4.11.2), 60 µU/g for dipeptidyl peptidase IV (DPP IV, EC 3.4.14.5), and 41 µU/µg for dipeptidyl carboxypeptidase (DCP, EC 3.4.15.1) using standard assays. No proline aminopeptidase (EC 3.4.11.5) or prolyl endopeptidase activity (PEP, EC 3.4.21.26) activity was detectable (<5 µU/µg). Alkaline phosphatase and sucrase were used as control BBM enzymes with activities of 66 µU/g and 350 µU/µg, respectively.

BBM fractions were partially purified from the small intestinal mucosa of adult female rats maintained on an ad libitum diet of wheat-based standard rodent chow. Total protein content was determined by a modified method of Lowry with BSA as a standard. Alkaline phosphatase activity was determined with nitrophenyl phosphate. Sucrase activity was measured using a coupled glucose assay. DPP IV, proline aminopeptidase and APN were assayed continuously at 30° C. in 0.1M Tris-HCl, pH 8.0, containing 1 mM of the p-nitroanilides ($\epsilon$=8,800 $M^{-1}$ $cm^{-1}$) Gly-Pro-pNA, Pro-pNA or Leu-pNA, the latter in additional 1% DMSO to improve solubility.

DCP activity was measured in a 100 μl reaction as the release of hippuric acid from Hip-His-Leu. PEP activity was determined continuously with 0.4 mM Z-Gly-Pro-pNA in PBS:H$_2$O:dioxane (8:1.2:0.8) at 30° C. One unit is the consumption of 1 μmol substrate per minute.

DPP IV and DCP are both up-regulated by a high proline content in the diet. However, APN activity using standard substrates was found to be higher than DPP IV even when fed extreme proline rich diets. Also, although a higher DCP vs. CPP activity has been observed with the model peptide Z-GPLAP at saturating concentrations, a difference in Km values could easily account the reversed ratio measured. The amount of 100 μM was chosen as the initial peptide concentration, because non-saturating kinetics ($k_{cat}/K_m$) were considered to be physiologically more relevant than the maximal rates of hydrolysis ($k_{cat}$).

Proteolysis with the BBM preparation was investigated using the peptide (SEQ ID NO:1) QLQPFPQPQLPY, a product of chymotryptic digestion of α-9 gliadin (Arentz-Hansen et al. (2000) *J. Exp. Med.* 191, 603-12). This peptide has been shown to stimulate proliferation of T cells isolated from most Celiac Sprue patients, and hence is considered to possess an immunodominant epitope. It was subjected to BBM digestion, followed by LC-MS-MS analysis. A standard 50 μl digestion mixture contained 100 μM of synthetic peptide, 10 μM tryptophan and Cbz-tryptophan as internal standards, and resuspended BBM preparations with a final protein content of 27 ng/μl and exogenous proteins, as indicated, in phosphate buffered saline. After incubation at 37° C. for the indicated time, the enzymes were inactivated by heating to 95° C. for 3 minutes. The reaction mixtures were analyzed by LC-MS (SpectraSystem, ThermoFinnigan) using a C18 reversed phase column (Vydac 218TP5215, 2.1×150 mm) with water:acetonitrile:formic acid (0.1%):trifluoroacetic acid (0.025%) as the mobile phase (flow: 0.2 ml/min) and a gradient of 10% acetonitrile for 3 minutes, 10-20% for 3 minutes, 20-25% for 21 minutes followed by a 95% wash. Peptide fragments in the mass range of m/z=300-2000 were detected by electrospray ionization mass spectroscopy using a LCQ ion trap and their identities were confirmed by MSMS fragmentation patterns.

While the parent peptide (SEQ ID NO:1) QLQPF-PQPQLPY disappeared with an apparent half life of 35 min, several intermediates were observed to accumulate over prolonged periods (FIG. 1A). The MS intensities (m/z=300-2000 g/mol) and UV$_{280}$ absorbances of the parent peptides (SEQ ID NO:1) QLQPFPQPQLPY and (SEQ ID NO:3) PQPQLPYPQPQLPY were found to depend linearly on concentration in the range of 6-100 μM. The reference peptides (SEQ ID NO:4) PQPQLPYPQPQLP, (SEQ ID NO:5) QLQPFPQPQLP, (SEQ ID NO:6) QPQFPQPQLPY and (SEQ ID NO:7) QPFPQPQLP were generated individually by limited proteolysis of the parent peptides with 10 μg/ml carboxypeptidase A (C-0261, Sigma) and/or 5.9 μg/ml leucine aminopeptidase (L-5006, Sigma) for 160 min at 37° C. and analyzed by LC-MS as in FIG. 1.

Figure 1B:
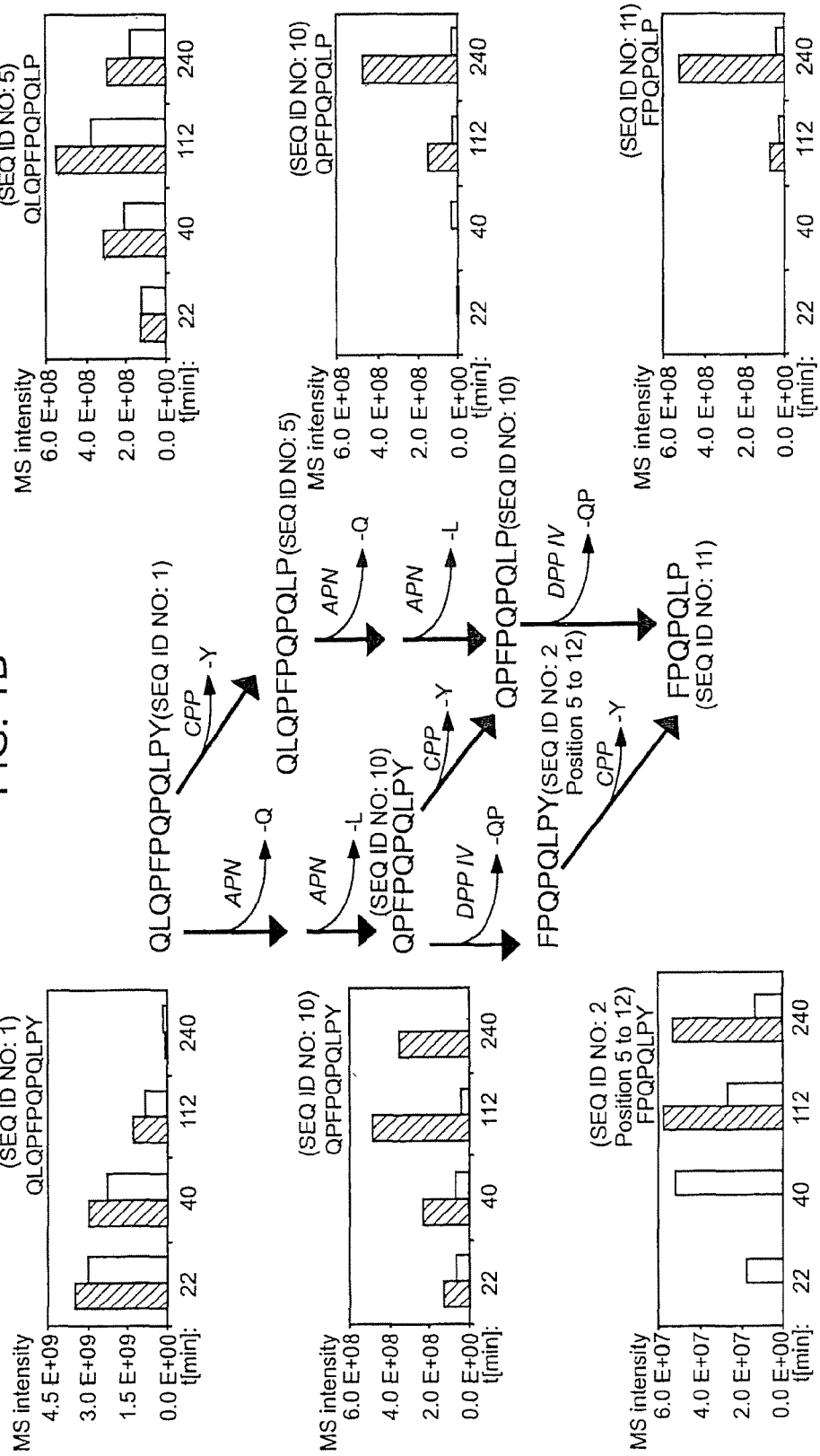

Indeed, the subsequent processing of the peptide was substantially retarded (FIG. 1B). The identities of the major intermediates were confirmed by tandem MS, and suggested an unusually high degree of stability of the (SEQ ID NO:8) PQPQLP sequence, a common motif in T cell stimulating peptides. Based on this data and the known amino acid preferences of the BBM peptidases, the digestive breakdown of (SEQ ID NO:1) QLQPFPQPQLPY was reconstructed, as shown in the insert of FIG. 1B. The preferred pathway involves serial cleavage of the N-terminal glutamine and leucine residues by aminopeptidase N (APN), followed by removal of the C-terminal tyrosine by carboxypeptidase P (CPP) and hydrolysis of the remaining N-terminal QP-dipeptide by DPP IV. As seen in FIG. 1B, the intermediate (SEQ ID NO:6) QPFPQPQLPY (formed by APN attack on the first two N-terminal residues) and its derivatives are increasingly resistant to further hydrolysis. Because the high proline content seemed to be a major cause for this proteolytic resistance, digestion was compared with a commercially available non-proline control peptide (SEQ ID NO:9) RRLIEDNEYTARG (Sigma, St. Louis, Mo.). Initial hydrolysis was much faster ($t_{1/2}$=10 min). More importantly, digestive intermediates were only transiently observed and cleared completely within one hour, reflecting a continuing high specificity of the BBM for the intermediate peptides.

Because the three major intermediate products (SEQ ID NO:10) QPFPQPQLPY, (SEQ ID NO:7) QPFPQPQLP, (SEQ ID NO:11) FPQPQLP) observed during BBM mediated digestion of (SEQ ID NO:1) QLQPFPQPQLPY are substrates for DPP IV, the experiment was repeated in the presence of a 6-fold excess activity of exogenous fungal DPP IV. Whereas the relatively rapid decrease of the parent peptide and the intermediate levels of (SEQ ID NO:5) QLQPF-PQPQLP were largely unchanged, the accumulation of DPP IV substrates was entirely suppressed, and complete digestion was observed within four hours. (FIG. 1B, open bars).

Figures 2A, 2B:
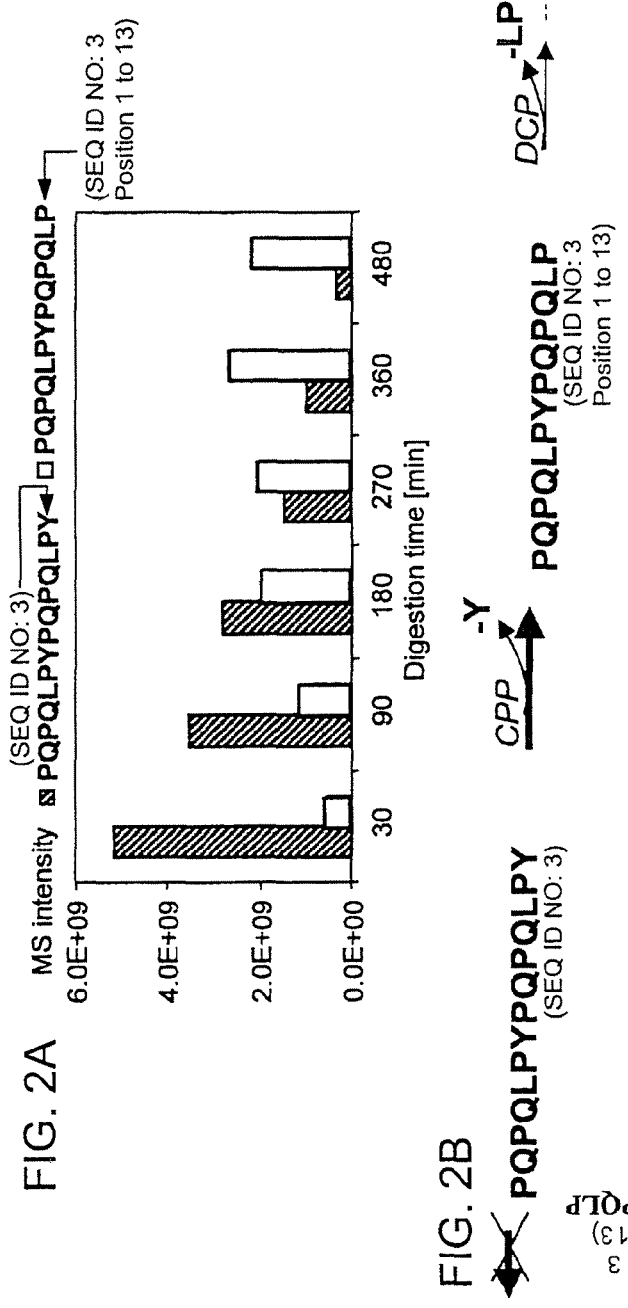
FIG. 2A-2B. C-terminal digestion of the immunodominant gliadin peptide by brush border membrane.

To investigate the rate-limiting steps in BBM mediated digestion of gliadin peptides from the C-terminal end, another known immunodominant peptide derived from wheat α-gliadin, (SEQ ID NO:3) PQPQLPYPQPQLPY, was used. Although peptides with N-terminal proline residues are unlikely to form in the small intestine (none were observed during BBM digestion of (SEQ ID NO:1) QLQPFPQPQLPY, FIG. 1A), they serve as a useful model for the analysis of C-terminal processing, because the N-terminal end of this peptide can be considered proteolytically inaccessible due to minimal proline aminopeptidase activity in the BBM. As shown in FIG. 2, this peptide is even more stable than (SEQ ID NO:1) QLQPFPQPQLPY. In particular, removal of the C-terminal tyrosine residue by carboxypeptidase P (CPP) is the first event in its breakdown, and more than four times slower than APN activity on (SEQ ID NO:1) QLQPF-PQPQLPY (FIG. 1B). The DCP substrate (SEQ ID NO:4) PQPQLPYPQPQLP emerges as a major intermediate following carboxypeptidase P catalysis, and is highly resistant to further digestion, presumably due to the low level of endogenous DCP activity naturally associated with the BBM. To confirm the role of DCP as a rate-limiting enzyme in the C-terminal processing of immunodominant gliadin peptides, the reaction mixtures were supplemented with rabbit lung DCP. Exogenous DCP significantly reduced the accumulation of (SEQ ID NO:4) PQPQLPYPQPQLP after overnight incubation in a dose dependent manner. Conversely, the amount of accumulated (SEQ ID NO:4) PQPQLPYPQPQLP increased more than 2-fold in the presence of 10 μM of captopril, a DCP-specific inhibitor, as compared with unsupplemented BBM.

Together, the above results demonstrate that (i) immunodominant gliadin peptides are exceptionally stable toward breakdown catalyzed by BBM peptidases, and (ii) DPP IV and especially DCP are rate-limiting steps in this breakdown process at the N- and C-terminal ends of the peptides, respectively. Because BBM exopeptidases are restricted to N- or C-terminal processing, it was investigated if generation of additional free peptide ends by pancreatic enzymes would accelerate digestion. Of the pancreatic proteases tested, only elastase at a high (non-physiological) concentration of 100 ng/μl was capable of hydrolyzing (SEQ ID NO:3) PQPQLPYPQPQ↓LPY. No proteolysis was detected with trypsin or chymotrypsin.

Figure 3:
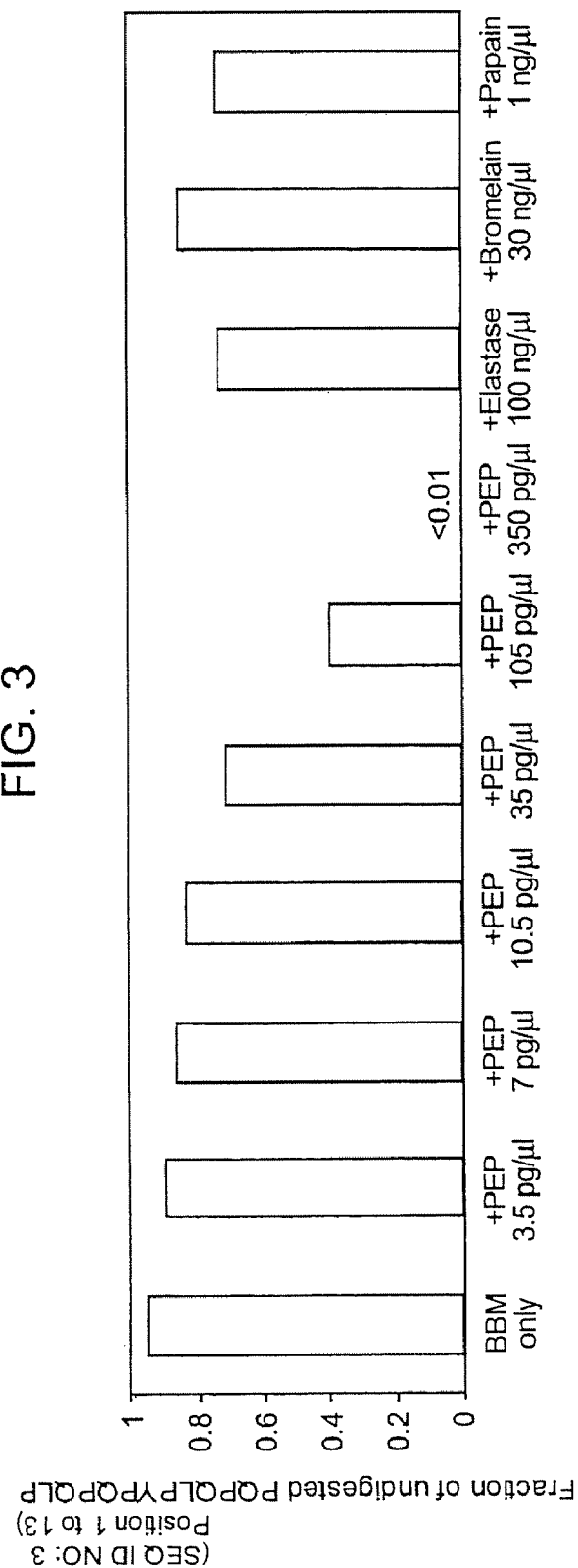
FIG. 3. Dose dependent acceleration of brush border mediated digestion by exogenous endoproteases. As seen from FIG. 2A-2B, the peptide (SEQ ID NO:4) PQPQLPYPQPQLP is stable toward further digestion. This peptide was digested with 27 ng/µl brush border membranes, either alone, with increasing amounts of exogenous prolyl endopeptidase (PEP, specific activity 28 µU/pg) from Flavobacterium meningosepticum (US Biological, MA), or with additional elastase (E-1250, Sigma, Mo.), bromelain (B-5144, Sigma, Mo.) or papain (P-5306, Sigma, Mo.) (12). After one hour, the fraction of remaining (SEQ ID NO:4) PQPQLPYPQPQLP (compared to the initial amount at t=0 min) was analyzed and quantified as in FIG. 1.

Alerted by the high proline content as a hallmark of most immunogenic gliadin peptides, a proline-specific endopeptidase was tested for the generation of new, free peptide termini. A literature search on available proteases led to the identification of prolyl endopeptidase (PEP) from *Flavobacterium meningosepticum*, which is specific for the C-terminal cleavage of prolines and readily available from recombinant sources (Yoshimoto et al. (1991) *J. Biochem.* 110, 873-8). The stable (SEQ ID NO:4) PQPQLPYPQPQLP intermediate was digested with BBM in the presence of exogenous PEP. FIG. 3 shows the dose dependent acceleration of (SEQ ID NO:4) PQPQLPYPQPQLP digestion with increasing PEP concentration. As little as 3.5 pg PEP/27 ng BBM protein was sufficient to double the extent of proteolysis of this gliadin fragment compared to incubation with BBM alone. In comparison, other commonly used proteases like papain, bromelain or porcine elastase were much less efficient, requiring 30-fold (papain) or 3000-fold (bromelain, elastase) higher amounts of enzyme compared to PEP to give similar results. Their proteolysis was restricted to the cleavage of the $Gln^4$-$Leu^5$ and/or $Gln^{11}$-$Leu^{12}$ bonds.

Prolyl endopeptidase (EC 3.4.21.26) had a preference for the $Pro^8$-$Gln^9$ and to a lesser extent the $Pro^6$-$Tyr^7$ bond of the (SEQ ID NO:4) PQPQLP↓YP↓QPQLP peptide. A similar preferential cleavage was found for (SEQ ID NO:1) QLQPFP↓QPQLPY. This is in agreement with the preference of this prolyl endopeptidase for a second proline in the S2' position (Bordusa and Jakubke (1998) *Bioorg. Med. Chem.* 6, 1775-80). Based on this P↓XP motif and on the present data, up to 16 new, major cleavage sites can be predicted in the α2-gliadin sequence, a major source of immunodominant epitopes identified thus far upon PEP treatment. All of them are located in the critical N-terminal part. The internal cleavage by PEP can be expected to generate additional (otherwise inaccessible) substrates for DPP IV and DCP thereby complementing the natural assimilation process of gliadins by the BBM. Thus, the specificity of prolyl endopeptidase is ideally suited for detoxification of persistent immunoactive gliadin peptides in Celiac Sprue.

The above data demonstrates that proline-rich gliadin peptides are extraordinarily resistant to digestion by small intestinal endo- and exopeptidases, and therefore are likely to accumulate at high concentrations in the intestinal cavity after a gluten rich meal. The pathological implication of digestive resistance is strengthened by the observed close correlation of proline content and celiac toxicity as observed in the various common cereals (Schuppan (2000) *Gastroenterology* 119, 234-42). This analysis of the digestive pathways of immunodominant peptides also provides a mechanism for determining whether enzymes capable of accelerating this exceptionally slow process can be therapeutically useful in the Celiac Sprue diet.

Addition of exogenous DPP IV and DCP can compensate for the intrinsically slow proline processing by the BBM, although both enzymes rely on efficient generation of free N- and C-termini by endoproteolytic cleavage. In a preferred embodiment, a soluble bacterial prolyl endopeptidase (PEP) is used, which was shown to be extremely efficient at hydrolyzing the proline-rich gliadin fragments. Although PEP is expressed in human brain, lung, kidney and intestine, no such activity has been reported in the brush border.

Supplementation of the Celiac Sprue diet with bioavailable PEP (with or without DPP IV and/or DCP), by virtue of facilitating gliadin peptide cleavage to non-toxic and/or digestible fragments, is useful in attenuating or eliminating the inflammatory response to gluten. Such a treatment regimen is analogous to the enzyme therapy treatment used to treat lactose intolerance, where orally administered lactase is effective in cleaving and thereby detoxifying the lactose in milk products. Prolyl endopeptidases are widely distributed in microorganisms, plants and animals and have been cloned from *Aeromonas hydrophyla* (Kanatani et al. (1993) *J. Biochem.* 113, 790-6); *Pyrococcus furious* (Robinson et al. (1995) Gene 152, 103-6) and from pig brain (Rennex et al. (1991) *Biochemistry* 30, 2195-2030). These isozymes constitute alternative detoxifying peptidases. Furthermore, the prolyl endopeptidase used in this study is readily amenable to protein engineering by directed evolution. Thus, optimization of PEP specificity towards immunogenic gliadin peptides can be achieved.

Example 2

Further Characterization of Immunodominant Gliadin Peptides and Means for Their Digestion It has long been known that the principal toxic components of wheat gluten are a family of closely related Pro-Gln rich proteins called gliadins. Peptides from a short segment of α-gliadin appear to account for most of the gluten-specific recognition by CD4+ T cells from Celiac Sprue patients. These peptides are substrates of tissue transglutaminase (tT-Gase), the primary auto-antigen in Celiac Sprue, and the products of this enzymatic reaction bind to the class II HLA DQ2 molecule. This example describes a combination of in vitro and in vivo animal and human studies used to characterize this "immunodominant" region of α-gliadin as part of an unusually long proteolytic product generated by the digestive process that: (a) is exceptionally resistant to further breakdown by gastric, pancreatic and intestinal brush border proteases; (b) is the highest specificity substrate of human tissue transglutaminase (tTGase) discovered to date; (c) contains at least six overlapping copies of epitopes known to be recognized by patient derived T cells; (d) stimulates representative T cell clones that recognize these epitopes with sub-micromolar efficacy; and (e) has homologs in proteins from all toxic foodgrains but no homologs in non-toxic foodgrain proteins. In aggregate, these findings demonstrate that the onset of symptoms upon gluten exposure in the Celiac Sprue patient can be traced back to a small segment of α-gliadin. Finally, it is shown that this "super-antigenic" long peptide can be detoxified in vitro and in vivo by treatment with bacterial prolyl endopeptidase, providing a peptidase therapy for Celiac Sprue.

Identification of stable peptides from gastric protease, pancreatic protease and brush border membrane peptidase catalyzed digestion of recombinant α2-gliadin: The protein α2-gliadin, a representative α-gliadin (Arentz-Hansen et al. (2000) Gut 46:46), was expressed in recombinant form and purified from *E. coli*. The α2-gliadin gene was cloned in pET28a plasmid (Novagen) and transformed into the expression host BL21 (DE3) (Novagen). The transformed cells were grown in 1-liter cultures of LB media containing 50 μg/ml of kanamycin at 37° C. until the OD600 0.6-1 was achieved. The expression of α2-gliadin protein was induced with the addition of 0.4 mM isopropyl β-D-thiogalactoside (Sigma) and the cultures were further incubated at 37° C. for 20 hours. The cells expressing the recombinant α2-gliadin were centrifuged at 3600 rpm for 30 minutes. The pellet was resuspended in 15 ml of disruption buffer (200 mM sodium phosphate; 200 mM NaCl; 2.5 mM DTT; 1.5 mM benzamidine; 2.5 mM EDTA; 2 mg/L pepstatin; 2 mg/L leupeptin; 30% v/v glycerol) and lysed by sonication (1 minute; output control set to 6). After centrifugation at 45000 g for 45 min, the supernatant was discarded and the pellet containing gliadin protein was resuspended in 50 ml of 7 M urea in 50 mM Tris (pH=8.0). The suspension was again centrifuged at 45000 g for 45 min and the supernatant was harvested for purification. The supernatant containing α2-gliadin was incubated with 1 ml of nickel-nitrilotriacetic acid resin (Ni-NTA; Qiagen) overnight and then batch-loaded on a column with 2 ml of Ni-NTA. The column was washed with 7M urea in 50 mM Tris (pH=8.0), and α2-gliadin was eluted with 200 mM imidazole, 7 M urea in 50 mM Tris (pH=4.5). The fractions containing α2-gliadin were pooled into a final concentration of 70% ethanol solution and two volumes of 1.5M NaCl were added to precipitate the protein. The solution was incubated at 4° C. overnight and the final precipitate was collected by centrifugation at 45000 g for 30 min, rinsed in water, and re-centrifuged to remove the urea. The final purification step of the α-2 gliadin was developed with reverse-phase HPLC. The Ni-NTA purified protein fractions were pooled in 7 M urea buffer and injected to a Vydac (Hesperia, Calif.) polystyrene reverse-phase column (i.d. 4.6 mm×25 cm) with the starting solvent (30% of solvent B: 1:1 HPLC-grade acetonitrile/isopropanol: 0.1% TFA). Solvent A was an aqueous solution with 0.1% TFA. The separation gradient extended from 30-100% of solvent B over 120 min at a flow rate of 0.8 ml/min.

TABLE 2

| Amount of Peptides Digested after 15 hours | | | |
|---|---|---|---|
| | 33-mer | Control A | Control B |
| H1P0 | <20% | >90% | >90% |
| H2P0 | <20% | >61% | >85% |
| H3P0 | <20% | >87% | >95% |
| H4P0 | <20% | >96% | >95% |
| H5P0 | <20% | >96% | >95% |

The purity of the recombinant gliadin was >95%, which allowed for facile identification and assignment of proteolytic products by LC-MS/MS/UV. Although many previous studies utilized pepsin/trypsin treated gliadins, it was found that, among gastric and pancreatic proteases, chymotrypsin played a major role in the breakdown of α2-gliadin, resulting in many small peptides from the C-terminal half of the protein and a few longer (>8 residues) peptides from the N-terminal half, the most noteworthy being a relatively large fragment, the 33-mer (SEQ ID NO:12) LQLQPF-PQPQLPYPQPQLPYPQPQLPYPQPQPF (residues 57-89). This peptide was of particular interest for two reasons: (a) whereas most other relatively stable proteolytic fragments were cleaved to smaller fragments when the reaction times were extended, the 33-mer peptide remained intact despite prolonged exposure to proteases; and (b) three distinct patient-specific T cell epitopes identified previously are present in this peptide, namely, (SEQ ID NO:20) PFPQPQLPY, (SEQ ID NO:21) PQPQLPYPQ (3 copies), and (SEQ ID NO:22) PYPQPQLPY (2 copies).

Figure 4:
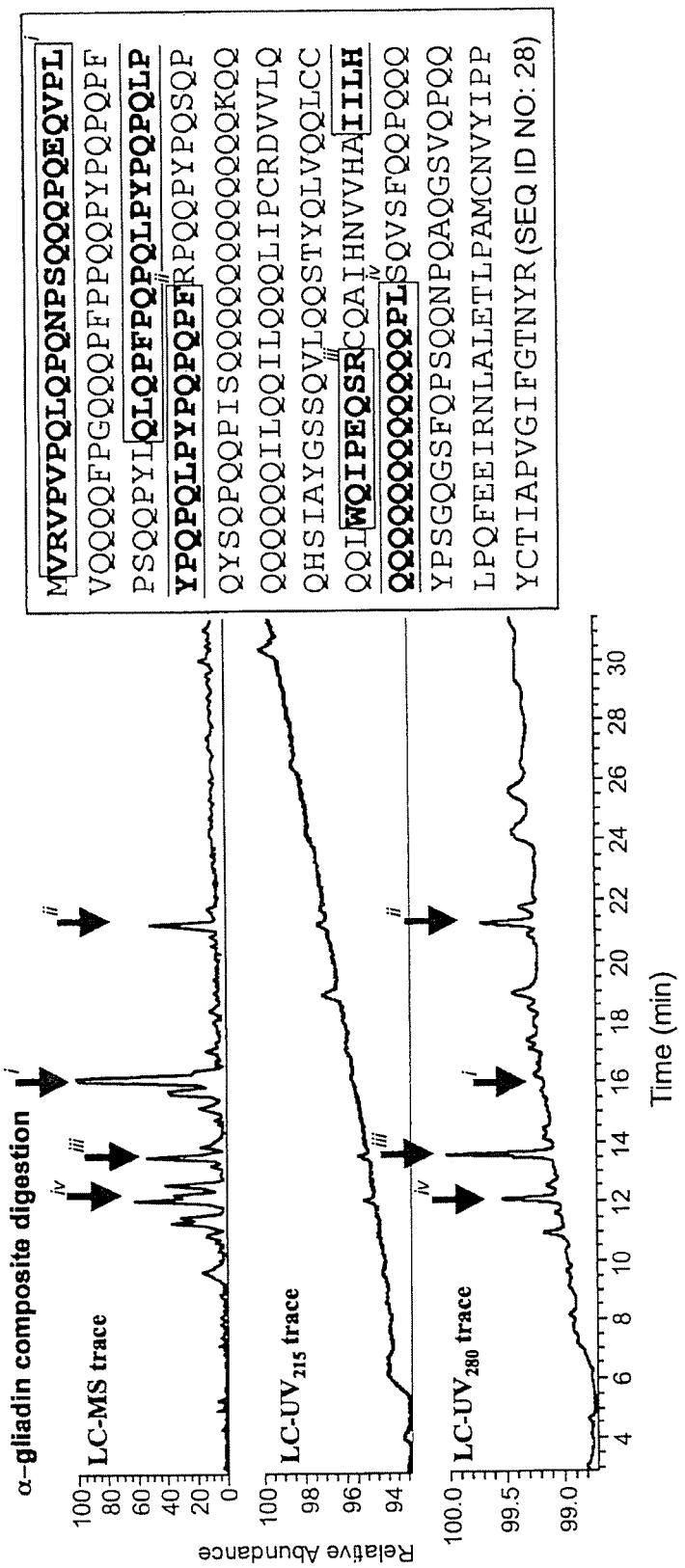
FIG. 4. Products of gastric and pancreatic protease mediated digestion of α2-gliadin under physiological conditions. Analysis was performed by LC-MS. The longest peptides are highlighted by arrows and also in the sequence of α2-gliadin (inset).

To establish the physiological relevance of this peptide, composite gastric/pancreatic enzymatic digestion of α2 gliadin was then examined. As expected, enzymatic digestion with pepsin (1:100 w/w ratio), trypsin (1:100), chymotrypsin (1:100), elastase (1:500) and carboxypeptidase (1:100) was quite efficient, leaving behind only a few peptides longer than 9 residues (the minimum size for a peptide to show class II MHC mediated antigenicity) (FIG. 4). In addition to the above-mentioned 33-mer, the peptide (SEQ ID NO:23) WQIPEQSR was also identified, and was used as a control in many of the following studies. The stability of the 33-mer peptide can also be appreciated when comparing the results of a similar experiment using myoglobin (another common dietary protein). Under similar proteolytic conditions, myoglobin is rapidly broken down into much smaller products. No long intermediate is observed to accumulate.

The small intestinal brush-border membrane (BBM) enzymes are known to be vital for breaking down any remaining peptides from gastric/pancreatic digestion into amino acids, dipeptides or tripeptides for nutritional uptake. Therefore a comprehensive analysis of gliadin metabolism also required investigations into BBM processing of gliadin peptides of reasonable length derived from gastric and pancreatic protease treatment. BBM fractions were prepared from rat small intestinal mucosa. The specific activities of known BBM peptidases were verified to be within the previously reported range. Whereas the half-life of disappearance of WQIPEQSR was ~60 min. in the presence of 12 ng/μl BBM protein, the half-life of (SEQ ID NO:12) LQLQPF-PQPQLPYPQPQLPYPQPQLPYPQPQPF digestion was >20 h. Therefore, the latter peptide remains intact throughout the digestive process in the stomach and upper small intestine, and is poised to act as a potential antigen for T cell proliferation and intestinal toxicity in genetically susceptible individuals.

Verification of proteolytic resistance of the 33-mer gliadin peptide with brush border membrane preparations from human intestinal biopsies: to validate the conclusions reached as described in Example 1, which describes studies with rat BBM preparations, in the context of human intestinal digestion, BBM preparations were prepared from a panel of adult human volunteers, one of whom was a Celiac Sprue patient in remission, while the rest were found to have normal intestinal histology. (SEQ ID NO:12) LQLQPFPQPQLPYPQPQL PYPQPQLPYPQPQPF, (SEQ ID NO:1) QLQPFPQPQLPY (an internal sequence from the 33-mer used as a control), WQIPEQSR and other control peptides (100 μM) were incubated with BBM prepared from each human biopsy (final aminopeptidase N activity of 13 μU/μl) at 37° C. for varying time periods. While (SEQ ID NO:1) QLQPFPQPQLPY, (SEQ ID NO:23) WQIPEQSR and other control peptides were completely proteolyzed within 1-5 h, the long peptide remained largely intact for at 19 hours. These results confirm the equivalence between the rat and human BBM for the purpose of this study. Moreover, these results indicate that the methods, foodstuffs, and other reagents of the invention can be used in humans not known to have Celiac Sprue to improve digestion and reduce any ill effects of the long peptide.

Figure 5:
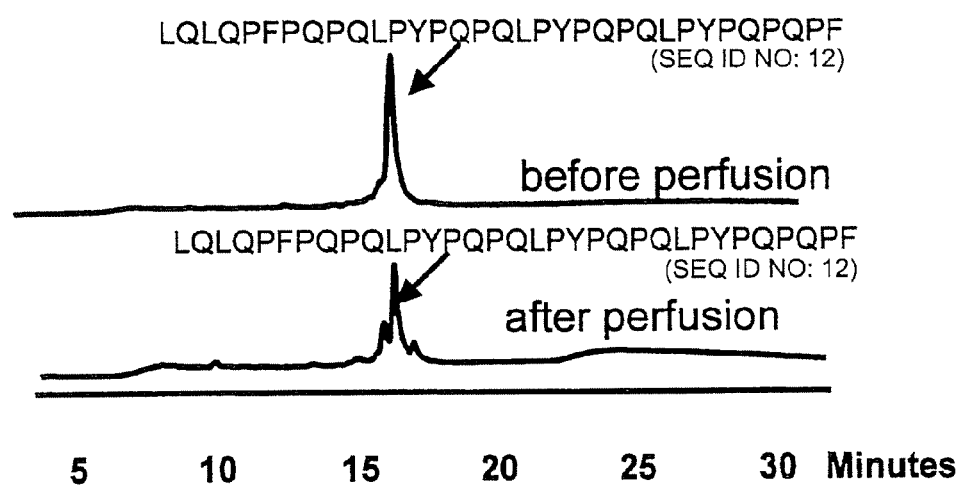
FIG. 5. In vivo brush border membrane digestion of peptides. LC-$UV_{215}$ traces of 25 µM of (SEQ ID NO:12) LQLQPFPQPQLPYPQPQLPYPQPQLPYPQPQPF before perfusion and after perfusion (residence time=20 min). LC-$UV_{215}$ traces of 50 µM of SEQ ID NO:1 QLQPFPQPQLPY before perfusion and after perfusion (residence time=20 min).
Figure 5:
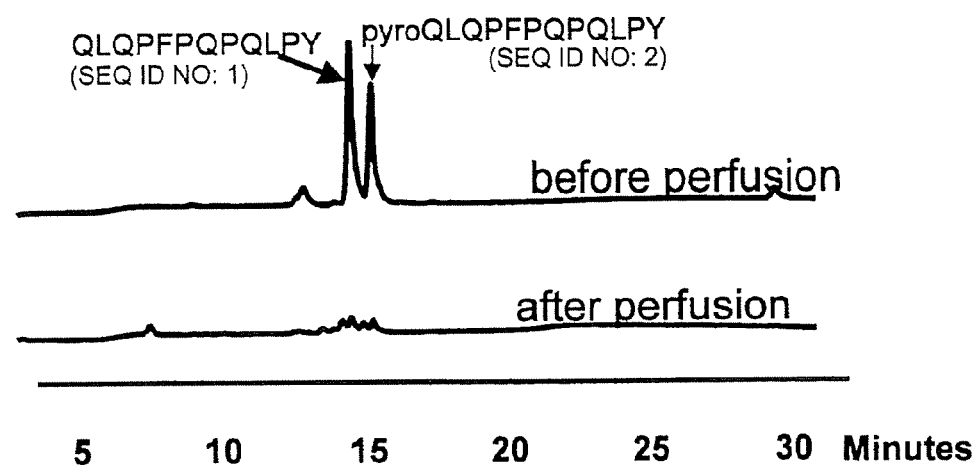

Verification of proteolytic resistance of the 33-mer gliadin peptide in intact animals: The proteolytic resistance of the 33-mer gliadin peptide, observed in vitro using BBM from rats and humans, was confirmed in vivo using a perfusion protocol in intact adult rats (Smithson and Gray (1977) *J. Clin. Invest* 60:665). Purified peptide solutions were perfused through a 15-20 cm segment of jejunum in a sedated rat with a residence time of 20 min, and the products were collected and subjected to LC-MS analysis. Whereas >90% of (SEQ ID NO:1) QLQPFPQPQLPY was proteolyzed in the perfusion experiment, most of the 33-mer gliadin peptide remained intact. These results demonstrate that the 33-mer peptide is very stable as it is transported through the mammalian upper small intestine. The data is shown in FIG. 5.

The 33-mer gliadin peptide is an excellent substrate for tTGase, and the resulting product is a highly potent activator of patient-derived T cells: studies have demonstrated that regiospecific deamidation of immunogenic gliadin peptides by tTGase increases their affinity for HLA-DQ2 as well as the potency with which they activate patient-derived gluten-specific T cells. It has been shown that the specificity of tTGase for certain short antigenic peptides derived from gliadin is higher than its specificity toward its physiological target site in fibronectin; for example, the specificity of tTGase for the α-gliadin derived peptide (SEQ ID NO:3) PQPQLPYPQPQLPY is 5-fold higher than that for its target peptide sequence in fibrinogen, its natural substrate. The kinetics and regiospecificity of deamidation of the 33-mer α-gliadin peptide identified as above were therefore measured. The $k_{cat}/K_M$ was higher than that reported for any peptide studied thus far: kcat/KM=440 min-1 mM-1 for (SEQ ID NO:12) LQLQPFPQPQLPYPQPQLPYPQPQLPYPQPQPF compared to kcat/KM=82 min-1 mM-1 for PQPQLPY and kcat/KM=350 min-1 mM-1 for (SEQ ID NO:3) PQPQLPYPQPQLPY.

Moreover, LC-MS-MS analysis revealed that the peptide (SEQ ID NO:12) LQLQPFPQPQLPYPQPQLPYPQPQLPYPQPQPF was selectively deamidated by tTGase at the underlined residues. Because tTGase activity is associated with the brush border membrane of intestinal enterocytes, it is likely that dietary uptake of even small quantities of wheat gluten will lead to the build-up of sufficient quantities of this 33-mer gliadin peptide in the intestinal lumen so as to be recognized and processed by tTGase.

Figure 6:
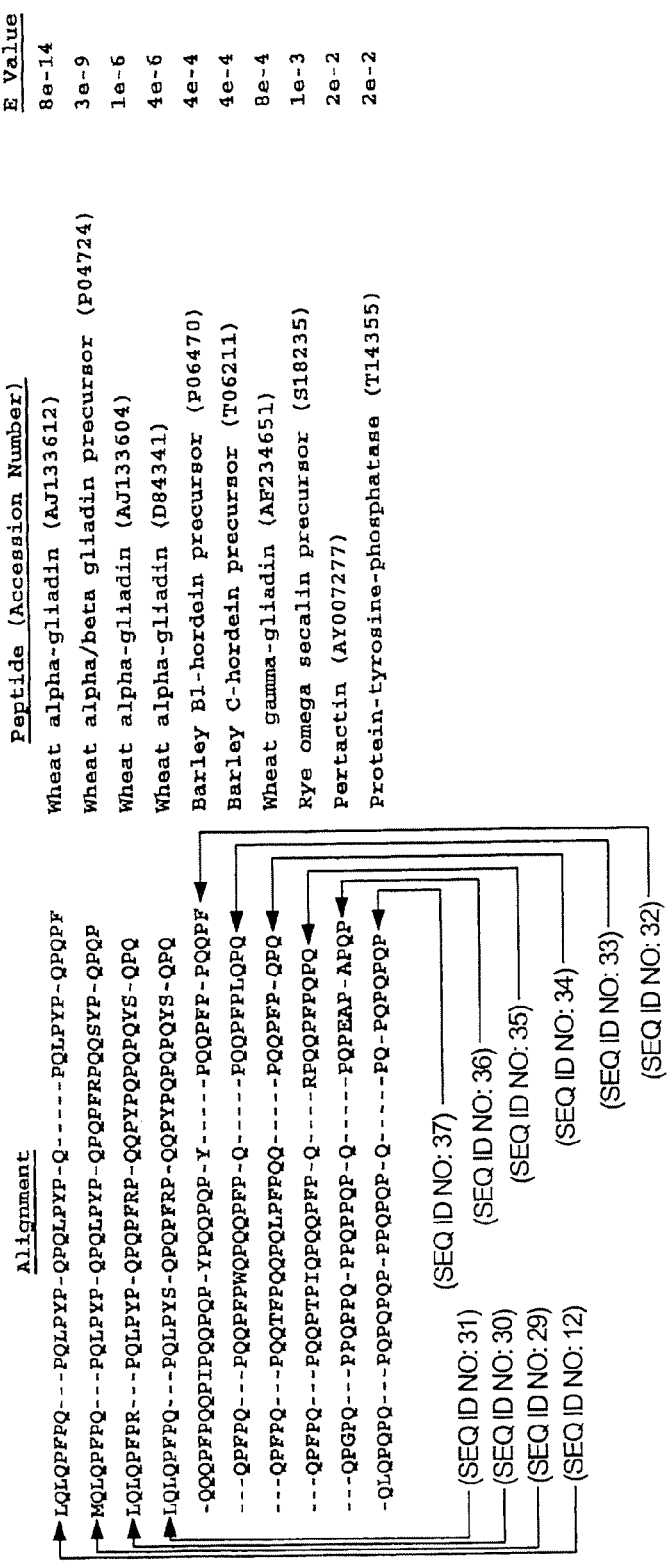
FIG. 6. Alignment of representative gluten and non-gluten peptides homologous to (SEQ ID NO:12) LQLQPF-PQPQLPYPQPQLPYPQPQLPYPQPQPF.

Structural characteristics of the 33-mer gliadin peptide and its naturally occurring homologs: Sequence alignment searches using BLASTP in all non-redundant protein databases revealed several homologs (E-value<0.001) of the 33-mer gliadin peptide, shown in FIG. 6. Interestingly, foodgrain derived homologs were only found in gliadins (from wheat), hordeins (from barley) and secalins (from rye), all of which have been proven to be toxic to Celiac Sprue patients. Nontoxic foodgrain proteins, such as avenins (in oats), rice and maize, do not contain homologous sequences to the 33-mer gliadin. In contrast, a BLASTP search with the entire □2-gliadin sequence identified foodgrain protein homologs from both toxic and nontoxic proteins. Based on available information regarding the substrate specificities of gastric, pancreatic and BBM proteases and peptidases, it is believed that, although most gluten homologs to the 33-mer gliadin peptide contained multiple proteolytic sites and are therefore unlikely to be completely stable toward digestion, several sequences from wheat, rye and barley are expected to be resistant to gastric and intestinal proteolysis. The stable peptide homologs to the 33-mer α2-gliadin peptide are (SEQ ID NO:24) QPQPFPPQLPYPQTQPFPPQQPYPQPQPQYPQPQ (from α1- and α6-gliadins); (SEQ ID NO:25) QQQPFPQQPIPQQPQPYPQQPQPYPQQPFPPQQPF (from B1 hordein); (SEQ ID NO:26) QPFPQPQQTFPQQPQLPFPQQPQQPFPQPQ (from γ-gliadin); (SEQ ID NO:27) QPFPQPQQPTPIQPQQPFPQRPQQPFPQPQ (from ω-secalin). These stable peptides are all located at the N-terminal region of the corresponding proteins. The presence of proline residues after otherwise cleavable residues in these peptides would contribute to their proteolytic stability.

Figure 7:
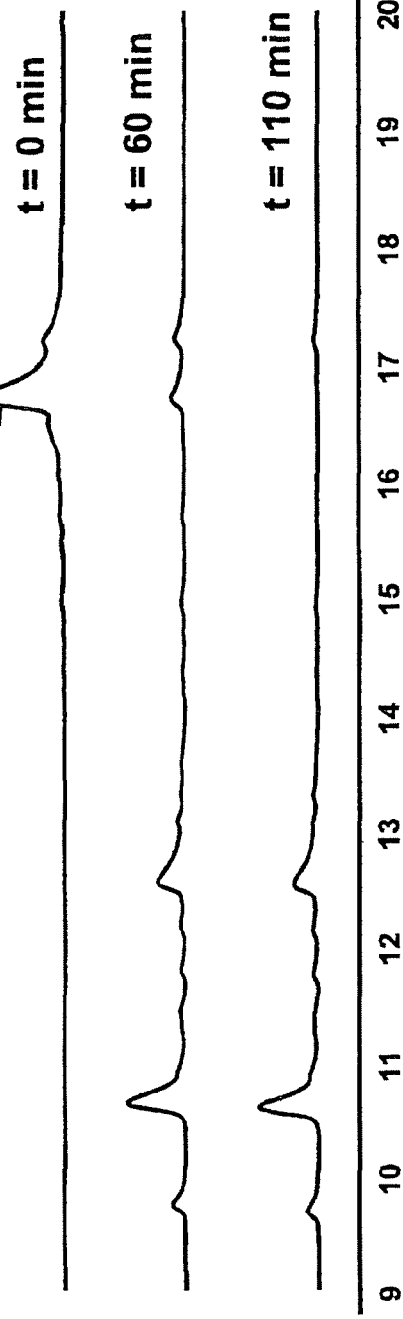
FIG. 7. Breakdown and detoxification of 33-mer gliadin peptide with PEP. In vitro incubation of PEP (540 mU/ml) with the 33-mer gliadin peptide (100 µM) for the indicated time. In vivo digestion of the 33-mer gliadin peptide (25 µM) with PEP (25 mU/ml) and the rat's intestine (residence time=20 min).
Figure 7:
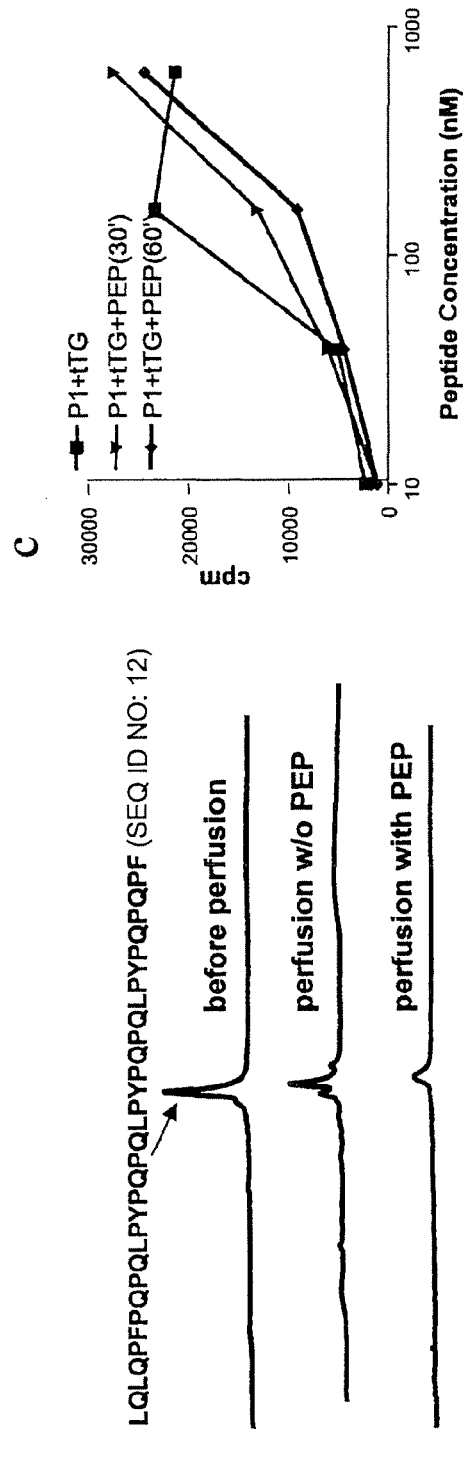

Bacterial prolyl endopeptidase rapidly detoxifies the 33-mer gliadin peptide: The abundance and location of proline residues is a crucial factor contributing to the resistance of the 33-mer gliadin peptide toward gastrointestinal breakdown. In accordance with the methods of the invention, a prolyl endopeptidase can catalyze breakdown of this peptide, thereby diminishing its toxic effects. Preliminary in vitro studies with short gliadin peptides and the prolyl endopeptidase (PEP) from *F. meningosepticum* demonstrate this aspect of the invention. The ability of this PEP to clear the 33-mer gliadin peptide was evaluated via in vitro and in vivo experiments. Using both rat BBM and co-perfusion of the peptide and PEP in intact rat intestines, this detoxification was demonstrated. The results are shown in FIG. 7. Together these results highlight the potential of detoxifying gluten in Celiac Sprue patients by peptidase therapy.

Although gluten proteins from foodgrains such as wheat, rye and barley are central components of a nutritious diet, they can be extremely toxic for patients suffering from Celiac Sprue. To elucidate the structural basis of gluten toxicity in Celiac Sprue, comprehensive proteolytic analysis was performed on a representative recombinant gliadin under physiologically relevant conditions. An unusually long and proteolytically stable peptide product was discovered, whose physiological relevance was confirmed by studies involving brush border membrane proteins from rat and human intestines as well as intestinal perfusion assays in live rats. In aggregate, these data demonstrate that this peptide and its homologs found in other wheat, rye and barley proteins contribute significantly to the inflammatory response to dietary wheat in Celiac Sprue patients.

The absence of satisfactory animal models for Celiac Sprue implies that the pivotal pathogenic nature of the gluten peptides identified in this study can only be verified in human patients. The results above demonstrate that the deleterious effects of gluten ingestion by Celiac Sprue patients can be amelioriated by enzyme treatment of gluten containing foods. Specifically, co-administration of a bioavailable form of a suitable prolyl endopeptidase with dietary gluten attenuate its toxicity by cleaving the stable 33-mer peptide into non-immunogenic products. Given the absence of a satisfactory therapeutic option for Celiac Sprue and the notorious difficulty associated with long-term maintenance of a gluten-free diet, the peptidase therapies of the present invention provides an alternative to strict abstinence for the rapidly growing numbers of individuals affected by this disease.

Example 3

Comparison of PEP Activities

To gain insight into the similarities and differences between naturally occurring prolyl endopeptidases, we have systematically compared the properties of three homologous PEPs from different bacterial sources. Our studies have utilized two known recombinant PEPs from *Flavobacterium meningosepticum* (FM) and *Sphingomonas capsulata* (SC), respectively, and a novel PEP from *Myxococcus xanthus* (MX) that we have expressed for the first time as a heterologous recombinant protein. The enzymatic activities of these PEPs were quantitatively analyzed versus model substrates as well as two gluten-derived peptides with potential relevance to Celiac Sprue pathogenesis. In particular, we have probed the influence of substrate chain length, pH, pancreatic proteases and intestinal brush border peptidases on the activity of each PEP. Both in vivo and ex vivo experiments were performed as part of these studies.

Experimental Procedures

Cloning of PEP Genes. The PEP genes were amplified from the genomic DNA from the corresponding bacterial strains (*F. meningosepticum*: ATCC 13253; *S. capsulata*: ATCC 14666; *M. xanthus*: ATCC 25232). The sequence of the putative MX PEP is available from the NCBI database (Locus ID AAD31004). Oligonucleotides used for PCR amplification included: (SEQ ID NO:37) (1) FM first half: 5'-AAC CAA TCA TAT GAA GTA CAA CAA ACT TTC TGT G (NdeI), (SEQ ID NO:38) 5'-GAT AAA AAC GGA AAG CTT GTA AGG GC (HindIII); FM second half: (SEQ ID NO:39) 5'-GCC CTT ACA AGC TTT CCG TTT TTA TC (HindIII) and (SEQ ID NO:40) 5'-CCC TTA ATT TTC AAA TTT TAG CTC GAG TTT ATG ATT TAT A (SacI); (2) SC first half: (SEQ ID NO:41) 5'-AGG ATA TCC ATA TGA AGA ACC GCT TGT GG (NdeI), (SEQ ID NO:42) 5'-GAC AAC CTC GAA TCC GTC GGC ATT G (HinfI); SC second half: (SEQ ID NO:43) 5'-CAA TGC CGA CGG ATT CGA GGT TGT C (HinfI), (SEQ ID NO:44) 5'-CGC GGG GAC CTC GAG TAG AAA CTG (SacI); (3) MX: (SEQ ID NO:45) 5'-CT CCC CAT ATG TCC TAC CCG GCG ACC (NdeI) and (SEQ ID NO:46) 5'-GTG GCG GCG CAG GGC CGC AAG CTT CCC AAG CG (HindIII). The amplified genes were cloned into a pET28b plasmid (Novagen).

Expression and Purification of PEPs. Expression plasmids were introduced via transformation into BL21 (DE3) cells. Transformants grown at 37° C., and induced in the presence of 100 µM IPTG at 22° C. overnight. Low temperature induction was found to improve the yield of active enzyme. All purification steps were performed at 4° C. unless noted otherwise. Since FM and SC PEP enzymes naturally possess a signal sequence, they are secreted into the periplasmic space of E. coli. A modified osmotic shock protocol (EMD Biosciences, CA) was therefore used to obtain an enriched protein lysate containing either PEP. Cell pellets (4 L of culture) were resuspended in 30 ml of 30 mM Tris-HCl, pH 8, 20% sucrose and 1 mM EDTA, and stirred slowly at room temperature for 10 min. The suspension was centrifuged at 10,000 g for 15 min, and the cell pellet was resuspended in ice-cold dH$_2$O and stirred slowly on ice for 10 min. The shocked cells were then centrifuged again at 40,000-50000 g for 30 min. The supernatant containing the periplasmic proteins was treated for 1-2 h with 1 M NaCl solution (to a final concentration of 300 mM NaCl), 1 M imidazole solution (to a final concentration 5 mM imidazole) and 1 ml of Ni-NTA resin (Qiagen, CA). The crude protein was then loaded onto a column containing additional 1 ml of Ni-NTA resin. After thorough wash steps using the wash buffer (50 mM phosphate, 300 mM NaCl, pH 7.0) with 0-10 mM imidazole, the PEP was eluted with 150 mM imidazole, 50 mM phosphate, 300 mM NaCl, pH 8. FM PEP was further purified on a FPLC system (Amersham Pharmacia, NJ) through a HiTrap-SP cation exchange column. Prior to application on the HiTrap-SP column, the protein was exchanged into 20 mM phosphate buffer (pH 7). Following injection, PEP was eluted with a salt gradient from 20 mM phosphate, pH 7 (buffer A) to 20 mM phosphate, 500 mM NaCl, pH 7 (buffer B) at a flow rate of 1 ml/min. MX PEP, a cytosolic protein, was initially purified from a whole-cell lysate via Ni-NTA affinity chromatography (as detailed above). The protein was further purified on a Superdex 200 gel filtration column (Amersham) with an isocratic gradient of 20 mM HEPES, 2 mM DTT, pH 7.0 at 1 ml/min.

Activity Assays. Post-proline cleavage activity was measured using Z-Gly-Pro-p-nitroanilide and Succinyl-Ala-Pro-p-nitroanilide (Bachem, CA). Z-Gly-Pro-pNA was dissolved in a PBS:water:dioxane (8:1.2:0.8) assay mixture. The concentration of Z-Gly-Pro-pNA was varied from 100-600 µM. Although the substrate Z-Gly-Pro-pNA was effective in detecting enzyme activity, its insolubility at higher concentrations precluded kinetic measurements under substrate-saturated conditions. In contrast, Succinyl-Ala-Pro-pNA, had the advantage of high water solubility at all pH values tested, and was therefore a preferred substrate for kinetic studies.

Hydrolysis of Suc-Ala-Pro-pNA by FM, SC and MX PEPs was monitored in a reaction mixture (300 µl) consisting of 30 µl of 10×PBS buffer, a final concentration of 0.01-0.02 µM enzyme, and Suc-Ala-Pro-pNA (5 mM stock) at final concentrations ranging between 100 µM to 4 mM. The release of the p-nitroanilide was spectrophotometrically detected at a wavelength of 410 nm. The initial velocity of the reaction was determined by the increase in absorbance at 410 nm, which was used to calculate Km and Kcat according to the Michaelis-Menten relationship. For measurement of the influence of pH on the enzyme activity, a series of pH buffer solutions were prepared using citric acid and disodium phosphate for pH values from 3.0 to 6.0, and sodium phosphates for pH values from 7.0 to 8.0. Reaction mixtures (300 µl) consisted of 30 µl of 10× pH buffer, final concentration of 0.01 µM enzyme, and Suc-Ala-Pro-pNA to final concentrations between 100 µM to 4 mM.

pH Stability. The ability to retain enzyme activity after exposure to acidic environments was determined. Hydrochloric acid solutions (10 µl) at pH values ranging from 1.5 to 4.0 were mixed with 1 µl of enzyme for 10-20 min. The acidic mixtures were then neutralized with 40 µl of 10×PBS solution, 60 µl of 5 mM substrate to a final volume of 300 µl. The recovered enzyme activity was measured spectrophotometrically and compared with non-acid treated controls under identical conditions.

Gastric and Pancreatic Protease Stability. In a 96-well U-bottomed plate, 5 µL of 2× reaction buffer (40 mM Na$_2$HPO$_4$, pH=6.5 for pancreatic enzymes or 20 mM HCl for pepsin) was placed, and 1 µL of the degrading enzyme (either 1 mg/ml pepsin or a cocktail of 1 mg/ml trypsin, 1 mg/ml chymotrypsin, 0.2 mg/ml elastase and 0.2 mg/ml carboxypeptidase A) followed by 4 µL of PEP (5-10 U/ml) were added. The plate was incubated at 37° C. for various times (e.g. 0, 5, 10, 20 and 30 min), with 190 µL of PEP substrate solution (2 µl Z-Gly-Pro-p-nitroanilide (16.8 mg/ml in dioxane) 14 µl dioxane, 24 µl water, 150 µl 10 mM PBS buffer, pH=7.5) added to each well. Absorption was measured at 410 nm for 1 to 2 min every 10 s to assay residual activity. Each buffer also contained 5 mg/ml gluten. Untreated gluten was used for pepsin, whereas gluten previously proteolyzed with pepsin (0.01 M HCl, pH=2.0, 1:50 w/w, 2 h, 37° C.) was used for all other enzymes. Wells containing acid (pH=2.0) were neutralized by addition of 10 µL 0.1 M NaOH before addition of the PEP substrate. Enzyme activities are expressed as a percentage of the maximum activity, typically observed at the zero time point.

Substrate Specificity. In addition to the reference substrates above, enzyme specificity was also evaluated using two immunogenic peptides derived from the sequence of γ-gliadin proteins in gluten. Both peptides were synthesized using solid-phase peptide synthesis. The peptide (SEQ ID NO:4) PQPQLPYPQPQLP contains the immunodominant γII-epitope, and is resistant to proteolysis by pepsin or any pancreatic enzyme. PEP specificity toward this substrate was assessed in a competitive assay in which 100 µM (SEQ ID NO:4) PQPQLPYPQPQLP and 100 µM Suc-Ala-Pro-pNA were mixed and reacted with 0.02 µM PEP at 25° C. The initial velocity of Suc-Ala-Pro-pNA cleavage was measured spectrophotometrically, whereas the initial velocity of (SEQ ID NO:4) PQPQLPYPQPQLP hydrolysis was determined via HPLC. The apparent specificity, $k_{cat}/_KM$, for the hydrolysis of (SEQ ID NO:4) PQPQLPYPQPQLP could be determined based on the known $k_{cat}/_{KM}$ of the enzyme for Suc-Ala-Pro-pNA and the observed reaction rates of the two substrates. In addition to PQPQLPYPQPQLP, PEP specificity for the more complex but physiologically relevant peptide (SEQ ID NO:12) LQLQPF-PQPQLPYPQPQLPYPQPQLPYPQPQPF (33-mer) was also assessed. Proteolysis reactions were performed at 37° C. in PBS buffer with 5-100 μM peptide and 0.1 μM PEP for time periods of 1 min-4 hrs.

The decrease in substrate concentration as well as concomitant intermediate and product build-up were monitored with HPLC analysis. RP-HPLC was performed on a system consisting of Beckman or Rainin Dynamax SD-200, a Varian 340 UV detector set at 215 nm and 280 nm. Solvent A was $H_2O$ with 0.1% TFA and solvent B was acetonitrile with 0.1% TFA; gradient used: 0-5% B in 0-15 min, 5-30% B in 15-30', 30-100% B in 30-35 min, 100% B for 5'; flow 1 ml/min; separation was performed on a 4.6×150 mm reverse phase C-18 column (Vydac, Hesperia, Calif., USA). Samples were centrifuged for 10 min at 13,400 g, prior to injection of 10-100 μl. Both (SEQ ID NO:4) PQPQLPYPQPQLP as well as the 33-mer have multiple post-proline endoproteolytic sites. Thus, multiple peptides accumulate during the course of the reaction, some of which are secondary PEP substrates in themselves. Electrospray-Ion Trap-MS-MS coupled with a UV-HPLC (LCQ Classic/Surveyor, ThermoFinnigan, CA) was used to identify the preferred cleavage sites in (SEQ ID NO:4) PQPQLPYPQPQLP and the 33-mer.

For further evaluation of the proteolysis of the 33-mer and (SEQ ID NO:4) PQPQLPYPQPQLP in the appropriate physiological environment, gluten (30 g/L) was suspended in 0.01 M HCl (pH=2.0) and incubated in the presence of pepsin (600 mg/L) for 2 h at 37° C. The resulting solution was neutralized using 10 M NaOH and diluted to 10 g/L in a phosphate buffer (40 mM, pH 6.5). 25 μl of this suspension were then supplemented with the 33-mer (0.1 mg/ml), (SEQ ID NO:4) PQPQLPYPQPQLP (0.08 mM), trypsin (0.1 mg/ml), chymotrypsin (0.1 mg/ml), elastase (0.02 mg/ml), carboxypeptidase A (0.02 mg/ml). Prolyl endopeptidase (FM or MX; 1×: 500 mU/ml; 5×: 2.5 U/ml; 10×: 5 U/ml) and rat intestinal brush border surface membranes (BB, 1×: 40 mU/ml, 2×: 80 mU/ml, DPP IV activity) were added to a total volume of 150 μl. The mixture was incubated at 37° C. and 25 μl aliquots were taken at 0, 5, 10, 30 and 60 min and immediately heat deactivated.

To examine the chain length specificity of individual PEPs, we performed competitive reactions containing both gluten-derived peptides, subjected the reaction mixture to RP-HPLC, and monitored the disappearance of each substrate was monitored as a function of time. The peak areas of the 33-mer (32.5 min) and (SEQ ID NO:4) PQPQLPYPQPQLP (27.5 min) were integrated.

In Vivo Endopeptidase Activity. An adult (female or male) rat was anesthetized and maintained at 36-37° C. during the entire surgical procedure. The peritoneal cavity was opened, and a small incision was made at the beginning and the end of a 15-20 cm jejunum segment. Polyethylene catheters were inserted and secured into the two ends. The input catheter was connected with a pump-driven syringe filled with a solution. The jejunum segment was perfused initially with PBS buffer to remove any residual debris at a flow rate of 0.4 ml/min. Purified peptide solutions (peptide concentration ranges from 25-100 μM) were then perfused at 0.4 ml/min through the jejunum segment with a 10-40 min residence time. In the case of a co-perfusion, the input catheter is connected with two simultaneous syringes, one with a peptide solution and the other with the prolyl endopeptidase solution (concentration ranges from 50-500 μU/μl). Fluid from the output catheter was collected into small centrifuge tubes in dry ice for subsequent analysis. The collected digestive products were analyzed by HPLC on a C18 column.

Results

PEP Protein Expression. FM and SC PEPs have their own signal sequences, and were therefore expressed as secreted, soluble enzymes in the periplasmic space of *E. coli*. A simple freeze-thaw lysis procedure led to recovery of periplasmic protein without significant contamination by cytoplasmic proteins. In contrast, the MX PEP lacks a native signal sequence, and was therefore expressed as a cytoplasmic protein. PEP was purified from each lysate by Ni-NTA affinity purification, followed by a second chromatographic step. The yields of active FM, SC and MX PEPs were 1 mg/L, 60 mg/L and 30 mg/L, respectively. The purity of the various PEPs was determined by SDS-PAGE to be >90%.

Kinetic Analysis with Reference Substrates. The activity of each PEP was initially evaluated using the standard chromogenic substrate succinyl-Ala-Pro-pNA. Release of the p-nitroaniline was detected at 410 nm, and kinetic data was fitted to the Michaelis-Menten relationship. Succinyl-Ala-Pro-pNA was selected as a reference substrate instead of the more commonly used Z-Gly-Pro-pNA due to the low solubility of the latter substrate, which necessitated use of co-solvents. The calculated $k_{cat}$ and $K_M$ values of FM, MX and SC PEPs for succinyl-Ala-Pro-pNA are tabulated (Table 3). While these enzymes all exhibited comparable level activity to that of a serine protease, MX PEP has a higher specificity than the FM PEP, whereas SC PEP has an intermediate level of specificity (Table 4). The higher specificity of MX can be attributed mainly to its higher affinity for the substrate, as reflected in the $K_M$.

TABLE 3

Kinetic parameters for Succinyl-Ala-Pro-p-nitroanilide hydrolysis by FM PEP, MX PEP and SC PEP.

|  | $K_{cat}$ (s$^{-1}$) | $K_M$ (mM) | $K_{cat}/K_M$ (mM$^{-1}$/s$^{-1}$) |
|---|---|---|---|
| FM PEP | 33 | 0.91 | 37 |
| MX PEP | 51 | 0.35 | 146 |
| SC PEP | 144 | 2.1 | 67 |

TABLE 4

Specificity of FM PEP, MX PEP and SC PEP for the immunogenic gliadin peptide (SEQ ID NO: 4) PQPQLPYPQPQLP.

|  | $K_{cat}/K_M$ (mM$^{-1}$/s$^{-1}$) |
|---|---|
| FM PEP | 178 |
| MX PEP | 548 |
| SC PEP | 492 |

Enzyme Activity vs. pH. The luminal environment of the duodenum is approximately at pH 6. Therefore, a therapeutically useful PEP must retain high specific activity at that pH. The steady state turnover rate, kcat, of each PEP was titrated in various pH conditions using 100-4000 μM succinyl-Ala-Pro-pNA, shown in FIG. 8. Both FM PEP and MX PEP exhibited active site $p_{Ka}$ around pH 6, indicating optimal activity in the pH 6-8 range. The diminished activity of both enzymes at pH 5 is consistent with the well-established role of a histidine residue as the general base in the serine protease catalytic triad, but alternatively it may indicate a change from the active enzyme conformation to an inactive state. Such conformational changes have been implicated in the catalytic cycle of the structurally characterized porcine brain PEP. Interestingly, the SC PEP, which has the broadest pH profile, shows a marked increase in maximum velocity under weakly basic conditions.

Figure 9:
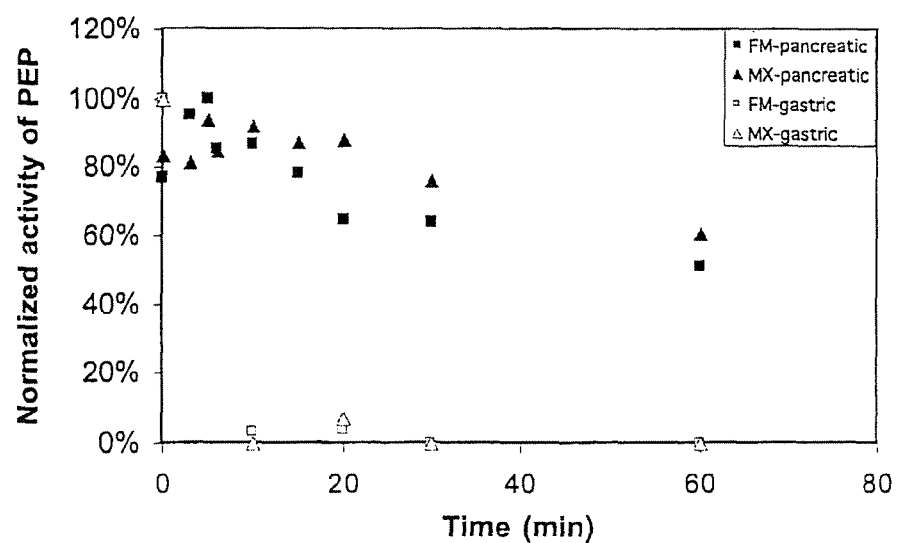
FIG. 9. Resistance of the FM PEP and the MX PEP to inactivation by gastric and pancreatic enzymes. Pancreatic enzyme stability was evaluated by treating 5 U/ml of the FM PEP and the MX PEP with 1 mg/ml trypsin, 1 mg/ml chymotrypsin, 0.2 mg/ml elastase and 0.2 mg/ml carboxypeptidase A (40 mM phosphate, pH=6.5). Pepsin stability was tested by treating the FM PEP and the MX PEP (5 U/ml) with 1 mg/ml pepsin (pH=2, 20 mM HCl).

PEP Stability. Although orally administered therapeutic proteins can be formulated to protect them from the acidic and proteolytic environment of the stomach, intrinsic acid stability of a PEP is likely to be a desirable characteristic in its use as a therapeutic agent for Celiac Sprue. We therefore evaluated the extent to which the activity of each PEP remains intact after 10 min of incubation at selected pH values between 1.6 and 3.9. Within this pH range, the FM PEP retained 50-70% of its original activity; the MX PEP retained 70-90% activity; and the SC PEP retained 30-80% activity. Thus, although all PEPs appear to be moderately acid-stable, the MX PEP is most versatile. Since therapeutic efficacy would require a PEP to act upon gluten in conjunction with pancreatic proteases that are secreted into the duodenum, the resistance of FM PEP and MX PEP toward both gastric and pancreatic enzymes was evaluated. For this we pre-incubated the enzymes with physiological quantities of either pepsin (at pH 2) or a cocktail comprising of trypsin, chymotrypsin, elastase and carboxypeptidase A (at pH 6.5). As can be seen in FIG. 9, both FM and MX PEP were highly susceptible to pepsin catalyzed proteolysis, whereas they appear to be remarkably stable to destruction in the presence of physiological quantities of the pancreatic enzymes.

Kinetic analysis using PQPQLPYPQPQLP as a substrate. The immunogenic peptide PQPQLPYPQPQLP is a recurring sequence in γ-gliadins, and is resistant to proteolysis by gastric and pancreatic proteases. It is also highly resistant to digestion by intestinal brush border peptidases, with only dipeptidyl carboxypeptidase I (DCP1) able to act upon it. Treatment of this peptide with PEP results in cleavage at internal proline residues, which in turn generates new recognition sites for brush border aminopeptidases. Thus, (SEQ ID NO:4) PQPQLPYPQPQLP represents a good test substrate to probe PEP specificity.

The $k_{cat}/K_M$ values of each PEP were determined in an assay mixture containing (SEQ ID NO:4) PQPQLPYPQPQLP as well as Suc-Ala-Pro-pNA as a competing substrate. The rates of disappearance of both substrates were determined by independent detection methods. The initial rate of disappearance of (SEQ ID NO:4) PQPQLPYPQPQLP was measured by HPLC, whereas the rate of consumption of Suc-Ala-Pro-pNA was measured spectrophotometrically. Both FM and MX PEP had a 5-fold higher specificity for the gluten peptide as compared to the chromogenic substrate, whereas the SC PEP showed a 7-fold increase in specificity for the gluten peptide (Table 4). This increase in specificity suggests that longer peptides may provide additional anchors at the catalytic site, a hypothesis that is consistent with the observation that Ala-Pro-pNA (which lacks an N-terminal succinyl group or a carboxybenzyl group) did not react with any of the PEPs.

To analyze the regiospecificity of hydrolysis of (SEQ ID NO:4) PQPQLPYPQPQLP by individual PEPs, samples corresponding to early time points were further analyzed by LC/MS/MS. The results, shown in FIG. 10A-10D, reveal that each PEP has unique subsite preferences. While the preferred site of cleavage by FM PEP was at the (SEQ ID NO:4) PQPQLPPYP|QPQLP position, MX PEP preferentially cleaved the same peptide at the (SEQ ID NO:4) PQPQLP|YPQPQLP position. SC had comparable preference for either site of cleavage. All enzymes preferentially cleaved the peptide at a proline located near the middle of the sequence, highlighting their functional difference from prolyl-specific exopeptidases such as DPP IV.

Figure 11:
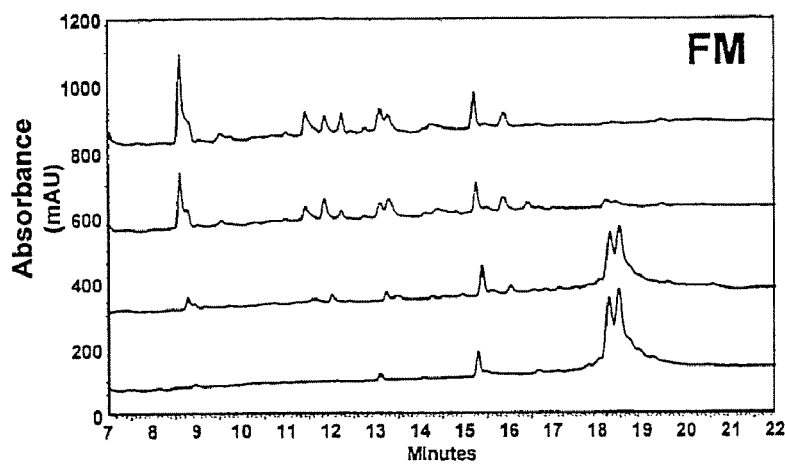
FIGS. 11A-11C. Hydrolysis of (SEQ ID NO:12) LQLQPFPQPQLPYPQPQLPYP QPQLPYPQPQPF by FM PEP, MX PEP and SC PEP. (A) Time dependence of hydrolysis in the presence of 10 µM substrate and 0.1 µM enzyme. The substrate appears as a doublet at a retention time of ca. 18 min, due to the presence of equal quantities of the 32-mer from which the N-terminal Leu is deleted; presence of this contaminant does not affect analysis. From the residual peak areas, the rates of substrate (33-mer+32-mer) disappearance were calculated as 2.3 µM/min (FM PEP), 0.43 µM/min (MX PEP) and 0.07 µM/min (SC PEP). (B) Initial cleavage fragments observed due to hydrolysis by FM PEP (t=1 min) and MX PEP (t=5 min). (C) Summary of initial cleavage fragments from FM PEP and MX PEP catalyzed hydrolysis of the 33-mer substrate.
Figure 11:
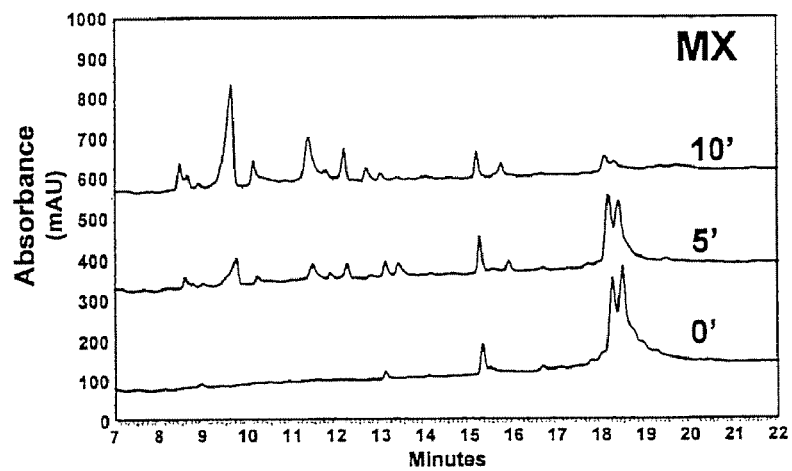
Figure 11:
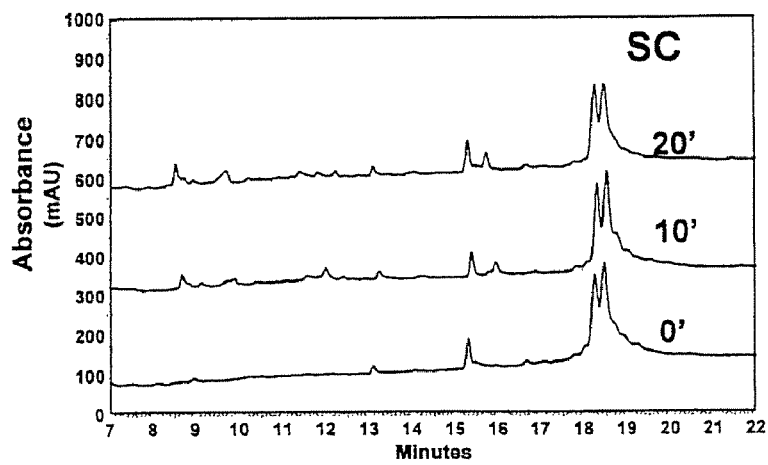

Chain Length Tolerance and Selectivity. It has been suggested that prolyl endopeptidases from the serine protease family are limited with regard to chain lengths of potential substrates. To test this hypothesis in the context of the three bacterial PEPs studied here, we compared their hydrolytic activities against a physiologically relevant 33-mer peptide sequence from wheat gliadin, (SEQ ID NO:12) LQLQPF-PQPQLPYPQPQLPYPQPQLP YPQPQPF (FIG. 11A). The FM PEP (0.1 µM) was able to hydrolyze 10 µM of the 33-mer in about 2-3 minutes, whereas the SC PEP required >1 hr to reach a comparable endpoint. Based on initial rates, the FM PEP was estimated to act 5-fold faster on the 33-mer than the MX PEP, and >20 fold faster than the SC PEP. Thus, the SC PEP appears to have a severe chain length restriction for long peptide substrates.

Figure 11B:
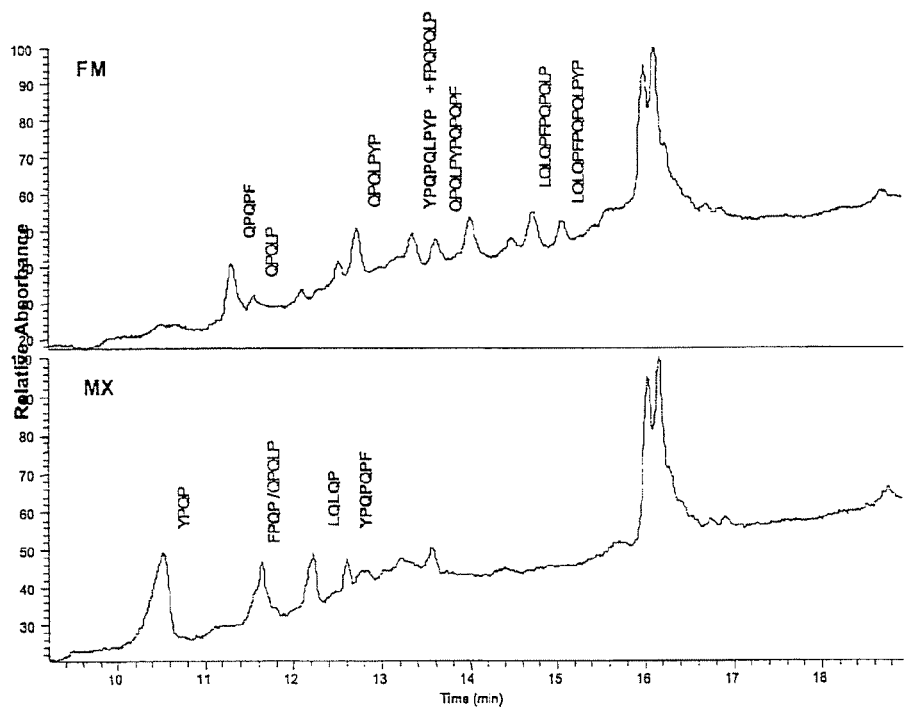
Figure 12A:
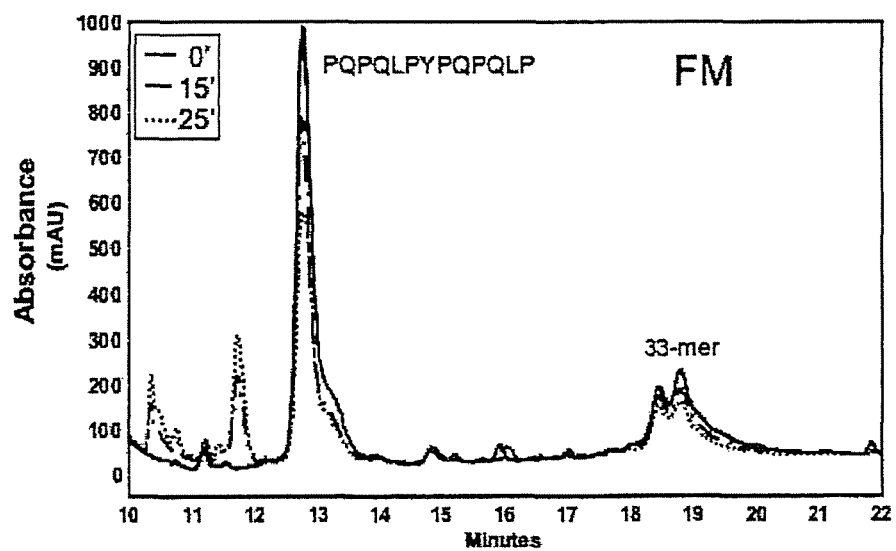
FIGS. 12A-12C. Competitive proteolysis of (SEQ ID NO:4) PQPQLPYPQPQLP and (SEQ ID NO:12) LQLQPF-PQPQLPYPQPQLPYPQPQLPYPQPQPF by each PEP. 10 µM of the longer peptide and 50 µM of the shorter peptide were co-incubated with 0.1 µM of (A) FM PEP; (B) MX PEP; (C) SC PEP.
Figure 12B:
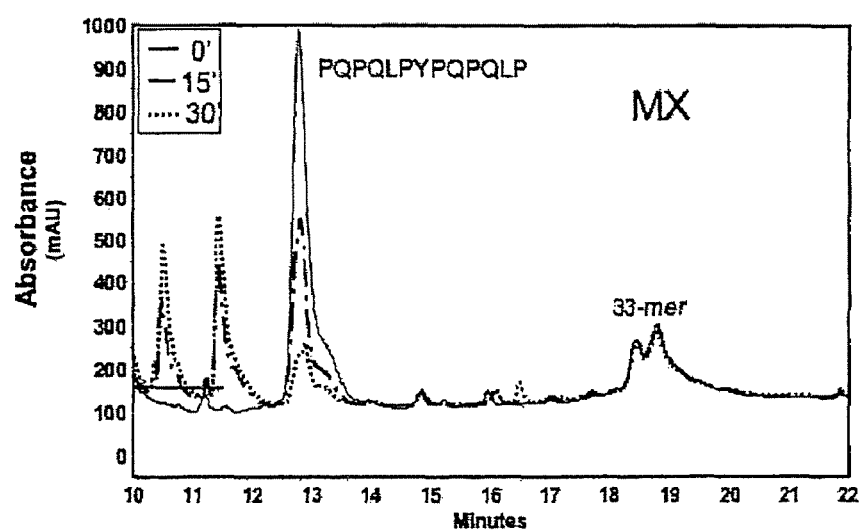
Figure 12C:
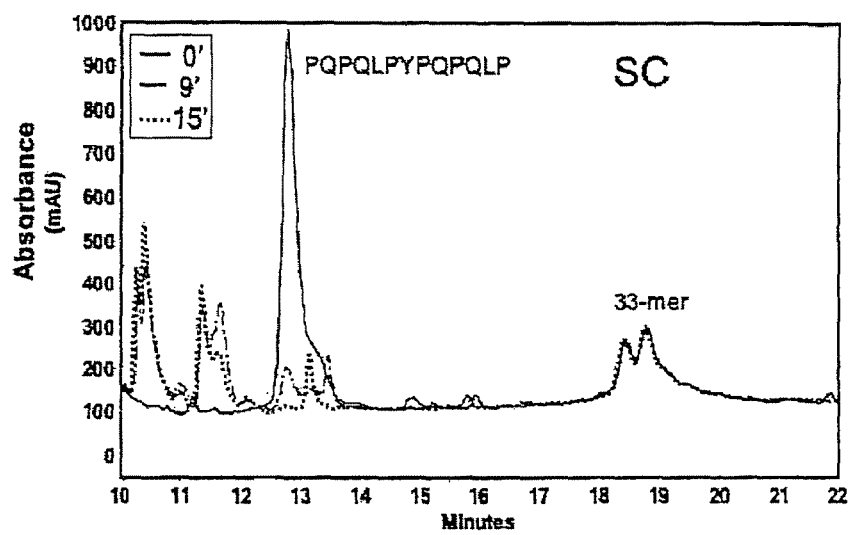

The intermediates and products from hydrolysis of the 33-mer by the FM and MX PEPs were analyzed by LC/MS/MS (FIG. 11B-C). Several features are noteworthy. First, even at relatively early time-points, the digestive products of the MX PEP were predominantly small fragments, whereas FM PEP digestion yielded a significant pool of long intermediates such as (SEQ ID NO:12, aa 1-19) LQLQPF-PQPQLPYPQPQLP, (SEQ ID NO:12, aa 1-14), LQLQPF-PQPQLPYP and (SEQ ID NO:12, aa 1-12), LQLQPFPQPQLP. Thus, although both PEPs are able to effectively proteolyze the 33-mer, they have distinct hydrolytic patterns on this complex substrate. In particular, either the MX PEP appears to be processive (i.e. for each 33-mer substrate molecule, it sequentially cleaves all the preferred sites in the chain prior to release), or alternatively the enzyme has a strong bias toward shorter chain substrates. It could also be noted that the C-terminal fragments generated by the two enzymes are different (QPQPF for the FM PEP, and YPQPQPF for the MX PEP). This finding is consistent with observed sub-site preference in the case of (SEQ ID NO:4) PQPQLPYPQPQLP digestion.

To directly investigate chain length selectivity of the three enzymes, we co-incubated (SEQ ID NO:4) PQPQLPYPQPQLP and (SEQ ID NO:12) LQLQPF-PQPQLPYPQPQLPYPQPQLPYPQPQPF with each PEP (FIG. 13A-C) Both the SC PEP and the MX PEP showed a clear preference for the 13-mer peptide, whereas the FM PEP showed comparable selectivity for both peptides.

Figure 13:
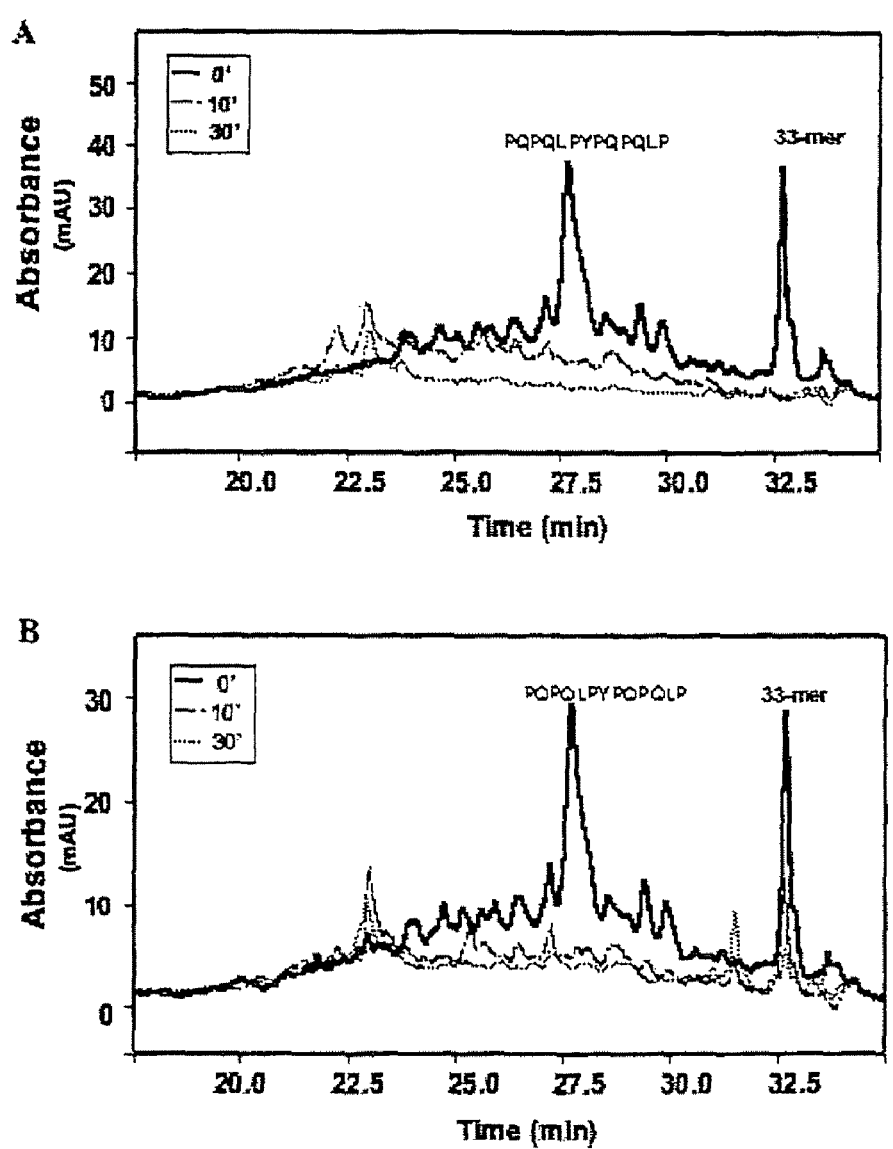
FIGS. 13A-13B. Competitive proteolysis of (SEQ ID NO:4) PQPQLPYPQPQLP (50 µM) and (SEQ ID NO:12) LQLQPFPQPQLPYPQPQLPYPQPQLPYPQPQPF (10 µM) in the presence of 30 mg/ml pepsin-treated gluten. This complex mixture of substrates was treated under physiological conditions with a mixture of pancreatic enzymes (trypsin, chymotrypsin, carboxypeptidase, elastase), brush border membrane enzymes (derived from rat small intestine) and either (A) FM PEP or (B) MX PEP.

To further evaluate the substrate preferences, (SEQ ID NO:4) PQPQPLPYPQPQLP and the 33-mer were mixed with pepsin-treated gluten, and allowed to react with pancreatic enzymes in the presence of BBM and either FM PEP or MX PEP. As seen in the HPLC traces (FIG. 13A-B), the 33-mer had the longest retention time, whereas (SEQ ID NO:4) PQPQLPYPQPQLP and other medium-length gluten peptides eluted earlier. Here too the FM PEP proteolyzed (SEQ ID NO:4) PQPQLPYPQPQLP, the 33-mer and other gluten peptides at comparable rates (FIG. 13A). In the MX PEP digestion, PQPQLPYPQPQLP and other smaller peptides were rapidly broken down (in 10 minutes), whereas hydrolysis of the 33-mer occurred at a slower rate (FIG. 13B).

Figure 14:
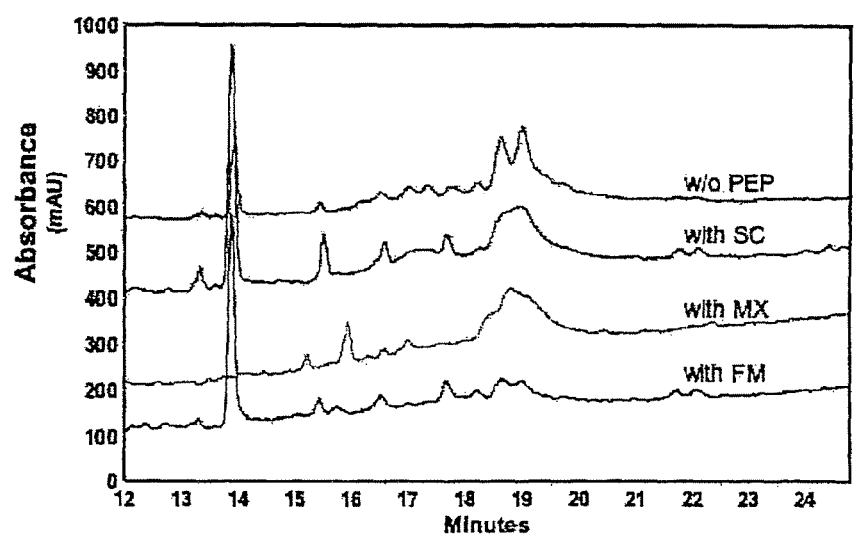
FIG. 14. (SEQ ID NO:12) Proteolysis of LQLQPF-PQPQLPYPQPQLPYPQPQL PYPQPQPF (5 µM) co-perfused with individual PEP's (0.1 µM) in the small intestinal lumen of an anesthetized rat. Each enzyme-substrate mixture was introduced via a catheter into a 15-20 cm segment of the upper jejunum. Samples were collected at the other end of the segment, and analyzed by UV-HPLC (215 nm). The control without any PEP is shown in the top trace.

In Vivo Hydrolysis. To validate the implications of the above biochemical observations for peptide digestion in the intact small intestine, each PEP was co-perfused in the rat jejunum with the 33-mer peptide substrate, and the effluent collected at a distance of 15-20 cm from the point of perfusion was analyzed. In this live animal model, the impact of concerted action of the perfused (luminal) PEP and the brush border (surface) peptidases is assessed. As shown by the in vitro results above, while the BBM enzymes were insufficient to process the 33-mer, FM PEP promoted more complete breakdown of the 33-mer than both the MX and the SC PEP (FIG. 14). Within a PEP dose range of 50-500 µU/µl, the extent of 33-mer hydrolysis increased with increasing PEP dose, demonstrating that higher doses of PEP could accelerate gluten breakdown in the mammalian gut.

In light of recent findings that related the strong antigenicity of gliadin peptides to their exceptional digestive resistance, prolyl endopeptidases were identified as a potentially interesting family of enzymes for oral Celiac Sprue therapy. Understanding the enzymological properties of these enzymes is an essential prerequisite for such use. In the above study, prolyl endopeptidases from three bacterial sources were selected and expressed in E. coli as recombinant proteins, and were subsequently purified and characterized. Two of these enzymes (from F. meningosepticum and S. capsulata) have been reported earlier, whereas the third enzyme (from M. xanthus) represents a new member of the prolyl endopeptidase family.

In order to examine the endoproteolytic properties of these enzymes, it is important to utilize peptide substrates with internal cleavage sites. Although model substrates such as Z-Gly-Pro-pNA or Suc-Ala-Pro-pNA have been frequently used to identify and characterize polyl endopeptidases, these substrates alone do not provide adequate insight to differentiate endopeptidases from each other or from proline-specific aminopeptidases (such as dipeptidyl peptidase IV (DPP IV)). In the context of Celiac Sprue, two peptides ((SEQ ID NO:4) PQPQLPYPQPQLP and (SEQ ID NO:12) LQLQPF-PQPQLPYPQPQLPYPQPQLPYPQPQPF) have been recognized as useful probes for studying the fundamental properties of prolyl endopeptidases, as well as for their potential for detoxifying gluten. The peptide (SEQ ID NO:4) PQPQLPYPQPQLP contains an epitope found in γ-gliadins that has been shown to play an immunodominant role in the T cell mediated response to gluten in the Celiac gut. It cannot be cleaved by any gastric or pancreatic proteases and is also highly resistant to digestion by intestinal brush border membrane (BBM) peptidases, with only dipeptidyl carboxypeptidase I able to act upon it at a very limited rate. Thus, the efficiency of intestinal metabolism of this peptide can be expected to improve in the presence of an exogenous prolyl endopeptidase, as has been verified in this study. Treatment of this peptide with PEP results in cleavage at an internal proline residue, which in turn generates a new recognition site for brush border aminopeptidases. Thus, (SEQ ID NO:4) PQPQLPYPQPQLP represents a good probe for PEP specificity.

The 33-mer gliadin peptide (SEQ ID NO:12) LQLQPF-PQPQLPYPQPQLPYPQPQLPYPQPQPF was selected as a complementary probe for these studies, because it is a stable, physiologically derived product of gastric and pancreatic digestion of γ-gliadin, and strongly stimulates proliferation of gluten-reactive T cells from virtually all Celiac Sprue patients tested thus far. Therefore, endoproteolytic breakdown of this 33-mer peptide represents an especially challenging goal for an exogenous PEP. Like most other antigenic gluten peptides, the 33-mer contains multiple proline residues, and can be expected to present more than one cleavage site to a PEP. At the same time its multivalent character suggests that PEP action alone is unlikely to eliminate all residual antigenicity of this peptide. Consequently, combined action of a PEP and the endogenous peptidases of the intestinal brush border membrane is required for immunological neutralization and dietary assimilation of this long proline-rich peptide.

Figure 10:
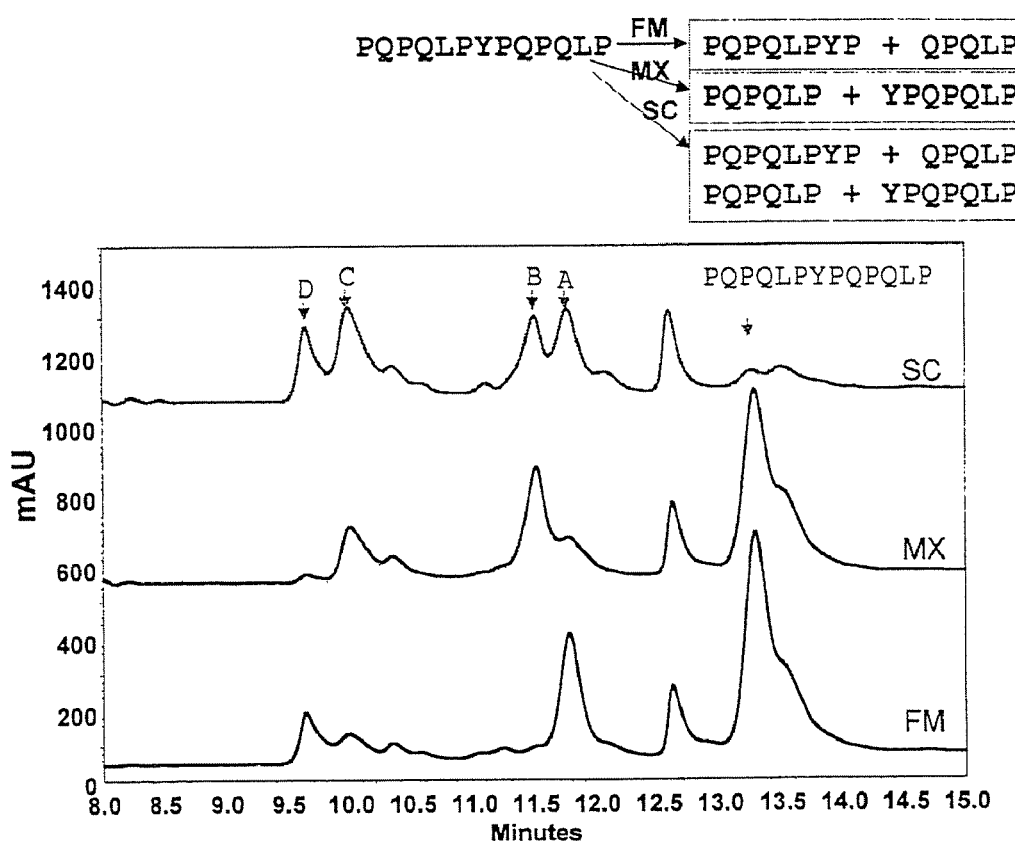
FIG. 10. Site specificity of PQPQLPYPQPQLP hydrolysis by individual PEPs. HPLC-UV (215 nm) traces are shown for each reaction mixture. Initial cleavage fragments (100 µM (SEQ ID NO:4) PQPQLPYPQPQLP, 0.1 µM enzyme, t=5 min) were identified by tandem mass spectrometry. The starting material (SEQ ID NO:4) PQPQLPYPQPQLP and the cleavage fragments A: (SEQ ID NO:4, aa. 1-8) PQPQLPYP, B: (SEQ ID NO:4, aa 7-13) YPQPQLP, C: (SEQ ID NO:12, aa 1-6) PQPQLP, D: (SEQ ID NO:4, aa 2-6) QPQLP) are indicated in the traces.

Our investigations into the molecular recognition features of three bacterial PEPs for two gliadin peptides have revealed at least two interesting and potentially important characteristics of these enzymes. First, although all three PEPs tested here exhibited high specific activity against reference chromogenic substrates (Table 3), they showed remarkable differences in chain length specificity (FIG. 10A-C). Whereas SC PEP and MX PEP had higher specificity for (SEQ ID NO:4) PQPQLPYPQPQLP than FM PEP (Table 4), the reverse was true for the longer 33-mer gliadin peptide (FIG. 11A), especially in the case of the SC PEP, which had extremely poor activity against the 33-mer.

Structural and biochemical analysis led to the proposal that the activity of PEPs is limited to substrates containing fewer than 30 amino acid residues. In that light the good activity of MX PEP and especially FM PEP against the 33-mer peptide is surprising. The broad chain length tolerance of FM PEP is vividly demonstrated in competitive in vitro and in vivo assays, where FM PEP was able to process longer and shorter substrates at comparable rates. Second, sequence analysis of the major proteolytic products derived from both gliadin substrates demonstrated that the PEP's had distinct sub-site specificity as well as regiospecificity in the context of the longer repetitive sequence. For example, the FM PEP preferentially cleaved at (SEQ ID NO:4) PQPQLPYP|QPQLP, whereas the MX PEP preferred the (SEQ ID NO:4) PQPQLP|YPQPQLP site, and the SC PEP had comparable activity toward either site.

Similarly, sequence analysis of initial hydrolytic products of the 33-mer peptide underscored regiochemical differences between FM PEP and MX PEP. Whereas MX PEP treatment generated fragments mostly of 4-5 residues (presumably processed sequentially from both termini), FM PEP yielded longer intermediates (presumably as a result of a preferential cleavage near the center of the peptide). Thus, the active sites of these enzymes are clearly different, which in turn has potential implications for the use of these enzymes detoxifying dietary gluten for a Celiac Sprue patient.

Figure 8:
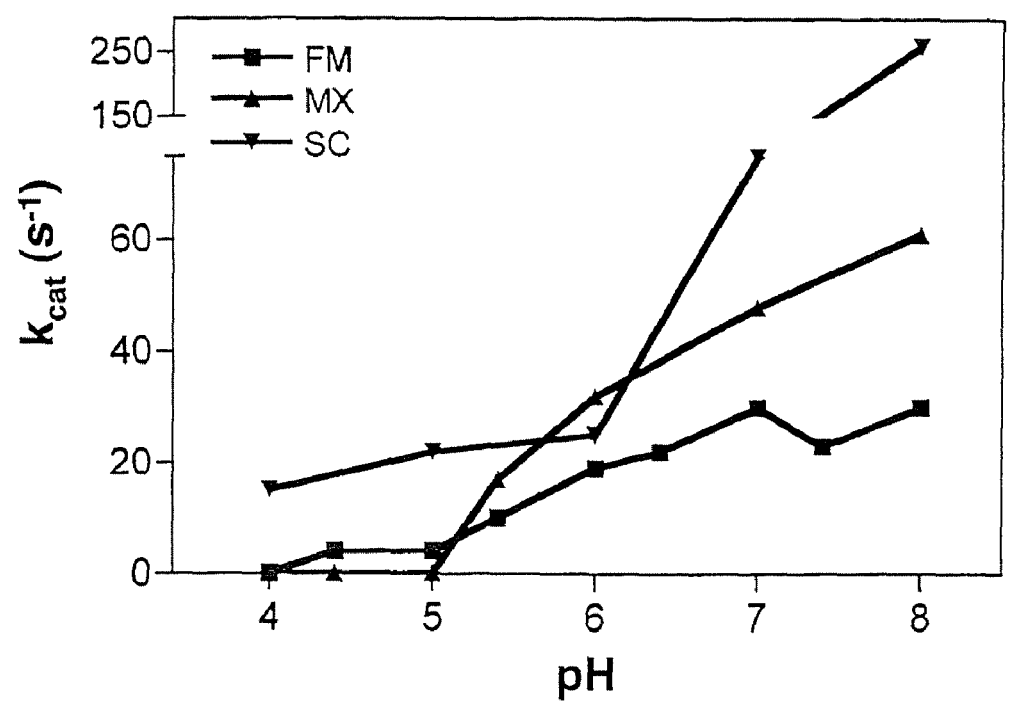
FIG. 8. Effect of pH on the turnover numbers ($k_{cat}$) of FM PEP, MX PEP and SC PEP.

In addition to analyzing substrate specificity, we have also investigated other therapeutically relevant properties of our set of three PEPs. They include pH dependence of enzyme activity, acid tolerance of the protein, and resistance toward inactivation by gastric, pancreatic and intestinal proteases/peptidases. All enzymes have a pH activity profile that is well matched to the mildly acidic environment of the upper small intestine (pH 6-6.5) (FIG. 3). They also appear to be moderately stable toward acid exposure as well as pancreatic protease (but not pepsin) action, with the MX PEP being the most stable (FIG. 8). The enzymes also retain activity in the intact small intestinal lumen of a rat, indicative of their stability toward both intestinal secretions as well as brush border membrane peptidases (FIG. 14). Finally, the expression levels of these enzymes vary significantly in recombinant E. coli. Specifically, in comparison to the FM PEP, the expression levels of SC and MX PEPs were substantially superior.

The porcine brain PEP has a didomain architecture, including an unusual β-propeller domain that appears to regulate proteolysis. Pairwise sequence alignments between this structurally characterized PEP and FM, MX and SC PEP reveal 39% (49%), 36% (45%) and 40% (48%) identity (similarity), respectively. These alignments also suggest that the bacterial PEPs are comprised of a catalytic and a β-propeller domain. Since their active sites are predicted to lie near the interface between the two domains, mutagenesis at the interdomain interface could alter protein dynamics and in turn affect substrate tolerance and specificity.

The above results provide a basis for protein engineering efforts of PEP enzymes. This family of serine proteases includes numerous other putative homologs whose cDNAs have been sequenced but whose gene products remain to be characterized. In light of the favorable properties of the MX PEP, which was expressed and characterized for the first time as part of this study, it will be useful to screen additional wild-type enzymes.

Example 4

Heterologous Expression of PEP in Lactobacilli

In one embodiment of the present invention, a Celiac Sprue patient is provided with a recombinant organism modified to express a PEP of the invention. The recombinant organism is selected from those organisms that can colonize the intestinal mucosa without detriment to the patient, thereby providing an endogenous source of PEP to the patient. As one example, *Lactobacilli* such as *L. casei* and *L. plantarium* can colonize the intestinal mucosa and secrete PEP enzymes locally. Given their widespread use in food processing, they can also be used as an efficient source of PEP for industrial (to treat foodstuffs) and medical (to prepare PEP for pharmaceutical formulation) use. PEPs can be expressed in such *lactobacilli* using standard recombinant DNA technologies. For example, Shaw et al. (Shaw, D M, Gaerthe, B; Leer, R J, Van der Stap, J G M M, Smittenaar, C.; Den Bak-Glashouwer, Heijne, M J, Thole, J E R, Tielen F J, Pouwels, P H, Havenith, C E G (2000) Immunology 100, 510-518) have engineered *Lactobacilli* species to express intracellular and surface-bound tetanus toxin. The intact PEP genes (including leader sequences for efficient bacterial secretion) can be cloned into shuttle expression vectors such as pLP401 or pLP503 under control of the (regulatable) amylase promoter or (constitutive) lactate dehydrogenase promoter, respectively. Alternatively, recombinant food grade *Lactobacilli* strains can be generated by site specific recombination technology (e.g. see. Martin M C, Alonso, J C, Suarez J E, and Alvarez M A Appl. Env. Microbiol. 66, 2599-2604, 2000). Standard cultivation conditions are used for *Lactobacilli* fermentation, such as those described by Martin et al.

Example 5

Heterologous Expression of PEP in Yeasts

Both naturally occurring and recombinant cells and organisms can be used to produce the glutenases useful in practice of the present invention. Preferred glutenases and producing cells include those from organisms known to be Generally Regarded as Safe, such as *Flavobacterium, Aeromonas, Sphingomonas, Lactobacillus, Aspergillus, Xanthomonas, Pyrococcus, Bacillus* and *Streptomyces*. Extracellular glutenase enzymes may be obtained from microorganisms such as *Aspergillus oryzae* and *Lactobacillus casei*. Preferred cells include those that are already used in the preparation of foodstuffs but have been modified to express a glutenase useful in the practice of the present invention. As one example, yeast strains such as *Saccharomyces cerevisiae* are useful for high level expression of secreted heterologous proteins. Genes encoding any of the PEPs described above (mature protein only) can be cloned in expression plasmids designed for optimal production of secreted proteins. An example of such a heterologous expression strategy is described in Parekh, R. N. and Wittrup, K. D. (Biotechnol. Prog. 13, 117-122, 1997). Either self-replicating (e.g. 2 micron) or integrating (e.g. pAUR101) vectors can be used. The GAL1-10 promoter is an example of an inducible promoter, whereas the ADH2 promoter is an example of a constitutive promoter. The cDNA encoding the mature PEP is fused downstream of a leader sequence containing a synthetic pre-pro region that includes a signal cleavage site and a Kex2p cleavage site. *S. cerevisiae* BJ5464 can be used as a host for production of the peptidase. Shake-flask fermentation conditions are described by Parekh and Wittrup in the above-cited reference. Alternatively, high cell density fed-batch cultures can be used for large scale production of the peptidases; a representative procedure for this purpose is described in Calado, C. R. C, Mannesse, M., Egmond, M., Cabral, J. M. S, and Fonseca, L. P. (Biotechnol. Bioeng. 78, 692-698, 2002).

Example 6

Enteric Capsule Formulation of Prolyl Endopeptidase

Gelatin capsules are filled with 100 mg prolyl endopeptidase and 10 mg of silicon dioxide. The capsules are enterically coated with Eudragit polymer and put in a vacuum chamber for 72 hours. The capsules are then held at a range of temperature of 10° C. to 37° C. and a controlled humidity level of 35-40%.

Example 7

Studies of Enteric Capsule Formulation of Prolyl Endopeptidase

A study is conducted where patients with Celiac Sprue are enrolled in a two week-long study. Gelatin capsules containing 90% prolyl endopeptidase mixed with 10% silicon dioxide are used. The capsules are hand-filled with the mixture, banded, and coated with a 10% Sureteric enteric coating (a polymer of polyvinylacetatephthalate developed by the Canadian subsidiary of Merck & Company). Samples are acid-tested by exposing the coating to 1 NHCL for one hour in order to simulate the acid environment of the stomach. The capsules are then put in a vacuum chamber for 72 hours.

Two 100 mg capsules are administered to each patient prior to each meal. The patients are instructed to eat all kinds of food without abstaining from those that were known to cause distress, e.g., bloating, diarrhea, and cramps.

Example 8

Enteric Pill Formulation of Prolyl Endopeptidase 400 mg of L-tartaric acid and 40 mg of polyethylene glycol-hydrogenated castor oil (HCO-60) are dissolved in 5 ml of methanol. This solution is placed in a mortar previously warmed to 30° C. To the solution is added 100 mg of prolyl endopeptidase. Immediately after the addition of PEP, the mixture is stirred with a pestle under a hot air current (40° C) and then placed in a desiccator under vacuum overnight to remove the solvent. The resulting solid-mass is pulverized with a pestle and kneaded with 30 mg of sodium bicarbonate and a small amount of 70% ethanol. The mixture is then divided and shaped into pills of about 2 mm size and thoroughly dried. The dried pills are given a coating of hydroxypropylmethylcellulose phthalate (HP-55) to obtain an enteric formulation.

Example 9

Endoprotease Activity

The gene for an endoprotease (EPB2; PubMed accession number U19384, nt 94-1963) from barley (*Hordeum vulgare* subsp. *vulgare*) was subcloned into a pET28b (Invitrogen) vector using BamH1 and EcoR1 insertion sites; the resulting plasmid was designated pMTB1. An inactive 43 kDa proprotein form of EPB2 was expressed from pMTB1 in the cytoplasm of BL21 *E. coli* cells. The proprotein was solubilized from the inclusion bodies using 7 M urea. The solubilized protein was purified on a Ni-NTA column. Auto-activation of proEPB2 to its mature, active form was achieved by addition of citrate-phosphate buffer, pH 3 (prepared by mixing 0.1 M sodium citrate and 0.2 M sodium phosphate). Under such acidic conditions, proEPB2 converts rapidly into a mature form with a molecular weight of 30 kDa (FIG. 2). By 72 hours, mature EPB2 undergoes autolysis. N-terminal sequencing yielded an N-terminal sequence beginning with VSDLP.

Under acidic conditions, the mature form of EPB2 efficiently digests purified α2-gliadin, a source of peptides that are immunogenic to people who suffer from Celiac Sprue. The cysteine proteinase inhibitor, leupeptin, inhibits this activity, confirming its mechanism as a cysteine protease. The pH optimum of proEPB2 activation and α2-gliadin digestion is 2.4-3.5, which can therefore provide a treatment for Celiac Sprue consisting of oral administration of proEPB2.

Example 10

Formulation and Efficacy Analysis of *M. xanthus* PEP

Lyophilization of *M. xanthus* PEP was performed as follows. The PEP was purified as described in Example 3, and concentrated to an initial concentration of 7.7 mg/ml by Tangential-Flow Filtration (TFF) using a 10K MWCO Pellicon difiltration membrane (Millipore, PLCGC10, 50 cm, Cat. No. PXC010C50). TFF (using a LabScale TFF from Millipore, Cat. No. 29751) was performed for approximately 12 hours (pressure of 50 psi (retentate)/30 psi (permeant)), with periodic addition to the reservoir of 50 mM Sodium Phosphate, 3% Sucrose pH 7.5. Thereafter, PEG-4000 was added with a target concentration of 1%. The final protein concentration was 70-100 mg/ml. This material was centrifuged, then lyophilized. The lyophilization was performed in square petri dishes (Falcon Cat. No. 35-1112) in a DuraStop lyophilizer using parameters outlined in the Table below. Typically, 0.7-0.85 mg PEP was present per mg of lyophilized material. No loss of specific activity of the PEP was observed upon lyophilization.

| Step | Temperature | Pressure | Duration | Ramp Rate |
|---|---|---|---|---|
| Freezing 1 | −50° C. | Atmospheric | 2 hrs | 0.3° C./minute |
| Annealing | −35° C. | Atmospheric | 3 hrs | 0.3° C./minute |
| Freezing 2 | −50° C. | Atmospheric | 2 hrs | 0.3° C./minute |
| 1° Drying | −20° C. | 100 mTorr | 16.9 hrs | 0.5° C./minute |
| 2° Drying | +25° C. | 100 mTorr | 8.0 hrs | 0.2° C./minute |

*P. Temp. = Avg. Product Temp. at end of step.
**1° = Primary Drying.
***2° = Secondary Drying Blending for the *M. xanthus* PEP was performed as follows. Lyophilized cakes were pulverized to a light powder. All samples were weighed for recovery and stored in sealed 50 mL conical vials at 4° C. A blend was prepared as shown below. The excipients were selected to provide proper flow and disintegration properties for the blended mixture.

| Order of Addition | Excipient | Percentage |
|---|---|---|
| 1 | Lyophilized enzyme cake/powder | 63% |
| 2 | Calcium Silicate | 2% |
| 3 | Talc | 5% |
| 4 | Crospovidone | 5% |
| 5 | Avicel | 25% |

The lyophilized enzyme and excipients were blended in a V-blender for several hours. The material was then used to make enteric-coated capsules or tablets. 100-150 mg *M. xanthus* PEP could be loaded into a single hard gelatin capsule, size 00 (Capsugel). Alternatively, Vcap vegetable capsules (size 00, Capsugel) can also be used with no impact on enzyme activity.

For enteric coating of the capsules, an enteric coating solution was prepared as shown below:

| Order of Addition | Excipient | Amount added |
|---|---|---|
| 1 | RODI water | 49.5 mL |
| 2 | Talc | 8.1 g |
| 3 | Eudragit L50 D-55 | 111.0 mL |
| 4 | Triethyl Citrate | 1.62 mL |

The enteric coating was mixed vigorously in a beaker on a stir plate. The solution was then decanted into a spray bottle. Rat capsules were carefully spread on paper towels in groups of 20 and the enteric coating solution sprayed onto the capsules. Warm air was used to partially dry the capsules before moving them to a dry paper towel where they air-dried for 30 minutes before the next coat was applied. A total of 3 coats were applied in order to cover all sides of the capsules. These were air dried several hours before being transferred to a storage container. Although some activity of the PEP is lost as a result of enteric coating, a substantial fraction of the activity is retained, and is stable for at least 1 month at 4 C storage.

An alternative method to formulate the enzyme for intestinal delivery is as an enteric-coated tablet. Tablets have the advantage of more rapid dissolution in the weakly acidic environment of the upper small intestine. Another advantage of the tablet formulation is that more enzyme can be compacted into a smaller volume than for a capsule. Their primary liability is that proteins frequently denature under high pressures. In a method of tablet preparation of *M. xanthus* PEP, the same lyophilized blend as above was used. Tablets were prepared at a punch strength of 3000 psi held for 15 seconds. No activity was lost in the process, demonstrating the feasibility of tablet formulations of this enzyme.

To test the efficacy of the enteric-coated oral capsule formulation described above, two types of tests were performed. In vitro dissolution tests were performed on a Hanson SR8-Plus Dissolution Tester using Simulated Gastric Fluid (SGF; 2 g/L NaCl, pH 1.2, adjusted using 6 N HCl) and Simulated Intestinal Fluid (SIF; 6 g/L monobasic potassium phosphate with or without 10 g/L pancreatin, pH 6.8, adjusted using 5 N NaOH). Enteric coated capsules were first tested for resistance to dissolution in SGF for up to 2 h at 37° C. No protein release was noted. Subsequently the capsules were subjected to similar dissolution tests in SIF at 37° C. A substantial fraction of the encapsulated material was released in 15 min. By 30 min the material had been completely released.

In vivo tests of the capsules were performed in rats using smaller hard gelatin capsules (Size 9 capsules, Torpac).

Approximately 16 mg of the lyophilized formulation blend was encapsulated in each enteric-coated capsule, corresponding to ~7 mg PEP. Rats fasted overnight were administered via oral gavage one PEP or placebo capsule along with a measured quantity (300 mg gluten/kg body weight) of gluten syrup prepared as follows. 300 g commercially available wheat gluten flour (Bob's Red Mill, Milwaukie Oreg.) was added to 10 L of a 0.01 M HCl solution to achieve a pH of 2.0. Pepsin (6.0 g, American Laboratories) was added. After incubation at 37° C. for 1 h, the pH was adjusted to 2.0 by addition of 35 ml 1M HCl. After maintenance for an additional 2 h at 37° C., the solution was neutralized by addition of 35 g of $Na_2HPO_4$, and the pH was adjusted to 7.9 with 10 M NaOH (32.5 ml). Trypsin/Chymotrypsin powder (3.75 g) (Enzyme Development Corp; 1000 USP/mg in trypsin, 1000 USP/mg in chymotrypsin) was then added, the reaction maintained at 37° C. for 2 hours, pH 7.9 (pH re-adjustment to 7.9 after 1 hour, with 10 M NaOH) and heated at 100° C. for 15 minutes to inactivate the enzymes. The final gluten solution was filtered through cheesecloth to remove residual large particles. One PEP capsule-fed animal and one sham capsule-fed animal was sacrificed after 45 min and 90 min each, and the small intestinal contents were analyzed for gluten content via C18 reversed phase HPLC. Chromatograms were normalized for total protein content in each sample. Top=45 min, Bottom=90 min (green=placebo, blue=PEP capsule).

As shown in FIGS. 15A and 15B, gluten-derived peptides elute in the 20-30 min region. At 45 min as well as 90 min, the pepsin-trypsin-chymotrypsin treated gluten was minimally metabolized in the sham-fed animals, whereas it appears to be extensively metabolized. Together, these results indicate that enteric-coated PEP capsules can survive the gastric environment of the stomach, and catalyze proteolysis of dietary peptides in the small intestine.

Example 11

Detoxification of Gluten by Enzyme Treatment

Prolyl endopeptidases (PEPs) can be administered at the time of a meal, to be released or activated in the upper intestinal lumen where they complement the pancreatic proteases by further processing the toxic gliadin peptides in the intestinal lumen, thereby preempting their interaction with the intestinal surface.

It was first established that a low-dose, short-term (5-10 g/day for 14 days) gluten oral supplement induces fat and carbohydrate malabsorption when given to asymptomatic Celiac Sprue patients on an otherwise gluten free diet. This protocol was modified to examine the effect of gluten pretreated with pepsin, trypsin and chymotrypsin (PTC-Gluten) as compared to PTC-Gluten additionally treated with PEP (PTC-Gluten+PEP). In this study, Celiac patients maintaining a gluten-free diet ingested a supplement of 5 g/day gluten as PTC-Gluten or PTC-Gluten+PEP in an orange-lemon juice vehicle for 14 days in a double-blind crossover manner. A 6-week washout interval between individual arms of the crossover trial allowed patients to recover completely from the effects, if any, of the test material in the first arm. The results indicate that ingestion of PEP-treated gluten with its reduced or absent gliadin peptides does not produce a malabsorptive response in Celiac Patients, and demonstrates that oral supplementation with this peptidase is therapeutic in Celiac Sprue.

Subjects and protocols: This study was approved by the Institutional Review Board of the Palo Alto Medical Foundation in Palo Alto, Calif., and all participants in the study were counseled regarding risks and signed an informed consent document. 22 patients were recruited who were in symptomatic remission on a gluten-free diet. Two patients dropped out of the study, one near the end of the first stage and the other prior to the second stage. The 20 patients who completed the study included 7 men and 15 women aged 21 to 78 (mean age 49). The time since diagnosis for the 20 patients ranged from 3 months to 18 years (mean 6 years). Patients provided copies of their initial small-intestinal biopsy pathology report and laboratory reports documenting a history of at least one positive celiac antibody (gliadin, endomysial or transglutaminase) to verify a diagnosis of Celiac Sprue. They also completed an entry questionnaire inquiring about their medical history, adherence to the gluten-free diet, and current symptoms. The format of the study was a double-blinded crossover in which each patient consumed either a low daily dose of a gluten supplement (5 g; equivalent of one-half slice of bread) that was predigested with pepsin, trypsin and chymotrypsin alone (PTC-Gluten) or PTC-Gluten treated with prolyl endopeptidase (PTC-Gluten+PEP). The PEP in the latter orange juice mixture was completely inactivated through a heating process following proteolysis of the gliadin peptides. Each stage consisted of 14 days, separated by a washout period of 6 weeks. Following the 6 week washout period, the patients switched in stage 2 to consuming the other type of orange juice mixture daily for 14 days.

Studied variables: During each stage of the study, patients completed a daily questionnaire inquiring about symptoms and their adherence to the gluten-free diet. Patients documented the presence or absence of 13 symptoms, including diarrhea, abdominal bloating, excessive gas passage, abdominal discomfort or pain, nausea, and fatigue by use of a 0-3 ordinal scale (none, mild, moderate, and severe) yielding a maximum possible daily symptom score of 39. Patients also indicated their perceived adherence to a gluten-free diet using a 0-3 scale with 0, 1, 2, and 3 indicating no ingestion of gluten, mild, moderate, and severe contamination, respectively. All laboratory tests were performed by Quest Diagnostics Laboratory in San Juan Capistrano, Calif. A Celiac antibody panel, comprised of serum anti-gliadin IgA and IgG antibodies, anti-tissue transglutaminase IgA and IgG antibodies and a total serum IgA level was obtained at baseline (within 2 weeks of the start of the study). The serum anti-gliadin IgA antibodies and anti-tissue transglutaminase IgA and IgG antibodies were measured by an enzyme linked immunosorbent assay (ELISA) kit (INOVA Diagnostics, Inc., San Diego, Calif.). The results were obtained by constructing standard curves with dilutions of a positive reference serum and converted to concentrations of arbitrary ELISA units (normal <20 EU/ml). Total serum IgA levels were determined by an Integra instrument (Roche) (normal <81 mg/dl). A complete blood count with automated differential was obtained before and after each stage. The 25 g D-xylose 5-hour urine excretion test and the 72-hour quantitative fecal fat test were measured at baseline and on Day 15. Following an overnight fast and after passing and discarding the urine, patients consumed a 25-gram oral dose of D-xylose dissolved in 200-300 ml of water and collected all of the urine voided during the 5 hours after administration of the dose. Patients were instructed to drink an additional 400-600 ml of water during the first two hours of the test to ensure adequate urine flow. A xylose excretion of less than 4 g in 5 hours was considered abnormal. For the 72 h quantitative fecal fat test, patients were instructed to consume a diet containing 80-100 g fat per day during the collection. The fecal fat excretion was determined by a gravimetric method.

Production of the gluten-containing orange juice mixture: Because it was technically cumbersome to work with precise amounts of gluten for use in making food products such as bread, muffins, or rolls, we produced an orange juice drink into which an exact amount of cooked wheat gluten flour could be readily incorporated. All components of the Orange Juice Mixture were food grade. Commercially available wheat gluten flour (Bob's Red Mill, Milwaukie Oreg.) was added to 10 L of a 0.01 M HCl solution to achieve a pH of 2.0. Pepsin (6.0 g, Pepsin (P) NF powder, 1:10000, American Laboratories, Omaha Nebr.) was added. After incubation at 37° C. for 1 h, the pH was adjusted to 2.0 by addition of 35 ml 1 M HCl. After maintenance for an additional 2 h at 37° C., the solution was neutralized by addition of 35 g of $Na_2HPO_4$, and the pH was adjusted to 7.9 with 10 M NaOH (32.5 ml). Trypsin (T)/Chymotrypsin (C) powder (3.75 g) (Enzyme Development Corp., New York, N.Y.; 1000 USP/mg in trypsin, 1000 USP/mg in chymotrypsin) was then added, the reaction maintained at 37° C. for 2 hours, pH 7.9 (pH readjustment to 7.9 after 1 hour, with 10 M NaOH) and heated at 100° C. for 15 minutes to inactivate the enzymes. The final PTC-Gluten solution was filtered through cheesecloth to remove residual large particles. Analysis of the protein content (Lowry method) of the filter residue showed no significant loss of protein in the residue on the cheesecloth. This treatment of gluten was shown to yield the final gliadin peptides by analysis on a reverse phase C-18 HPLC column. Frozen Orange Juice Concentrate (Minute Maid, thawed, 2 oz/dose) and Lemon Juice Concentrate (Minute Maid, 0.5 oz/dose) were added to the PTC-Gluten solution, mixed, and transferred to plastic beverage containers (8 oz/5 g gluten). The containers were stored in a −20 C freezer until the day before use. Analysis revealed that the gluten digests were stable by HPLC analysis for at least 60 days. Preparation of PTC-Gluten +PEP was identical to the above protocol, except that the PTC-Gluten was solution was treated with 200 units PEP/g gluten for 1 h prior to heat treatment.

Results:

Baseline Labs: Since the Celiac serum antibody titers may be intermittently abnormal in this disease, even when patients are in full clinical remission, the antibody levels were not considered to be an exclusion criterion for participation in the study. None of the 20 patients who completed the study was IgA deficient. Eight patients (40%) had at least one abnormal antibody level at baseline. Five out of the 20 patients had missing baseline xylose urine test results due to laboratory error. Of the remaining 15 patients, 3 (20%) had an abnormal urine xylose at baseline. One out of the 20 patients had a missing baseline fecal fat result, again due to laboratory error. Twelve of the remaining 19 patients (63%) had an abnormal baseline fecal fat. None of the patients had all 3 baseline tests (an antibody, urine xylose, and fecal fat) abnormal, but 5 patients had 2 abnormal tests (4 with an abnormal antibody and an abnormal fecal fat, 1 with an abnormal antibody and an abnormal xylose, and 2 with an abnormal fecal fat and an abnormal xylose, Table 5A-B). Therefore, only 3 of the 14 patients with full baseline data had a normal antibody panel, normal fecal fat, and normal urine xylose. There was no significant correlation between baseline lab values and time since diagnosis or perceived dietary adherence in the 2 weeks prior to study entry.

TABLE 5a

Baseline Labs for patients on a gluten-free diet for <=2 years

| | Patient | | | | | | | |
|---|---|---|---|---|---|---|---|---|
| | A | D | E | G | I | L | O | Q | T |
| Ttg IgG (normal <20) | 8 | 16 | 6 | 7 | 8 | 8 | 5 | 3 | 5 |
| Ttg IgA (normal <20) | 161 | 19 | 6 | 19 | 13 | 200 | 47 | 15 | 9 |
| AGA IgA (normal <20) | 21 | 19 | 7 | 10 | 11 | 91 | 12 | 8 | 11 |
| Fecal Fat (normal <7 g/24 hrs) | 12 | 5.1 | 1.9 | 22 | 4.4 | 13 | * | 7.6 | 25 |
| Urine Xylose (normal >4 g/5 hrs) | 6.7 | 6.2 | 6.0 | * | * | 5.9 | 4.2 | 2.2 | 6.2 |
| Years since diagnosis | 0.25 | 2 | 0.67 | 1 | 2 | 0.5 | 2 | 0.33 | 1.33 |

TABLE 5b

Baseline Labs for patients on a gluten-free diet for >2 years

| | Patient | | | | | | | | | | | |
|---|---|---|---|---|---|---|---|---|---|---|---|---|
| | B | C | F | H | J | K | M | N | P | R | S | U | V |
| Ttg IgG (normal <20) | 9 | 8 | 7 | 33 | 10 | 16 | 5 | 3 | 5 | 5 | 5 | 10 | 35 |
| Ttg IgA (normal <20) | 16 | 43 | 5 | 10 | 119 | 26 | 8 | 11 | 3 | 14 | 8 | 7 | 10 |
| AGA IgA (normal <20) | 14 | 11 | 8 | 7 | 40 | 23 | 9 | 11 | 8 | 16 | 17 | 9 | 11 |
| Fecal Fat (normal <7 g/24 hrs) | 10 | 14 | 4.5 | 16 | 5.3 | 3.4 | 8.2 | 11 | 11 | 6.6 | 15 | 6 | 3.9 |
| Urine Xylose (normal >4 g/5 hrs) | * | 4.8 | * | 5.3 | 2.2 | * | 5.5 | * | 3.0 | 4.0 | 6.1 | 9.9 | 5.6 |
| Years since diagnosis | 3.25 | 18 | 8 | 10 | 8 | 3.17 | 6.67 | 11 | 11 | 4 | 17 | 14.8 | 2.75 |

Questionnaire: Participants were asked to maintain a strict gluten-free diet during the study. There was no significant difference in dietary adherence between the two stages for any of the 20 patients. Eight of the 20 patients (40%) reported no perceived episodes of gluten-contamination in their food intake during either stage. The majority of the other patients reported ingesting small amounts of gluten containing foods (mild contamination) for 1-3 days in one or both stages. Two patients (10%) reported contamination on at least half of the days of each stage. Both of these patients had two abnormal baseline tests. In addition, five of the 20 patients (including the two patients just mentioned) perceived that they had mild gluten contamination sometime during the 2 weeks prior to entry into the study while the majority of patients (15 of 20; 75%) reported that they had maintained a strict gluten-free diet during that time frame. Daily symptom scores ranged from 0 to 22, out of a maximum possible score of 39. Most patients had relatively few symptoms during either the control or PEP treatment stage. The average Total Stage Symptom Score (the sum of the 14 daily symptom scores for that stage) was 22 (range 0 to 71) for the Control Stage, and 23 (range 4 to 82) for the PEP Stage. There was no correlation of symptoms as a function of the gluten preparation.

Gluten Challenge and PEP: To determine whether PEP was effective in avoiding a malabsorptive response, we identified those patients who had a positive control phase, i.e. a positive gluten challenge, based on fecal fat or xylose testing. For patients who had a positive gluten challenge, the putative avoidance of a malabsorptive response could then be determined. A patient was considered to have a positive gluten challenge based on xylose if the pre-stage and post-stage xylose values met either one of the following criteria: 1) pre-stage urine xylose was normal (>4.0 g/5 h) and the post-stage xylose was abnormal (<4.0 g/5 h); or 2) there was at least a 25% decline in the urine xylose from pre-stage to post-stage. A patient was considered to have a positive gluten challenge based on fecal fat if the patient's pre-stage and post-stage fecal fat values met either one of the following criteria: 1) the pre-stage fecal fat was normal (<7.0 g/24 h) and the post-stage fecal fat was abnormal (>7.0 g/24 h); or 2) if the pre-stage fecal fat was abnormal, the post-stage fecal fat revealed at least a 25% increase from the pre-stage value.

TABLE 6

Results of the Gluten Challenge Based on Urine Xylose

|  | All patients with full xylose data (N = 14) | | Subgroup with normal (>4 gm/5 hrs) Pre-stage Xylose (N = 10) | |
|---|---|---|---|---|
| Positive Gluten Challenge | 8/14 | 57% | 5/10 | 50% |
| PEP Effective | 4/8 | 50% | 3/5 | 60% |

Figure 16:
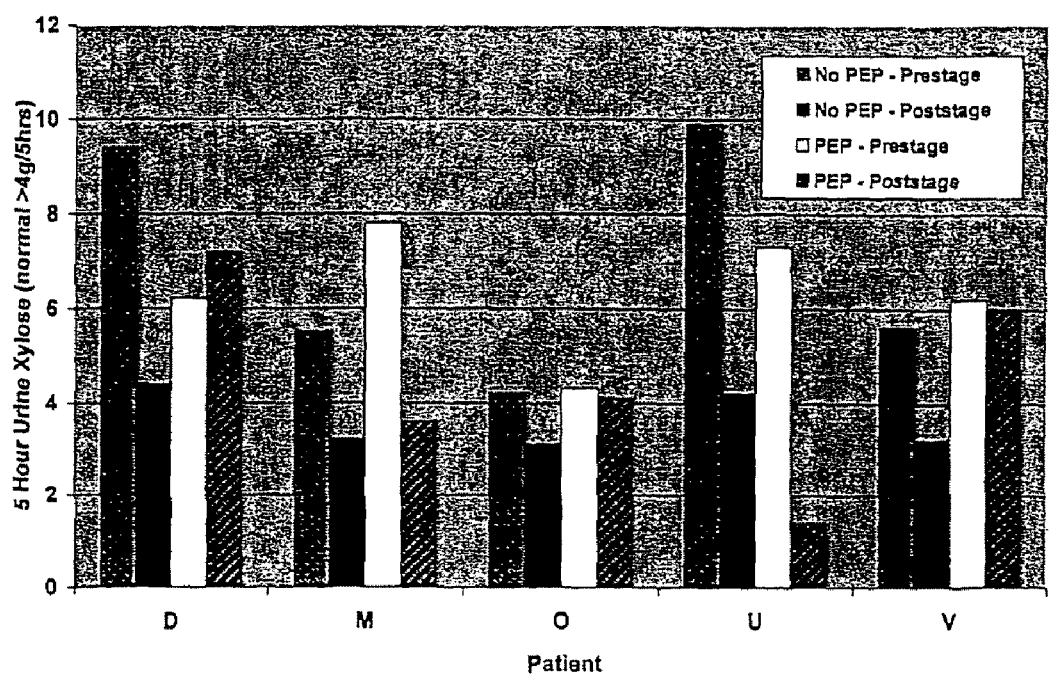
FIG. 16. Urine xyloses for patients with normal pre-stage xylose absorption and a positive xylose gluten challenge.
Figure 17:
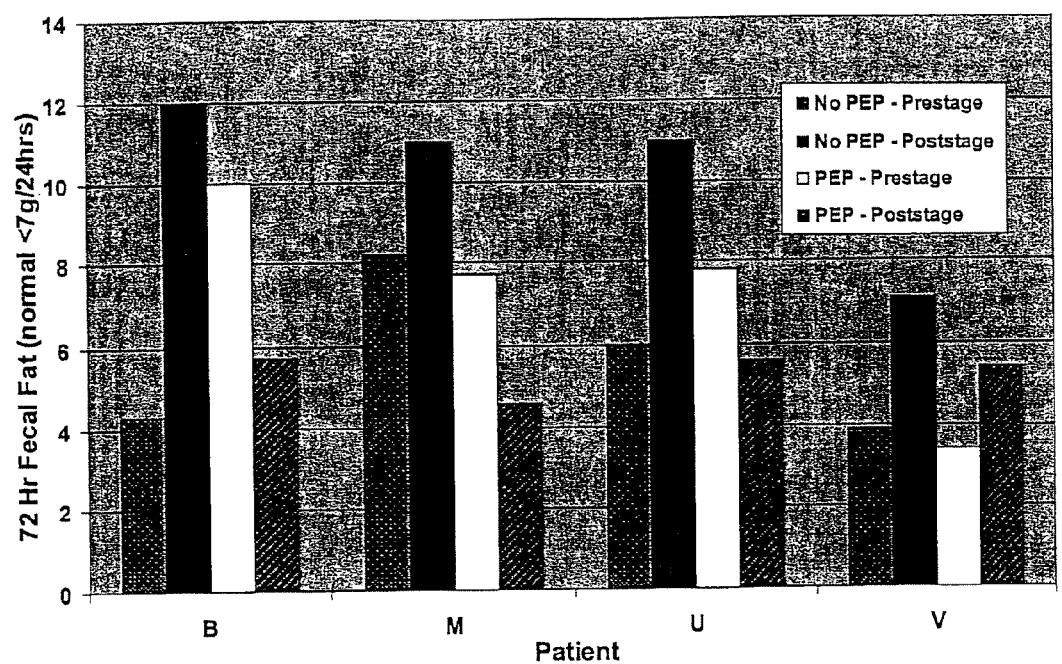
FIG. 17. Fecal fats for patients with normal to mild pre-stage steatorrhea and a positive fecal fat gluten challenge.

Fourteen patients had a full set of urine xylose data to analyze. In 5 of the remaining 6 patients the baseline urine sample volume was erroneously not recorded, and an additional patient had insufficient urinary output (35 ml for a 5-hour collection)). Using the above criteria, we assessed the response to the gluten challenge in the group of fourteen patients as a whole, and also the subgroup of patients that had no pre-stage xylose malabsorption (FIG. 2). In the first analysis, 8 of the 14 patients (57%) developed xylose malabsorption when challenged with PTC-Gluten. All 6 of the patients failing to respond to the gluten challenge had significant (>10 g/24 h) pre-existing fat malabsorption, in contrast to none of the 8 patients who had a positive gluten challenge. PEP was effective in obviating the development of xylose malabsorption in the other stage in 4 patients (50%) (Table 5a). In the subgroup of patients having normal pre-stage (i.e. before both stages) xylose absorption (10 patients), 5 (50%) patients had a positive gluten challenge (Table 7, FIG. 16). Three of these 5 patients (60%) avoided developing xylose malabsorption when taking the gluten pre-treated with PEP.

TABLE 7a

Urine Xyloses for Patients with a Positive Xylose Gluten Challenge

|  | No pep | | pep | |
|---|---|---|---|---|
| Patient | Pre-Stage | Post-Stage | Pre-Stage | Post-Stage |
| D | 9.4 | 4.4 | 6.2 | 7.2 |
| E | 6.0 | 1.3 | 3.4 | 6.1 |
| J | 2.2 | 0.8 | 4.3 | 2.5 |
| M | 5.5 | 3.2 | 7.8 | 3.6 |
| O | 4.2 | 3.1 | 4.3 | 4.1 |
| Q | 2.4 | 0.8 | 2.2 | 1.6 |
| U | 9.9 | 4.2 | 7.3 | 1.4 |
| V | 5.6 | 3.2 | 6.2 | 6.0 |

The stool for fecal fat analysis was lost in one of the 20 patients, and two patients had an incomplete stool collection (<150 g/24 h) for one of the four stool collections. These patients were excluded from subsequent analysis. Of the remaining 17 patients, 7 had a positive gluten challenge based on the fecal fat test (Tables 8, 9). In this group of gluten-responsive patients, ingestion of PEP-treated gluten avoided the development of fat malabsorption in the treatment stage in 5 of the 7 (71%). Notably, a minority of these asymptomatic Celiac patients in apparent remission (3 of 17 patients (18%)) had completely normal pre-stage fat absorption, but most of these had very a very mild increase in the fecal fat excretion. Analysis of the larger subgroup of 8 patients (47%) with either normal fat absorption or only mild steatorrhea (fecal fat up to 10 g/24 h) (Table 8, 9), revealed that four had a positive gluten challenge. All of these individuals (100%) absorbed fat normally after ingesting the PEP-treated gluten.

TABLE 8

Results of the Gluten Challenge Based on Fecal Fat Testing

|  | All patients with full Fecal Fat data (N = 17) | | Subgroup with normal to Mild Steatorrhea (N = 8) | |
|---|---|---|---|---|
| Positive Gluten Challenge | 7/17 | 41% | 4/8 | 50% |
| PEP Effective | 5/7 | 71% | 4/4 | 100% |

TABLE 9

Fecal Fats of Patients with a Positive Fecal Fat Gluten Challenge

|  | No pep | | pep | |
|---|---|---|---|---|
| Patient | Pre-Stage | Post-Stage | Pre-Stage | Post-Stage |
| B | 4.3 | 12 | 10 | 5.7 |
| M | 8.2 | 11 | 7.7 | 4.6 |
| P | 4.9 | 12 | 11 | 5.8 |
| S | 15 | 24 | 8.2 | 25 |
| T | 16 | 22 | 25 | 15 |

TABLE 9-continued

Fecal Fats of Patients with a Positive Fecal Fat Gluten Challenge

| Patient | No pep | | pep | |
| --- | --- | --- | --- | --- |
| | Pre-Stage | Post-Stage | Pre-Stage | Post-Stage |
| U | 6 | 11 | 7.8 | 5.6 |
| V | 3.9 | 7 | 3.4 | 5.4 |

In this double-blind trial, symptoms were not distinguishable during the control (PTC-Gluten) versus the PEP-digested (PTC-Gluten+PEP) stage, despite a high prevalence of fat malabsorption (66%) and carbohydrate (21%) in the Celiac patients in remission at baseline, before either type of pre-treated gluten was consumed. The fecal fat is a more sensitive test for documenting intestinal dysfunction than the xylose urine test, and this is consistent with the finding that only one-third of patients with baseline fat malabsorption were found to have an abnormal xylose test. Nevertheless, the absorption of xylose requires no pancreatic luminal enzymes and hence even a borderline abnormal value indicates the reason for increased stool fat output is due to an enteric rather than a pancreatic lesion.

Celiac serum antibody titers (gliadin, endomysial, transglutaminase) have been found to correlate closely with the histological findings in untreated Celiac Sprue, and are frequently used to monitor adherence to a gluten-exclusion diet. However, we had found that 21 days of low-dose (5-10 Gm per day) oral gluten supplementation does not convert these antibody studies to the abnormal range. The current study revealed that 7 patients (# 2, 7, 12, 13, 15, 16, 17, 18; see tables) had elevated transglutaminase titers at baseline, 6 of these being IgA type antibodies and one IgG. All of these patients also had malabsorption. Four of these same patients were positive for anti-gliadin antibodies. However, most striking was the fact that all antibodies were negative in 8 other patients who had malabsorption of fat or carbohydrate. It appears that intestinal absorptive tests may be superior to the serum antibody tests in monitoring the intestinal function in Celiac Sprue.

The finding that two-thirds of Celiac individuals in clinical remission have fat malabsorption and one of five have carbohydrate malabsorption suggests strongly that intestinal dysfunction due to continuing intestinal injury occurs commonly in the disease, despite lack of symptoms and maintenance of a gluten-exclusion diet. This emphasizes the need for identifying incremental long-term therapy for Celiac Sprue in addition to the conventional dietary gluten exclusion. Celiac Sprue patients with chronic fat or carbohydrate malabsorption could be treated with oral enzyme therapy in order to improve their malabsorptive symptoms with the longer-term goal of reducing the relatively high prevalence of osteopenia and iron deficiency anemia. An endoscopic biopsy would also be indicated whenever malabsorption is identified, and could be a useful tool to monitor therapeutic efficacy of the oral enzyme.

In those who had normal intestinal function, as evidenced by the absence of malabsorption in the pre-test stage and who then mounted a malabsorptive response to PTC-Gluten ingestion, no malabsorption was observed in the majority of these gluten-responsive Celiac patients when the gliadin peptides from PTC-Gluten were further processed prior to ingestion by PEP treatment (PTC-Gluten +PEP). This indicates that the pre-treatment of dietary gluten peptides with PEP results in appreciable ablation of their toxic properties for the Celiac small intestine. The fact that PEP treated gluten does not induce malabsorption demonstrates strongly that this peptidase is sufficient to eliminate the bulk of injurious gliadin in food sources of gluten, for example as an oral peptidase supplement as supportive therapy in patients with Celiac Sprue. The need for additional therapy in Celiac Sprue is even more essential in view of the finding that many Celiac patients in full clinical remission have continuing sub-clinical malabsorption, undoubtedly due to continuing intestinal damage, despite their maintenance of dietary gluten exclusion.

Based on the above results, the clinical trials may be varied as follows. Since not all of the Celiac Sprue patents in clinical remission responded to a 5 g gluten dose with fat and carbohydrate malabsorption in this study, future studies may increase the gluten dose to 10 g/day. In addition, the radiotelemetry video capsule may provide more information for assessment of overall small intestinal structure. Finally, an oligosaccharide permeability test as an additional assessment of intestinal integrity may be desirable.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A composition, comprising:
   isolated *Myxococcus xanthus* prolyl endopeptidase (PEP) consisting of the amino acid sequence forth in SEQ ID NO:47, admixed with gluten-containing food.

2. The composition of claim 1, wherein said isolated *Myxococcus xanthus* prolyl endopeptidase (PEP) comprising the amino acid sequence forth in SEQ ID NO:47 is provided in a unit dosage form containing an amount of the isolated *Myxococcus xanthus* PEP effective to cleave a gluten oligopeptide having the amino acid sequence of SEQ ID NO:12 to fragments shorter than 8 amino acids and a pharmaceutically acceptable excipient.

3. The composition of claim 2, wherein the isolated *Myxococcus xanthus* PEP is a recombinant protein.

4. The composition of claim 2, wherein the unit dosage form of isolated *Myxococcus xanthus* PEP is coated with an enteric coating.

5. The composition of claim 2, wherein the amount of isolated *Myxococcus xanthus* PEP in the unit dosage form is 500 units to 20,000 units, wherein one unit is the amount of enzyme required to hydrolyze 1 μmol Cbz-Gly-Pro-pNA per min under specified conditions.

6. The composition of claim 2, wherein the amount of isolated *Myxococcus xanthus* PEP in the unit dosage is from 0.1 mg to 500 mg.

* * * * *

UNITED STATES PATENT AND TRADEMARK OFFICE
CERTIFICATE OF CORRECTION

| | | |
|---|---|---|
| PATENT NO. | : 8,143,210 B2 | Page 1 of 1 |
| APPLICATION NO. | : 11/775824 | |
| DATED | : March 27, 2012 | |
| INVENTOR(S) | : Lu Shan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 625 days.

Signed and Sealed this
Sixteenth Day of April, 2013

Teresa Stanek Rea
*Acting Director of the United States Patent and Trademark Office*

SEQUENCE LISTING

```
<160> NUMBER OF SEQ ID NOS: 47

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
 1               5                  10
```

```
<210> SEQ ID NO 2
<211> LENGTH: 12
<212> TYPE: PRT
<213> ORGANISM: Triticum aestivum
<220> FEATURE:
<221> NAME/KEY: PYRROLIDONE CAR
<222> LOCATION: (1)...(12)

<400> SEQUENCE: 2

Gln Leu Gln Pro Phe Pro Gln Pro Gln Leu Pro Tyr
 1               5                  10

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
 1               5                  10

<210> SEQ ID NO 4
<211> LENGTH: 13
<212> TYPE: PRT
<213> ORGANISM: Triticum aestivum

<400> SEQUENCE: 4

Pro Gln Pro Gln Leu Pro Tyr Pro Gln Pro Gln Leu Pro
 1               5                  10

<210> SEQ ID NO 5
<211> LENGTH: 11
<212> TYPE: PRT
<213> ORGANISM: Triticum aestivum

<400> SEQUENCE: 5

Gln Leu Gln Pro Phe Pro Gln Pro Gln Leu Pro
 1               5                  10

<210> SEQ ID NO 6
<211> LENGTH: 11
<212> TYPE: PRT
<213> ORGANISM: Triticum aestivum

<400> SEQUENCE: 6

Gln Pro Gln Phe Pro Gln Pro Gln Leu Pro Tyr
 1               5                  10

<210> SEQ ID NO 7
<211> LENGTH: 9
<212> TYPE: PRT
<213> ORGANISM: Triticum aestivum

<400> SEQUENCE: 7

Gln Pro Phe Pro Gln Pro Gln Leu Pro
 1               5

<210> SEQ ID NO 8
<211> LENGTH: 6
<212> TYPE: PRT
<213> ORGANISM: Triticum aestivum

<400> SEQUENCE: 8

Pro Gln Pro Gln Leu Pro
 1               5
```

```
<210> SEQ ID NO 9
<211> LENGTH: 13
<212> TYPE: PRT
<213> ORGANISM: Triticum aestivum

<400> SEQUENCE: 9

Arg Arg Leu Ile Glu Asp Asn Glu Tyr Thr Ala Arg Gly
1               5                   10

<210> SEQ ID NO 10
<211> LENGTH: 10
<212> TYPE: PRT
<213> ORGANISM: Triticum aestivum

<400> SEQUENCE: 10

Gln Pro Phe Pro Gln Pro Gln Leu Pro Tyr
1               5                   10

<210> SEQ ID NO 11
<211> LENGTH: 7
<212> TYPE: PRT
<213> ORGANISM: Triticum aestivum

<400> SEQUENCE: 11

Phe Pro Gln Pro Gln Leu Pro
1               5

<210> SEQ ID NO 12
<211> LENGTH: 33
<212> TYPE: PRT
<213> ORGANISM: Triticum aestivum

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 13
<211> LENGTH: 10
<212> TYPE: PRT
<213> ORGANISM: Triticum aestivum

<400> SEQUENCE: 13

Gln Pro Gln Gln Ser Phe Pro Gln Gln Gln
1               5                   10

<210> SEQ ID NO 14
<211> LENGTH: 12
<212> TYPE: PRT
<213> ORGANISM: Triticum aestivum

<400> SEQUENCE: 14

Gln Leu Gln Pro Phe Pro Gln Pro Glu Leu Pro Tyr
1               5                   10

<210> SEQ ID NO 15
<211> LENGTH: 14
<212> TYPE: PRT
<213> ORGANISM: Triticum aestivum

<400> SEQUENCE: 15

Pro Gln Pro Glu Leu Pro Tyr Pro Gln Pro Glu Leu Pro Tyr
```

<210> SEQ ID NO 16
<211> LENGTH: 10
<212> TYPE: PRT
<213> ORGANISM: Triticum aestivum

<400> SEQUENCE: 16

Gln Pro Gln Gln Ser Phe Pro Glu Gln Gln
1               5                   10

<210> SEQ ID NO 17
<211> LENGTH: 13
<212> TYPE: PRT
<213> ORGANISM: Triticum aestivum

<400> SEQUENCE: 17

Pro Gln Pro Glu Leu Pro Tyr Pro Gln Pro Gln Leu Pro
1               5                   10

<210> SEQ ID NO 18
<211> LENGTH: 14
<212> TYPE: PRT
<213> ORGANISM: Triticum aestivum

<400> SEQUENCE: 18

Pro Gln Pro Glu Leu Pro Tyr Pro Gln Pro Gln Pro Leu Pro
1               5                   10

<210> SEQ ID NO 19
<211> LENGTH: 5
<212> TYPE: PRT
<213> ORGANISM: Triticum aestivum

<400> SEQUENCE: 19

Gly Pro Leu Gly Pro
1               5

<210> SEQ ID NO 20
<211> LENGTH: 9
<212> TYPE: PRT
<213> ORGANISM: Triticum aestivum

<400> SEQUENCE: 20

Pro Phe Pro Gln Pro Gln Leu Pro Tyr
1               5

<210> SEQ ID NO 21
<211> LENGTH: 27
<212> TYPE: PRT
<213> ORGANISM: Triticum aestivum

<400> SEQUENCE: 21

Pro Gln Pro Gln Leu Pro Tyr Pro Gln Pro Gln Leu Pro Tyr
1               5                   10                  15
Pro Gln Pro Gln Pro Gln Leu Pro Tyr Pro Gln
            20                  25

<210> SEQ ID NO 22
<211> LENGTH: 18
<212> TYPE: PRT
<213> ORGANISM: Triticum aestivum

<400> SEQUENCE: 22

Pro Tyr Pro Gln Pro Gln Leu Pro Tyr Pro Tyr Pro Gln Pro Gln Leu

```
                1               5                  10                 15

Pro Tyr

<210> SEQ ID NO 23
<211> LENGTH: 8
<212> TYPE: PRT
<213> ORGANISM: Triticum aestivum

<400> SEQUENCE: 23

Trp Gln Ile Pro Glu Gln Ser Arg
1               5

<210> SEQ ID NO 24
<211> LENGTH: 34
<212> TYPE: PRT
<213> ORGANISM: Triticum aestivum

<400> SEQUENCE: 24

Gln Pro Gln Pro Phe Pro Pro Gln Leu Pro Tyr Pro Gln Thr Gln Pro
1               5                  10                 15

Phe Pro Pro Gln Gln Pro Tyr Pro Gln Pro Gln Pro Tyr Pro Gln
            20                 25                 30

Pro Gln

<210> SEQ ID NO 25
<211> LENGTH: 35
<212> TYPE: PRT
<213> ORGANISM: Triticum aestivum

<400> SEQUENCE: 25

Gln Gln Gln Pro Phe Pro Gln Gln Pro Ile Pro Gln Gln Pro Gln Pro
1               5                  10                 15

Tyr Pro Gln Gln Pro Gln Pro Tyr Pro Gln Gln Pro Phe Pro Pro Gln
            20                 25                 30

Gln Pro Phe
        35

<210> SEQ ID NO 26
<211> LENGTH: 30
<212> TYPE: PRT
<213> ORGANISM: Triticum aestivum

<400> SEQUENCE: 26

Gln Pro Phe Pro Gln Pro Gln Gln Thr Phe Pro Gln Gln Pro Gln Leu
1               5                  10                 15

Pro Phe Pro Gln Gln Pro Gln Gln Pro Phe Pro Gln Pro Gln
            20                 25                 30

<210> SEQ ID NO 27
<211> LENGTH: 30
<212> TYPE: PRT
<213> ORGANISM: Triticum aestivum

<400> SEQUENCE: 27

Gln Pro Phe Pro Gln Pro Gln Gln Pro Thr Pro Ile Gln Pro Gln Gln
1               5                  10                 15

Pro Phe Pro Gln Arg Pro Gln Gln Pro Phe Pro Gln Pro Gln
            20                 25                 30

<210> SEQ ID NO 28
<211> LENGTH: 17
<212> TYPE: PRT
```

-continued

<213> ORGANISM: Triticum aestivum

<400> SEQUENCE: 28

Tyr Gln Glu Pro Val Leu Gly Pro Val Arg Gly Pro Phe Pro Ile Ile
1               5                   10                  15
Val

<210> SEQ ID NO 29
<211> LENGTH: 9
<212> TYPE: PRT
<213> ORGANISM: Triticum aestivum

<400> SEQUENCE: 29

Arg Pro Lys His Pro Ile Lys His Gln
1               5

<210> SEQ ID NO 30
<211> LENGTH: 9
<212> TYPE: PRT
<213> ORGANISM: Triticum aestivum

<400> SEQUENCE: 30

Ile Gln Pro Gln Gln Pro Ala Gln Leu
1               5

<210> SEQ ID NO 31
<211> LENGTH: 9
<212> TYPE: PRT
<213> ORGANISM: Triticum aestivum

<400> SEQUENCE: 31

Gln Gln Pro Gln Gln Pro Tyr Pro Gln
1               5

<210> SEQ ID NO 32
<211> LENGTH: 9
<212> TYPE: PRT
<213> ORGANISM: Triticum aestivum

<400> SEQUENCE: 32

Ser Gln Pro Gln Gln Gln Phe Pro Gln
1               5

<210> SEQ ID NO 33
<211> LENGTH: 9
<212> TYPE: PRT
<213> ORGANISM: Triticum aestivum

<400> SEQUENCE: 33

Gln Gln Pro Phe Pro Gln Gln Pro Gln
1               5

<210> SEQ ID NO 34
<211> LENGTH: 9
<212> TYPE: PRT
<213> ORGANISM: Triticum aestivum

<400> SEQUENCE: 34

Pro Phe Ser Gln Gln Gln Gln Pro Val
1               5

<210> SEQ ID NO 35
<211> LENGTH: 26
<212> TYPE: PRT
<213> ORGANISM: Triticum aestivum

```
<400> SEQUENCE: 35

Phe Leu Gln Pro Gln Gln Pro Phe Pro Gln Gln Pro Gln Gln Pro Tyr
1               5                   10                  15
Pro Gln Gln Pro Gln Gln Pro Phe Pro Gln
            20                  25

<210> SEQ ID NO 36
<211> LENGTH: 6
<212> TYPE: PRT
<213> ORGANISM: Triticum aestivum

<400> SEQUENCE: 36

Gln Pro Gln Gln Pro Tyr
1               5

<210> SEQ ID NO 37
<211> LENGTH: 34
<212> TYPE: DNA
<213> ORGANISM: Flavobacterium meningosepticum

<400> SEQUENCE: 37
aaccaatcat atgaagtaca acaaactttc tgtg                               34

<210> SEQ ID NO 38
<211> LENGTH: 26
<212> TYPE: DNA
<213> ORGANISM: Flavobacterium meningosepticum

<400> SEQUENCE: 38
gataaaaacg gaaagcttgt aagggc                                        26

<210> SEQ ID NO 39
<211> LENGTH: 26
<212> TYPE: DNA
<213> ORGANISM: Flavobacterium meningosepticum

<400> SEQUENCE: 39
gcccttacaa gctttccgtt tttatc                                        26

<210> SEQ ID NO 40
<211> LENGTH: 40
<212> TYPE: DNA
<213> ORGANISM: Flavobacterium meningosepticum

<400> SEQUENCE: 40
cccttaattt tcaaatttta gctcgagttt atgatttata                         40

<210> SEQ ID NO 41
<211> LENGTH: 29
<212> TYPE: DNA
<213> ORGANISM: Sphingomonas capsulata

<400> SEQUENCE: 41
aggatatcca tatgaagaac cgcttgtgg                                     29

<210> SEQ ID NO 42
<211> LENGTH: 25
<212> TYPE: DNA
<213> ORGANISM: Sphingomonas capsulata

<400> SEQUENCE: 42
gacaacctcg aatccgtcgg cattg                                         25
```

<210> SEQ ID NO 43
<211> LENGTH: 25
<212> TYPE: DNA
<213> ORGANISM: Sphingomonas capsulata

<400> SEQUENCE: 43
caatgccgac ggattcgagg ttgtc                                          25

<210> SEQ ID NO 44
<211> LENGTH: 24
<212> TYPE: DNA
<213> ORGANISM: Sphingomonas capsulata

<400> SEQUENCE: 44
cgcggggacc tcgagtagaa actg                                           24

<210> SEQ ID NO 45
<211> LENGTH: 26
<212> TYPE: DNA
<213> ORGANISM: Myxococcus xanthus

<400> SEQUENCE: 45
ctccccatat gtcctacccg gcgacc                                         26

<210> SEQ ID NO 46
<211> LENGTH: 32
<212> TYPE: DNA
<213> ORGANISM: Myxococcus xanthus

<400> SEQUENCE: 46
gtggcggcgc agggccgcaa gcttcccaag cg                                  32

<210> SEQ ID NO 47
<211> LENGTH: 689
<212> TYPE: PRT
<213> ORGANISM: Myxococcus xanthus

<400> SEQUENCE: 47

Met Ser Tyr Pro Ala Thr Arg Ala Glu Gln Val Val Asp Thr Leu His
 1               5                  10                  15

Gly Val Gln Val Ala Asp Pro Tyr Arg Trp Leu Glu Asp Lys Ala
            20                  25                  30

Pro Glu Val Gln Thr Trp Met Thr Ala Gln Asn Ala His Ala Arg Glu
        35                  40                  45

Ala Leu Ala Lys Phe Pro Gly Arg Glu Ala Leu Ala Ala Arg Phe Lys
    50                  55                  60

Glu Leu Phe Tyr Thr Asp Ser Val Ser Thr Pro Ser Arg Arg Asn Gly
65                  70                  75                  80

Arg Phe Phe Tyr Val Arg Thr His Lys Asp Lys Glu Lys Ala Ile Leu
                85                  90                  95

Tyr Trp Arg Gln Gly Glu Ser Gly Gln Glu Lys Val Leu Leu Asp Pro
            100                 105                 110

Asn Gly Trp Ser Lys Asp Gly Thr Val Ser Leu Gly Thr Trp Ala Val
        115                 120                 125

Ser Trp Asp Gly Lys Lys Val Ala Phe Ala Gln Lys Pro Asn Ala Ala
    130                 135                 140

Asp Glu Ala Val Leu His Val Ile Asp Val Asp Ser Gly Glu Trp Ser
145                 150                 155                 160

Lys Val Asp Val Ile Glu Gly Gly Lys Tyr Ala Thr Pro Lys Trp Thr
                165                 170                 175

-continued

```
Pro Asp Ser Lys Gly Phe Tyr Tyr Glu Trp Leu Pro Thr Asp Pro Ser
            180                 185                 190

Ile Lys Val Asp Glu Arg Pro Gly Tyr Thr Thr Ile Arg Tyr His Thr
        195                 200                 205

Leu Gly Thr Glu Pro Ser Lys Asp Thr Val Val His Glu Arg Thr Gly
    210                 215                 220

Asp Pro Thr Thr Phe Leu Gln Ser Asp Leu Ser Arg Asp Gly Lys Tyr
225                 230                 235                 240

Leu Phe Val Tyr Ile Leu Arg Gly Trp Ser Glu Asn Asp Val Tyr Trp
                245                 250                 255

Lys Arg Pro Gly Glu Lys Asp Phe Arg Leu Leu Val Lys Gly Val Gly
            260                 265                 270

Ala Lys Tyr Glu Val His Ala Trp Lys Asp Arg Phe Tyr Val Leu Thr
        275                 280                 285

Asp Glu Gly Ala Pro Arg Gln Arg Val Phe Glu Val Asp Pro Ala Lys
    290                 295                 300

Pro Ala Arg Ala Ser Trp Lys Glu Ile Val Pro Glu Asp Ser Ser Ala
305                 310                 315                 320

Ser Leu Leu Ser Val Ser Ile Val Gly Gly His Leu Ser Leu Glu Tyr
                325                 330                 335

Leu Lys Asp Ala Thr Ser Glu Val Arg Val Ala Thr Leu Lys Gly Lys
            340                 345                 350

Pro Val Arg Thr Val Gln Leu Pro Gly Val Gly Ala Ala Ser Asn Leu
        355                 360                 365

Met Gly Leu Glu Asp Leu Asp Asp Ala Tyr Tyr Val Phe Thr Ser Phe
    370                 375                 380

Thr Thr Pro Arg Gln Ile Tyr Lys Thr Ser Val Ser Thr Gly Lys Ser
385                 390                 395                 400

Glu Leu Trp Ala Lys Val Asp Val Pro Met Asn Pro Glu Gln Tyr Gln
                405                 410                 415

Val Glu Gln Val Phe Tyr Ala Ser Lys Asp Gly Thr Lys Val Pro Met
            420                 425                 430

Phe Val Val His Arg Lys Asp Leu Lys Arg Asp Gly Asn Ala Pro Thr
        435                 440                 445

Leu Leu Tyr Gly Tyr Gly Gly Phe Asn Val Asn Met Glu Ala Asn Phe
    450                 455                 460

Arg Ser Ser Ile Leu Pro Trp Leu Asp Ala Gly Gly Val Tyr Ala Val
465                 470                 475                 480

Ala Asn Leu Arg Gly Gly Gly Glu Tyr Gly Lys Ala Trp His Asp Ala
                485                 490                 495

Gly Arg Leu Asp Lys Lys Gln Asn Val Phe Asp Asp Phe His Ala Ala
            500                 505                 510

Ala Glu Tyr Leu Val Gln Gln Lys Tyr Thr Gln Pro Lys Arg Leu Ala
        515                 520                 525

Ile Tyr Gly Gly Ser Asn Gly Gly Leu Leu Val Gly Ala Ala Met Thr
    530                 535                 540

Gln Arg Pro Glu Leu Tyr Gly Ala Val Val Cys Ala Val Pro Leu Leu
545                 550                 555                 560

Asp Met Val Arg Tyr His Leu Phe Gly Ser Gly Arg Thr Trp Ile Pro
                565                 570                 575

Glu Tyr Gly Thr Ala Glu Lys Pro Glu Asp Phe Lys Thr Leu His Ala
            580                 585                 590

Tyr Ser Pro Tyr His His Val Arg Pro Asp Val Arg Tyr Pro Ala Leu
```

```
                          595                 600                 605
Leu Met Met Ala Ala Asp His Asp Asp Arg Val Asp Pro Met His Ala
    610                 615                 620

Arg Lys Phe Val Ala Ala Val Gln Asn Ser Pro Gly Asn Pro Ala Thr
625                 630                 635                 640

Ala Leu Leu Arg Ile Glu Ala Asn Ala Gly His Gly Gly Ala Asp Gln
                645                 650                 655

Val Ala Lys Ala Ile Glu Ser Ser Val Asp Leu Tyr Ser Phe Leu Phe
            660                 665                 670

Gln Val Leu Asp Val Gln Gly Ala Gln Gly Gly Val Ala Ala Gln Gly
        675                 680                 685

Arg
```